United States Patent [19]
Kino et al.

[11] Patent Number: 5,217,952
[45] Date of Patent: Jun. 8, 1993

[54] PEPTIDES WS-9326A AND WS-9326B, DERIVATIVES THEREOF AND USES THEREOF

[75] Inventors: Tohru Kino, Tsuchiura; Motoaki Nishikawa, Tsukuba; Masami Ezaki, Tsukuba; Sumio Kiyoto, Tsukuba; Masakuni Okuhara, Tsukuba; Shigehiro Takase, Tsukuba; Satoshi Okada, Tsukuba; Nobuharu Shigematsu, Tsukuba, all of Japan

[73] Assignee: Fujisawa Pharmaceutical Co., Ltd., Osaka, Japan

[21] Appl. No.: 794,698

[22] Filed: Nov. 20, 1991

Related U.S. Application Data

[63] Continuation of Ser. No. 417,470, Oct. 5, 1989, abandoned, which is a continuation-in-part of Ser. No. 333,017, Apr. 4, 1989, abandoned, which is a continuation-in-part of Ser. No. 304,030, Jan. 31, 1989, abandoned.

[30] Foreign Application Priority Data

Feb. 2, 1988 [GB] United Kingdom .................. 8802229
Apr. 5, 1988 [GB] United Kingdom .................. 8807921

[51] Int. Cl.$^5$ .................. A61K 37/02; C07K 7/06; C07K 7/54
[52] U.S. Cl. .................. 514/11; 514/9; 514/16; 514/826; 530/317; 530/323; 530/329
[58] Field of Search .............. 530/317, 323, 329, 345; 514/9, 11, 16, 826

[56] References Cited

U.S. PATENT DOCUMENTS

| | | | |
|---|---|---|---|
| 3,995,027 | 11/1976 | Gale et al. | 424/115 |
| 4,161,520 | 7/1979 | Osborne et al. | 424/115 |
| 4,456,592 | 6/1984 | Okumura et al. | 530/317 |
| 4,742,155 | 5/1988 | Umezawa et al. | 530/317 |
| 4,868,174 | 9/1989 | Takaza et al. | 514/202 |
| 4,963,530 | 10/1990 | Hemmi et al. | 514/19 |

FOREIGN PATENT DOCUMENTS 091781 10/1983 European Pat. Off. .
235795 9/1987 European Pat. Off. .

OTHER PUBLICATIONS

Drautz et al., Chem. Abst. vol. 85, No. 18903m (1976).
Dorland's Illustrated Medical Dictionary, 26th Ed., W. B. Saunders Company, Philadelphia, p. 66 (1985).
Streitwieser et al., Introduction to Organic Chemistry, 3rd Ed., Macmillan Publishing Company New York, pp. 38–40 (1985).
Morrison et al., Organic Chemistry, 3rd Ed., Allyn and Bacon, Inc., Boston, pp. 68–70 (1973).
Hochlowski et al., Journal of Antibiotics, vol. 41, iss. 10, pp. 1300–1315, Tokyo, Japan, 1988.
The Journal of Antibiotics, vol. 34, No. 9, pp. 1107–1118, Sep. 1981, H.-P. Fiedler, et al., "Metabolic Products of Microorganisms, 200, Isolation and Characterization of Niphithricins A,B, and Elaiophylin, Antibiotics Produced . . .".

*Primary Examiner*—Y. Christina Chan
*Attorney, Agent, or Firm*—Oblon, Spivak, McClelland, Maier & Neustadt

[57] ABSTRACT

This invention relates to the novel peptides WS-9326A, WS-9326B, their derivatives and pharmaceutically acceptable salts thereof which have pharmacological activities, particularly in the treatment and/or prevention of asthma and/or pain.

10 Claims, 11 Drawing Sheets

PEPTIDES WS-9326A AND WS-9326B, DERIVATIVES THEREOF AND USES THEREOF

The present application is a continuation of application Ser. No. 07/417,470, filed Oct. 5, 1989, abandoned, which is a continuation-in-part of parent application Ser. No. 07/333,017, filed Apr. 4, 1989, abandoned, which is a continuation-in-part of grandparent application Ser. No. 07/304,030, filed Jan. 31, 1989, abandoned.

This invention relates to novel peptide derivatives and pharmaceutically acceptable salts thereof which have pharmacological activities.

More particularly, it relates to novel peptide derivatives and pharmaceutically acceptable salts thereof which have pharmacological activities such as substance P antagonism, neurokinin A (substance K) antagonism, analgesic action or the like, to processes for their production and to a pharmaceutical composition containing the same.

Accordingly, one object of this invention is to provide peptide derivatives and pharmaceutically acceptable salts thereof which are useful for treatment and prevention of asthma, various pains (e.g. headache, toothache, cancerous pain, etc.) and the like.

Another object of this invention is to provide processes for production of peptide derivatives and pharmaceutically acceptable salts thereof.

A further object of this invention is to provide a pharmaceutical composition containing, as an active ingredient, peptide derivatives or pharmaceutically acceptable salts thereof.

Still further object of this invention is to provide a use of peptide derivatives and pharmaceutically acceptable salts thereof for the treatment and prevention of asthma and the like.

The object peptide derivatives of the present invention can be represented by the following formula (I).

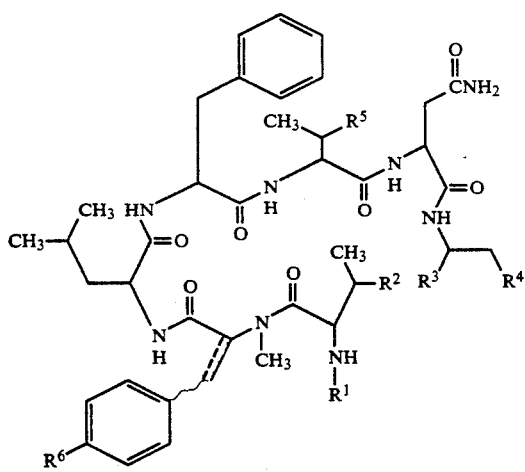

wherein
R$^1$ is hydrogen or an acyl group;
R$^2$ is hydroxy and
R$^3$ is carboxy or protected carboxy, or
R$^2$ and R$^3$ are linked together to represent a group of the formula:

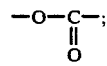

R$^4$ is hydroxy or protected hydroxy;
R$^5$ is hydroxy or protected hydroxy;
R$^6$ is hydroxy, protected hydroxy or lower alkoxy; and
$=$ is a single bond or a double bond.

According to the present invention, the new peptide derivatives (I) can be prepared by various processes.

Production by Synthetic Processes

Process 1

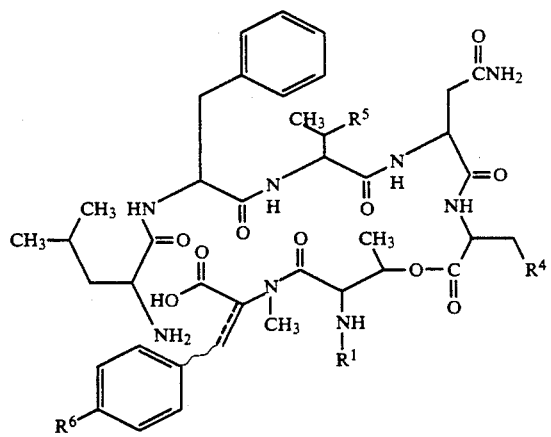

(II)
or a salt thereof

↓ Cyclization

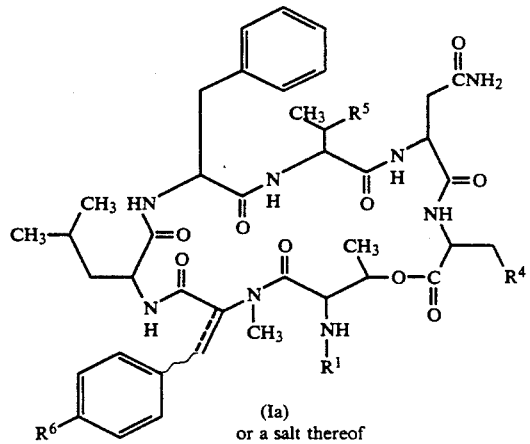

(Ia)
or a salt thereof

Process 2

3
-continued
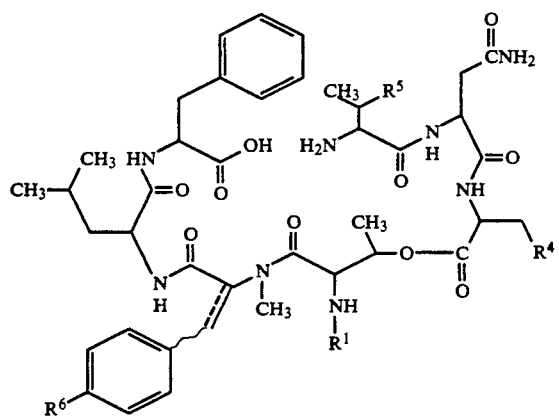
(III)
or a salt thereof
↓ Cyclization
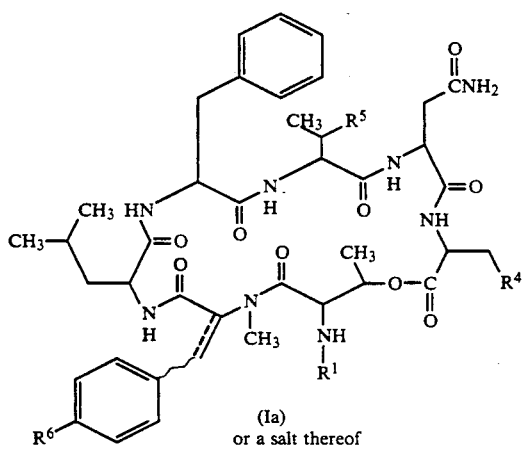
(Ia)
or a salt thereof
Process 3
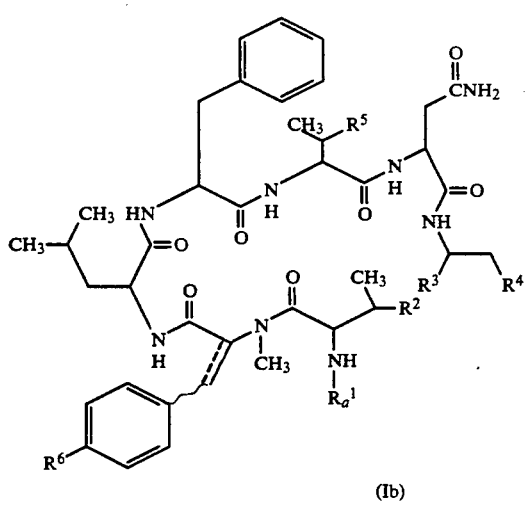
(Ib)
or a salt thereof
↓ Deacylation
4
-continued
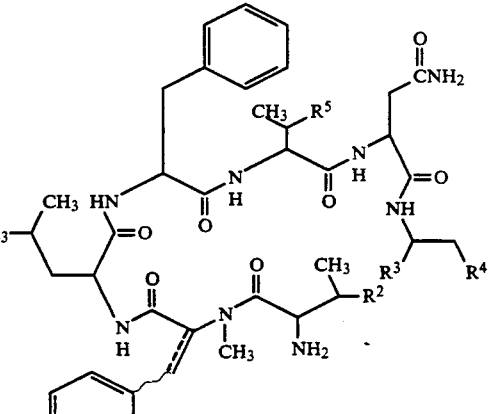
(Ic)
or a salt thereof
Process 4
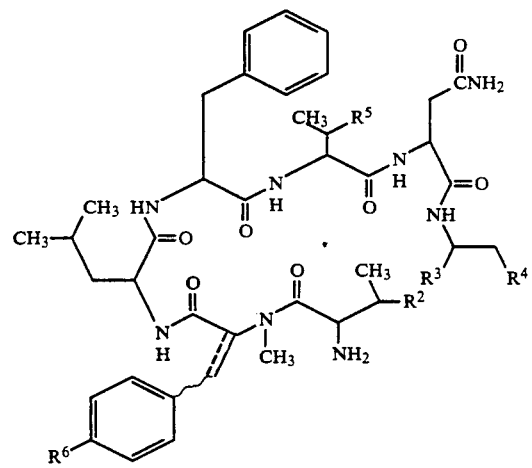
(Ic)
or its reactive derivative
at the amino group
or a salt thereof
↓ Acylation
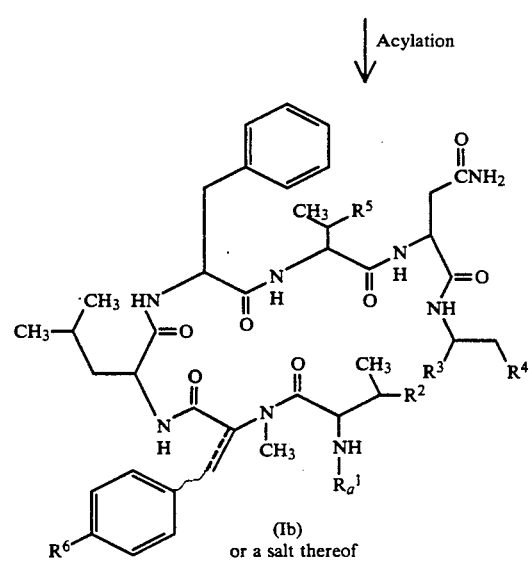
(Ib)
or a salt thereof
Process 5

-continued
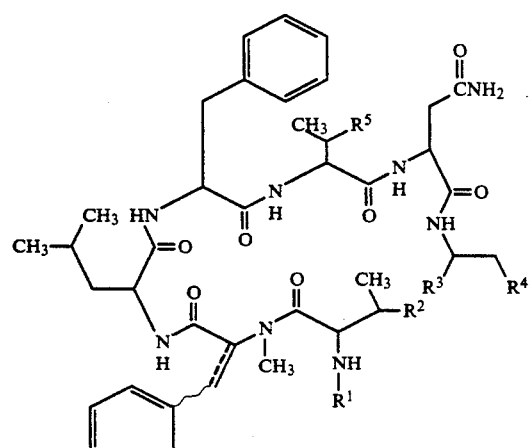
(Id) or a salt thereof
↓ Acylation
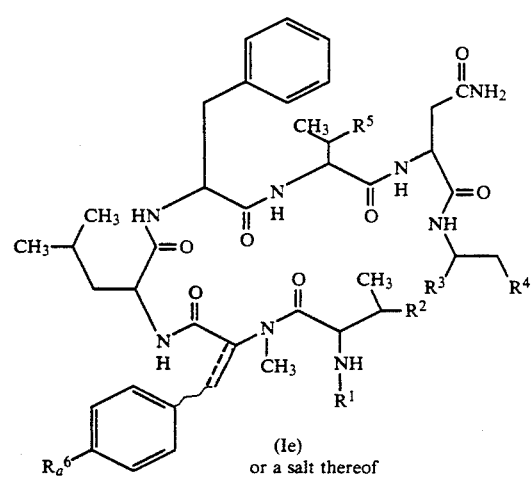
(Ie) or a salt thereof
Process 6
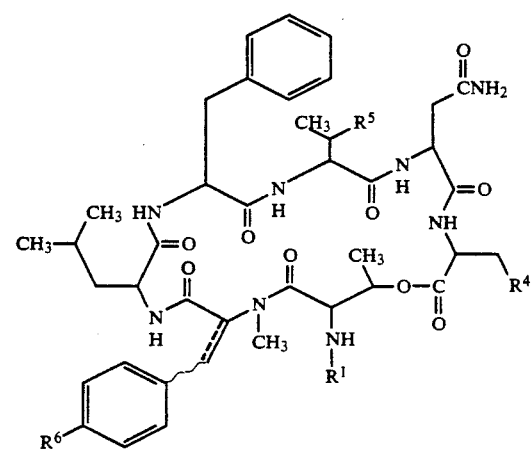
-continued
(Ia) or a salt thereof
↓ Hydrolysis
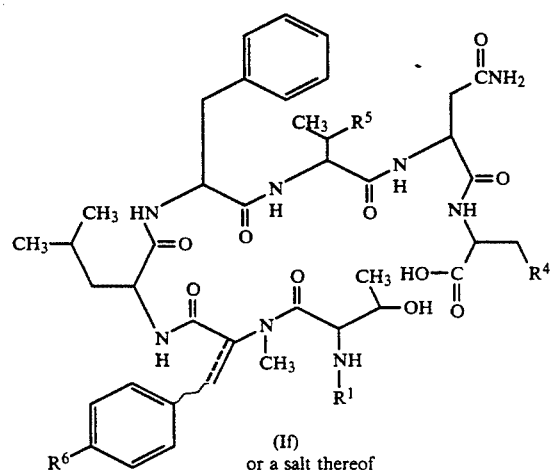
(If) or a salt thereof
Process 7
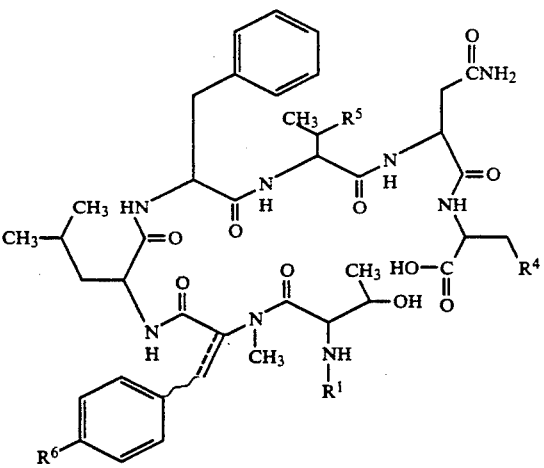
(If) or a salt thereof
↓ Esterification

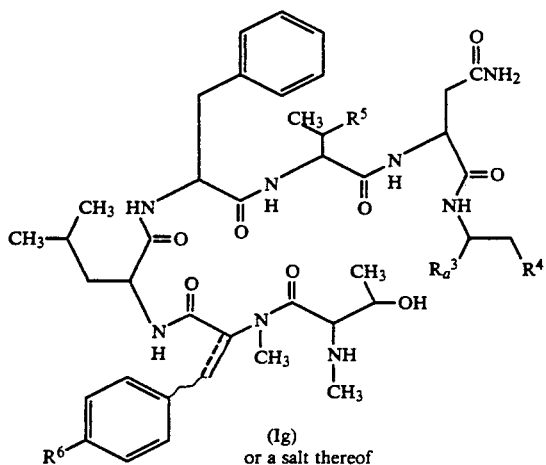

(Ig) or a salt thereof

Process 8

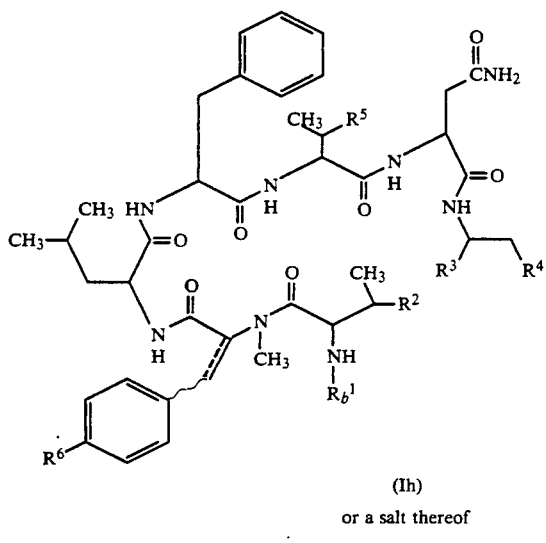

(Ih) or a salt thereof

Reduction

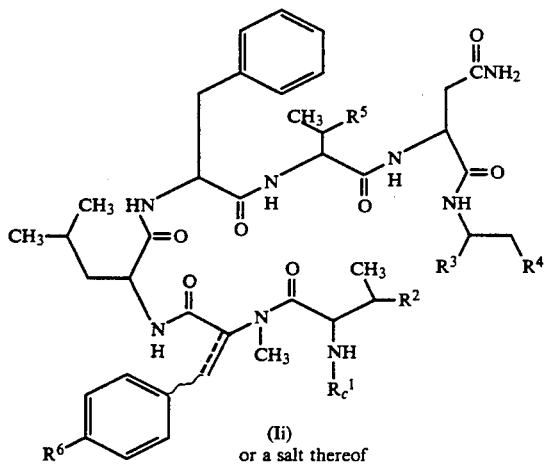

(Ii) or a salt thereof

Process 9

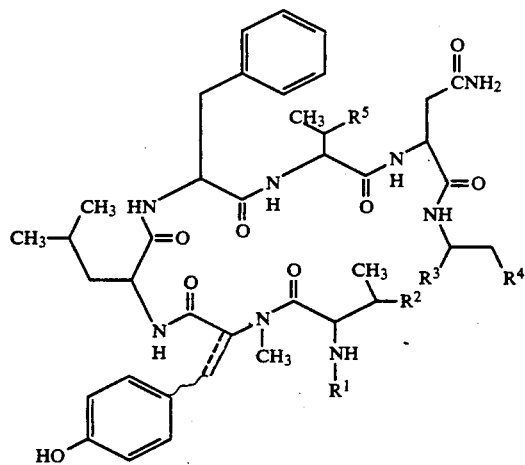

(Id) or a salt thereof

Alkylation

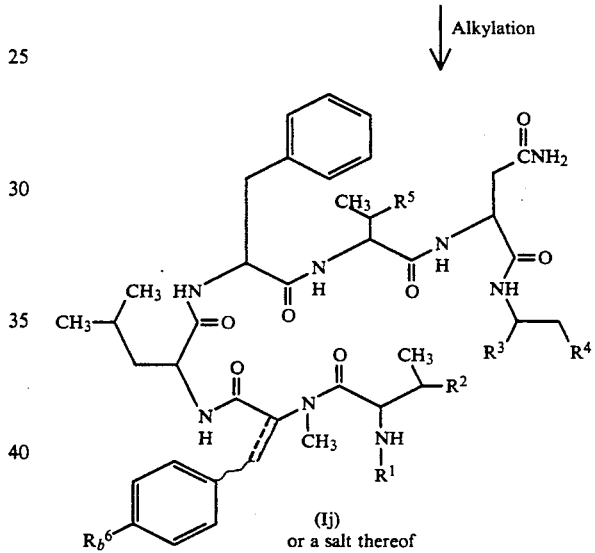

(Ij) or a salt thereof wherein
$R^1$, $R^4$, $R^5$, $R^6$ and === are each as defined above,
$R_a^1$ is an acyl group,
$R_a^6$ is acyloxy,
$R_a^3$ is esterified carboxy,
$R_b^1$ is ar(lower)alkenoyl substituted with a lower alkenyl group,
$R_c^1$ is ar(lower)alkanoyl substituted with a lower alkyl group,
$R_b^6$ is lower alkoxy.

The starting compounds (II) and (III) are novel and can be prepared by the following processes.

Process A

-continued

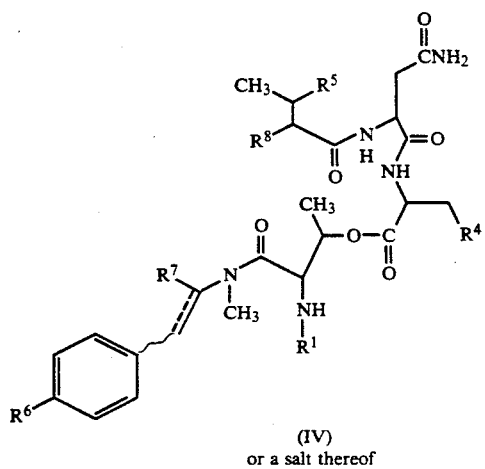

(IV)
or a salt thereof (i) Elimination reaction of the amino protective group in $R^8$
(ii)

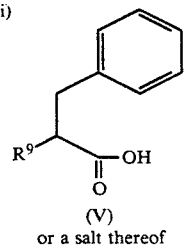

(V)
or a salt thereof

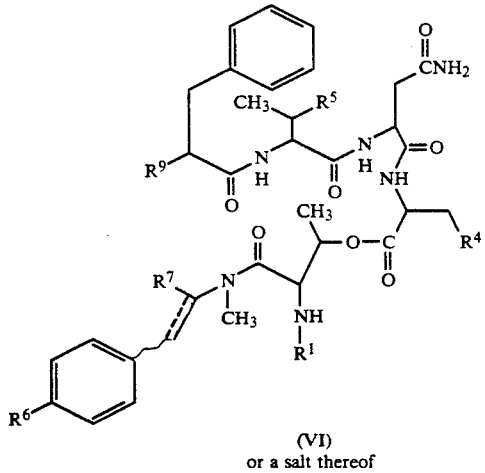

(VI)
or a salt thereof (i) Elimination reaction of the amino protective group in $R^9$
(ii)

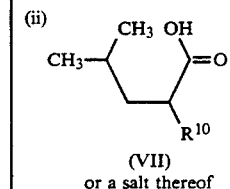

(VII)
or a salt thereof

-continued

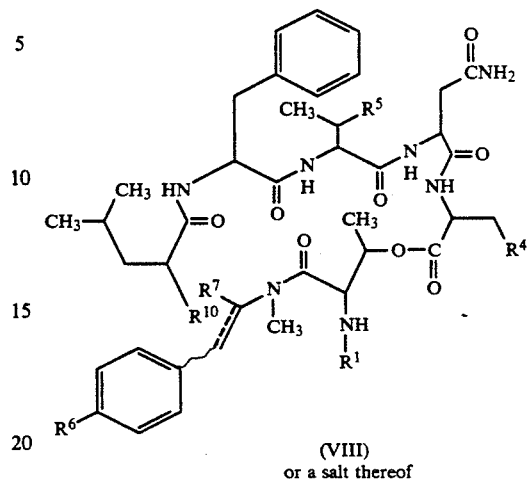

(VIII)
or a salt thereof

Elimination reaction of the amino protective group in $R^{10}$ and the carboxy protective group in $R^7$

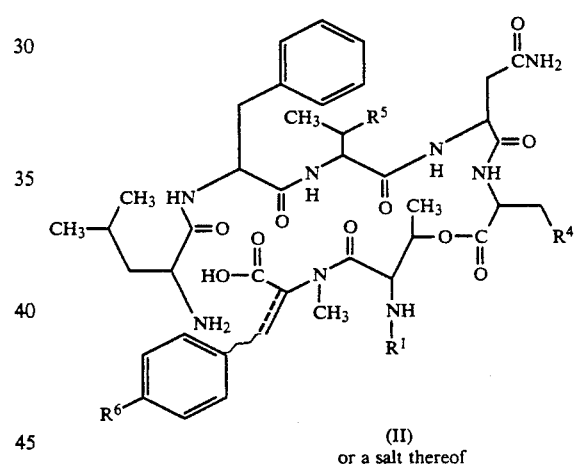

(II)
or a salt thereof

Process B

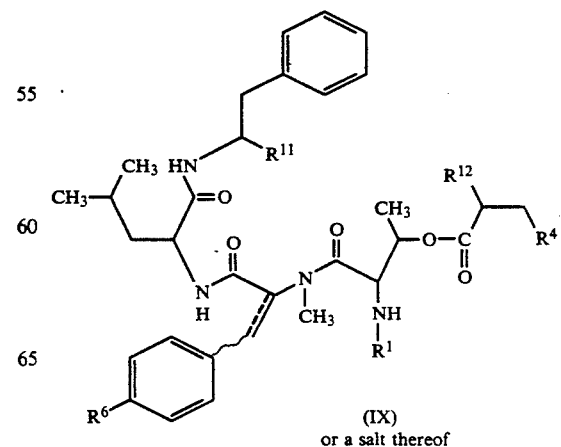

(IX)
or a salt thereof

-continued (i) Elimination reaction of the amino protective group in R¹²
(ii)

(X) or a salt thereof

↓

(XI) or a salt thereof (i) Elimination reaction of the amino protective group in R¹³
(ii)

(XII) or a salt thereof

↓

(XIII) or a salt thereof

Elimination reaction of the amino protective group in R¹⁴ and the carboxy protective group in R¹¹

↓

-continued (III) or a salt thereof wherein
$R^1$, $R^4$, $R^5$, $R^6$ and === are each as defined above,
$R^7$ is protected carboxy,
$R^8$ is protected amino,
$R^9$ is protected amino,
$R^{10}$ is protected amino,
$R^{11}$ is protected carboxy,
$R^{12}$ is protected amino,
$R^{13}$ is protected amino,
$R^{14}$ is protected amino.

The processes for preparing the starting and object compounds of the present invention are explained in the following.

Process 1

The compound (Ia) or a salt thereof can be prepared by subjecting the compound (II) or a salt thereof to cyclization reaction.

This reaction is carried out by the conventional method for cyclic peptide synthesis such as mixed acid anhydride method, activated ester method, carbodiimide method, or the like.

The reaction is usually carried out in a conventional solvent such as alcohol, tetrahydrofuran, ethyl acetate, N,N-dimethylformamide, dichloromethane, chloroform, or any other solvent which does not adversely influence the reaction.

The reaction temperature is not critical and the reaction is usually carried out under cooling to warming.

Process 2

The compound $(I_a)$ or a salt thereof can be prepared by subjecting the compound (III) or a salt thereof to cyclization reaction.

This reaction is carried out by the conventional method for cyclic peptide synthesis such as mixed acid anhydride, activated ester method, carbodiimide method, or the like.

The reaction is usually carried out in a conventional solvent such as alcohol, tetrahydrofuran, ethyl acetate, N,N-dimethylformamide, dichloromethane, chloroform, or any other solvent which does not adversely influence the reaction.

The reaction temperature is not critical and the reaction is usually carried out under cooling to warming.

Process 3

The compound (Ic) or a salt thereof can be prepared by subjecting the compound (Ib) or a salt thereof to deacylation reaction. Suitable method of this reaction may include conventional one such as hydrolysis, reduction and the like.

(i) For Hydrolysis:

The hydrolysis is preferably carried out in the presence of a base or an acid including Lewis acid.

Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]-non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

(ii) For reduction:

Reduction is carried out in a conventional manner, including chemical reduction and catalytic reduction.

Suitable reducing agents to be used in chemical reduction are a combination of a metal (e.g. tin, zinc, iron, etc.) or metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

Suitable catalysts to be used in catalytic reduction are conventional ones such as platinum catalysts (e.g. platinum plate, spongy platinum, platinum black, colloidal platinum, platinum oxide, platinum wire, etc.), palladium catalysts (e.g. spongy palladium, palladium black, palladium oxide, palladium on carbon, colloidal palladium palladium on barium sulfate, palladium on barium carbonate, etc. , nickel catalysts (e.g. reduced nickel, nickel oxide, Raney nickel, etc. , cobalt catalysts (e.g. reduced cobalt, Raney cobalt, etc.), iron catalysts (e.g. reduced iron, Raney iron, etc.), copper catalysts (e.g. reduced copper, Raney copper, Ullman copper, etc.) and the like. The reduction is usually carried out in a conventional solvent which does not adversely influence the reaction such as water, methanol, ethanol, propanol, N,N-dimethylformamide, tetrahydrofuran, or a mixture thereof. Additionally, in case that the above-mentioned acids to be used in chemical reduction are in liquid, they can also be used as a solvent.

The reaction temperature of this reduction is not critical and the reaction is usually carried out under cooling to warming.

Process 4

The compound (Ib) or a salt thereof can be prepared by subjecting the compound (Ic) or its reactive derivative at the amino group or a salt thereof to acylation reaction.

Suitable reactive derivative at the amino group of the compound (Ic) may include Schiff's base type imino or its tautomeric enamine type isomer formed by the reaction of the compound (Ic) with a carbonyl compound such as aldehyde, ketone or the like; a silyl derivative formed by the reaction of the compound (Ic) with a silyl compound such as bis(trimethylsilyl)acetamide, mono(trimethylsilyl)acetamide, bis(trimethylsilyl) urea or the like; a derivative formed by reaction of the compound (Ic) with phosphorus trichloride or phosgene, and the like.

Suitable acylating agent to be used in the present acylation reaction may include conventional one and can be shown by the formula: $R_a^1$—OH (XIV) (wherein $R_a^1$ is as defined above) or its reactive derivative or a salt thereof.

Suitable reactive derivative of the compound (XIV) may include an acid halide, an acid anhydride, an activated amide, an activated ester, and the like. The suitable example may be an acid chloride; an acid azide; a mixed acid anhydride with a acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, sulfonic acid (e.g. methanesulfonic acid, etc.), alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (XIV) to be used.

The reaction is usually carried out in a conventional solvent such as alcohol (e.g. methanol, ethanol, etc.), acetone, dioxane, acetonitrile, methylene chloride, ethylene chloride, tetrahydrofuran, N,N-dimethylformamide, pyridine or any other solvent which does not adversely influence the reaction. These conventional solvent may also be used in a mixture with water.

When the compound (XIV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene, trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)alkylbenzylamine, or the like. The reaction temperature is not critical and the reaction is usually carried out under cooling or at ambient temperature.

Process 5

The compound (Ie) or a salt thereof can be prepared by subjection the compound (Id) or a salt thereof to acylation reaction.

This reaction can be referred to those of Examples 2,4,5,7,8,17 and 18 described later.

Process 6

The compound (If) or a salt thereof can be prepared by subjecting the compound (Ia) or a salt thereof to hydrolysis reaction.

This hydrolysis reaction can be referred to that of the aforementioned Process 3.

Process 7

The compound (Ig) or a salt thereof can be prepared by subjecting the compound (If) or a salt thereof to esterification reaction. The esterifying agent to be used in this reaction may include a conventional one such as an alcohol or its reactive equivalent (e.g. halide, sulfonate, sulfate, diazo compound, etc.) or the like.

The reaction is usually carried out in a conventional solvent such as acetone, dioxane, alcohol, methylene chloride, ethylene chloride, n-hexane, tetrahydrofuran, ethyl acetate, N,N-dimethylformamide, or any other solvent which does not adversely influence the reaction.

The reaction temperature is not critical and the reaction is usually carried out under cooling to warming.

Process 8

The compound (Ii) or a salt thereof can be prepared by subjecting the compound (Ih) or a salt thereof to reduction.

The reduction method applicable for the present reaction may include catalytic reduction.

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reaction is usually carried out in a conventional solvent such as acetone, dioxane, alcohol, tetrahydrofuran, ethyl acetate, N,N-dimethylformamide, dimethyl sulfoxide or any other solvent which does not adversely influence the reaction.

The reaction temperature is not critical and the reaction is usually carried out under cooling to heating.

Process 9

The compound (Ij) or a salt thereof can be prepared by subjecting the compound (Id) or a salt thereof to alkylation reaction. This reaction can be referred to that of Example 19 described later.

Process A

The compound (II) or a salt thereof can be prepared by reacting the compound (IV) or a salt thereof in accordance with the synthetic scheme shown in Process A. Each reaction in the said scheme can be carried out by the conventional method for the peptide synthesis. The starting compound (IV) or a salt thereof can be prepared by the methods disclosed in the Preparations described later or similar manners thereto.

Process B

The compound (III) or a salt thereof can be prepared by reacting the compound (IX) or a salt thereof in accordance with the synthetic scheme shown in Process B. Each reaction in the said scheme can be carried out by the conventional method for the peptide synthesis. The starting compound (IX) or a salt thereof can be prepared by the methods disclosed in the Preparations described later or similar manners thereto.

Production by Fermentation

The WS-9326A and WS-9326B of this invention can be produced by fermentation of a WS-9326A and/or WS-9326B-producing strain belonging to the genus Streptomyces such as *Streptomyces violaceoniger* No. 9326 in a nutrient medium.

Particulars of microorganism used for the production of the WS-9326A and WS-9326B will be explained in the following.

THE MICROORGANISM

The microorganism which can be used for the production of the WS-9326A and WS-9326B is a WS-9326A and/or WS-9326B-producing strain belonging to the genus Streptomyces, among which *Streptomyces violaceoniger* No. 9326 has been newly isolated from a soil sample collected at Suwa City, Nagano Prefecture, Japan.

A lyophilized sample of the newly isolated *Streptomyces violaceoniger* No. 9326 has been deposited with the Fermentation Research Institute, Agency of Industrial Science and Technology (1-3, Higashi 1-chome, Tsukuba-shi, Ibaraki-ken 305, Japan) under the number of FERM BP-1667 (deposited date: Jan. 20, 1988).

It is to be understood that the production of the novel WS-9326A and WS-9326B is not limited to the use of the particular organism described herein, which is given for the illustrative purpose only. This invention also includes the use of any mutants which are capable of producing the WS-9326A and WS-9326B including natural mutants as well as artificial mutants which can be produced from the described organism by conventional means such as irradiation of X-rays, ultra-violet radiation, treatment with N-methyl-N'-nitro-N-nitrosoguanidine, 2-aminopurine, and the like.

The *Streptomyces violaceoniger* No. 9326 has the following morphological, cultural, biological and physiological characteristics.

[1] Morphological Characteristics

The methods described by Shirling and Gottlieb (Shirling, E. B. and D. Gottlieb: Methods for characterization of Streptomyces species. International Journal of Systematic Bacteriology, 16, 313-340, 1966) were employed for this taxonomic study.

Morphological observations were made with light and electron microscopes on cultures grown at 30° C for 14 days on oatmeal agar, yeast-malt extract agar and inorganic salts-starch agar.

The vegetative mycelium developed well without fragmentation. The aerial mycelium branched monopodially and formed spiral chains of spores with 10 to 30 spores per chain. The spores had a smooth surface and were oval in shape with a size of 0.6–0.8×0.8–1.3 μm. Sclerotic granules, sporangia and zoospores were not observed.

[2] Cultural Characteristics

Cultural characteristics were observed on ten kinds of media described by Shirling and Gottlieb as mentioned above, and by Waksman (Waksman, S. A.: The actinomycetes, Vol. 2: Classification, identification and description of genera and species. The williams and Wilkins Co., Baltimore, 1961).

The incubation was carried out at 30° C. for 21 days. The color names used in this study were taken from Methuen Handbook of Colour (Kornerup, A. and J. H. Wanscher: Methuen Handbook of Colour, Methuen, London, 1978). The results are shown in Table 1.

TABLE 1

| Cultural characteristics of strain No. 9326 | |
|---|---|
| Medium | Cultural characteristics |
| yeast-malt extract agar | G: good |
| | A: abundant, brownish gray (6E2) |
| | R: dark brown (7F6) |
| | S: none |
| oatmeal agar | G: good |
| | A: moderate, dark brown (7E3) |
| | R: brownish gray (7F2) |
| | S: none |
| inorganic salts-starch agar | G: good |
| | A: abundant, brownish gray (7E2) |
| | R: yellowish brown (5E6) |
| | S: none |
| glycerin-asparagine agar | G: good |
| | A: abundant, grayish violet (19E3) |
| | R: brown (6E4) |
| | S: none |
| peptone-yeast extract-iron agar | G: good |
| | A: thin, grayish white (1B1) |
| | R: yellowish brown (5D6) |
| | S: none |
| tyrosine agar | G: good |
| | A: abundant, brownish gray (9E2) |
| | R: brown (6E5) to black |
| | S: none |
| glucose-asparagine agar | G: good |
| | A: moderate, bluish gray (19E2) |
| | R: brown (6F4) |
| | S: none |
| nutrient agar | G: moderate |

TABLE 1-continued

| Cultural characteristics of strain No. 9326 | |
|---|---|
| Medium | Cultural characteristics |
| | A: moderate, brownish gray (9E2) |
| | R: grayish brown (5E3) to yellowish brown (5F4) |
| | S: none |
| Bennet agar | G: poor |
| | A: poor, dark brown (6F4) |
| | R: dark brown (6F4) |
| | S: none |
| sucrose-nitrate agar | G: poor |
| | A: none |
| | R: grayish brown (6E3) |
| | S: none |

Abbreviation: G = growth, A = aerial mycelium, R = reverse side color, S = soluble pigment The aerial mycelium was gray to brownish gray. Part of colony became black and moist, and showed hygroscopic character on most agar media. Reverse side of growth was yellowish brown, brown and dark brown. Reverse mycelium pigment was not pH sensitive. Melanoid pigments and other soluble pigments were not produced.

The cell wall analysis was performed by the methods of Becker et al. (Becker, B., M. P. Lechevalier, R. E. Gordon and H. A. Lechevalier: Rapid differentiation between Nocardia and Streptomyces by paper chromatography of whole cell hydrolysates: Appl. Microbiol., 12, 21-423, 1964) and Yamaguchi (Yamaguchi, T.: Comparison of the cell wall composition of morphologically distinct actinomycetes: J. Bacteriol., 89, 444-453, 1965). Analysis of whole cell hydrolysates of strain No. 9326 showed the presence of LL-diaminopimelic acid. Accordingly, the cell wall of this strain is believed to be of type I.

[3] Biological and Physiological Properties

Physiological properties and utilization of carbon sources are shown in Table 2 and 3, respectively.

Utilization of carbon sources was examined according to the methods of Pridham and Gottlieb (Pridham, T. G. and D. Gottlieb: The utilization of carbon compounds by some Actinomycetales as an aid for species determination: J. Bacteriol., 56, 107-114, 1948).

TABLE 2

| Physiological properties of strain No. 9326 | |
|---|---|
| Conditions | Characteristics |
| temperature range for growth | 11° C.–47° C. |
| optimum temperature range for growth | 29° C.–31° C. |
| gelatin liquefaction | positive |
| milk coagulation | negative |
| milk peptonization | positive |
| starch hydrolysis | positive |
| production of melanoid pigment | negative |
| decomposition of cellulose | negative |

TABLE 3

| Carbon utilization of strain No. 9326 | |
|---|---|
| Compounds | Growth |
| D-glucose | + |
| sucrose | + |
| D-xylose | + |
| D-fluctose | + |
| L-rhamnose | + |
| raffinose | + |
| L-arabinose | + |
| inositol | + |

TABLE 3-continued

| Carbon utilization of strain No. 9326 | |
|---|---|
| Compounds | Growth |
| mannitol | + |

+: utilization

The morphology and chemical characteristics of strain No. 9326 permitted a clear assignment of the organism to the genus Streptomyces. Strain No. 9326 was compared with Streptomyces species described in the 8th edition of Bergey's manual (Buchanan, R. E. and N. E. Gibbons: Bergey's manual of determinative bacteriology, eight edition. The Williams and Wilkins Co., Baltimore, 1974), Streptomyces species described in Shirling's ISP reports [(Shirling, E. B. and D. Gottlieb: Cooperative description of type culture of Streptomyces.2. Species descriptions from first study. Intern. J. Syst. Bacteriol. 18: 69-189, 1968), (Shirling, E. B. and D. Gottlieb: Cooperative description of type culture of Streptomyces.3. Additional species descriptions from first and second studies. Intern. J. Syst. Bacteriol. 18 : 279-392, 1968 and (Shirling, E. B. and D. Gottlieb: Cooperative description of type culture of Streptomyces.4. Species descriptions from the second, third and fourth studies. Intern. J. Syst. Bacteriol. 19: 391-512, 1969)], the species listed on "Approved lists of bacterial names" (Skerman, V. B. D.; V. McGowan & P. H. A. Sneath: Approved list of bacterial names. Intern. J. Syst. Bacteriol. 30: 225-420, 1980) and the species described in the other references [(Williams, S. T.: M. Goodfellow, G. Alderson, E. M. H. Wellington, P. H. A. Sneath and M. J. Sackin: Numerical classification of Streptomyces and related genera. J. Gen. Microbiol. 129: 1743-1813, 1983) and (Dietz, A.: Criteria for characterization of Hygroscopicus strains. In "Actinomycetes; The Boundary Microorganisms" pp 183-191 Edited by T. Arai, 1976)].

As a result, it was found that strain No. 9326 proved to closely resemble *Streptomyces violaceoniger*. Therefore, strain No. 9326 was identified as *Streptomyces violaceoniger* and designated *Streptomyces violaceoniger* No.9326.

PRODUCTION OF WS-9326A AND WS-9326B

The novel WS-9326A and WS-9326B of this invention can be produced by culturing a WS-9326A and/or WS-9326B-producing strain belonging to the genus Streptomyces (e.g. *Streptomyces violaceoniger* No.9326, FERM BP-1667) in a nutrient medium.

In general, the WS-9326A and WS-9326B can be produced by culturing the WS-9326A and/or WS-9326B-producing strain in an aqueous nutrient medium containing sources of assimilable carbon and nitrogen, preferable under aerobic conditions (e.g. shaking culture, submerged culture, etc.).

The preferred sources of carbon in the nutrient medium are carbohydrates such as glucose, xylose, galactose, glycerin, starch, dextrin, and the like.

Other sources which may be included are maltose, rhamnose, raffinose, arabinose, mannose, salicin, sodium succinate, and the like.

The preferred sources of nitrogen are yeast extract, peptone, gluten meal, cottonseed meal, soybean meal, corn steep liquor, dried yeast, wheat germ, feather meal, peanut powder etc., as well as inorganic and organic nitrogen compounds such as ammonium salts (e.g. ammonium nitrate, ammonium sulfate, ammonium phosphate, etc.), urea, amino acid, and the like.

The carbon and nitrogen sources, though advantageously employed in combination, need not be used in their pure form, because less pure materials which contain trace of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts and the like. If necessary, especially when the culture medium foams seriously, a defoaming agent such as liquid paraffin, fatty oil, plant oil, mineral oil or silicone may be added.

As the conditions for the production of the WS-9326A and WS-9326B in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of the WS-9326A and WS-9326B. Accordingly, it is desirable first to produce a vegetative inoculum of the organism by inoculating a relatively small quantity of culture medium with spores or mycelia of the organism and culturing said inoculated medium, and then to transfer the cultured vegetative inoculum aseptically to large tanks. The medium, in which the vegetative inoculum is produced, is substantially the same as or different from the medium utilized for the production of the WS-9326A and WS-9326B.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°-35° C., for a period of about 50 hours to 150 hours, which may be varied according to fermentation conditions and scales.

Thus produced WS-9326A and WS-9326B can be recovered from the culture medium by conventional means which are commonly used for the recovery of other known biologically active substances. The WS-9326A and WS-9326B produced are found in the cultured filtrate and mycelium, and accordingly the WS-9326A and WS-9326B can be isolated and purified from the filtrate and the mycelium, which are obtained by filtering or centrifuging the cultured broth, by a conventional method such as concentration under reduced pressure, lyophilization, extraction with a conventional solvent, pH adjustment, treatment with a conventional resin (e.g. anion or cation exchange resin, non-ionic adsorption resin, etc. , treatment with a conventional absorbent (e.g. activated charcoal, silicic acid, silica gel cellulose, alumina, etc.), crystallization, recrystallization, and the like.

BRIEF DESCRIPTION OF THE DRAWINGS

The Figures accompanying this specification show the following spectral data for WS-9326A, WS-9326B, and derivatives thereof.

The WS-9326A produced according to the aforementioned process possesses the following physical and chemical properties.

Figure 1:
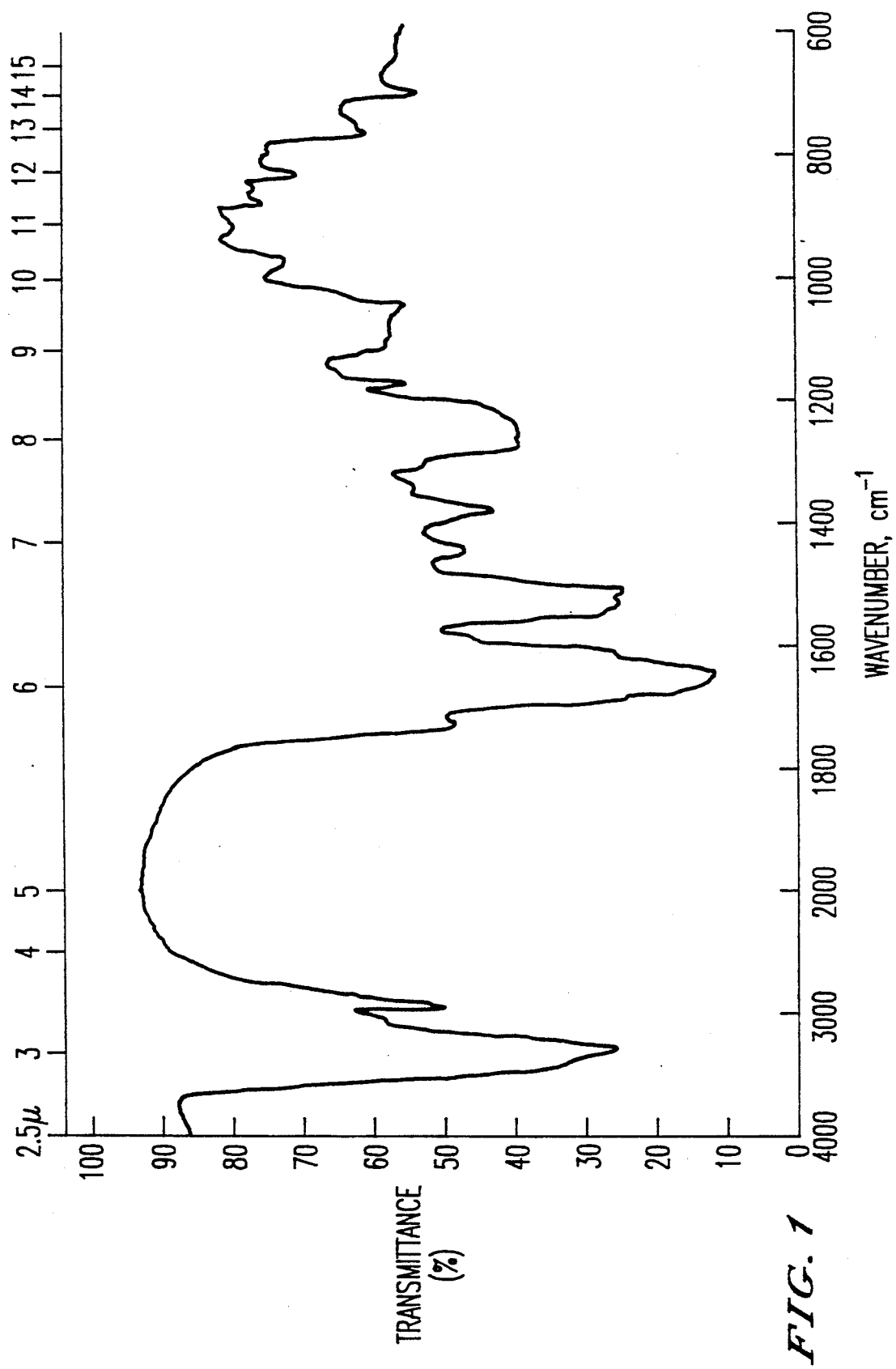
FIG. 1 represents the spectrum of infrared absorption of WS-9326A in KBr.

(1) Form and Color:
  colorless powder
(2) Color Reaction:
  Positive:  cerium sulfate reaction, iodine vapor reaction, ferric chloride-potassium ferricyanide reaction,
  Negative:  ninhydrine reaction, Molish reaction, ferric chloride reaction, Ehrlich reaction, Pauli reaction
(3) Solubility:
  Soluble:  methanol, ethanol
  Sparingly Soluble: acetone, ethyl acetate
  Insoluble:  water, chloroform
(4) Melting Point:  187–190° C.
(5) Specific Rotation:
  $[\alpha]_D^{23}$: −84° (C = 1.0, MeOH)
(6) Ultraviolet Absorption Spectrum:
  $\lambda_{max}^{MeOH}$ = 280 nm ($\epsilon$ = 34,700)
(7) Infrared Absorption Spectrum:
  $\nu_{max}^{KBr}$ = 3300, 3050, 2950, 2920, 2860, 1730, 1650, 1610, 1560, 1540, 1530, 1510, 1440, 1380, 1340, 1280, 1240, 1170, 1110, 1080, 1060, 1040, 970, 920, 880, 860, 830 cm$^{-1}$,
  the chart of which is shown in FIG. 1,
(8) Elemental Analysis (percentage by weight):
  Found: C 60.18, H 6.61, N 10.32,
  Calcd. for C$_{54}$H$_{68}$N$_8$O$_{13}$.2H$_2$O: C 60.43, H 6.76, N 10.44.
(9) Thin Layer Chromatography:

| Stationary phase | Developing solvent | Rf value |
|---|---|---|
| Silica gel plate (MERCK ART 5715) | chloroform-methanol (5:1, V/V) | 0.38 |
| RP-18 plate (available from Merck) | methanol-water (8:2, V/V) | 0.46 |

Figure 2:
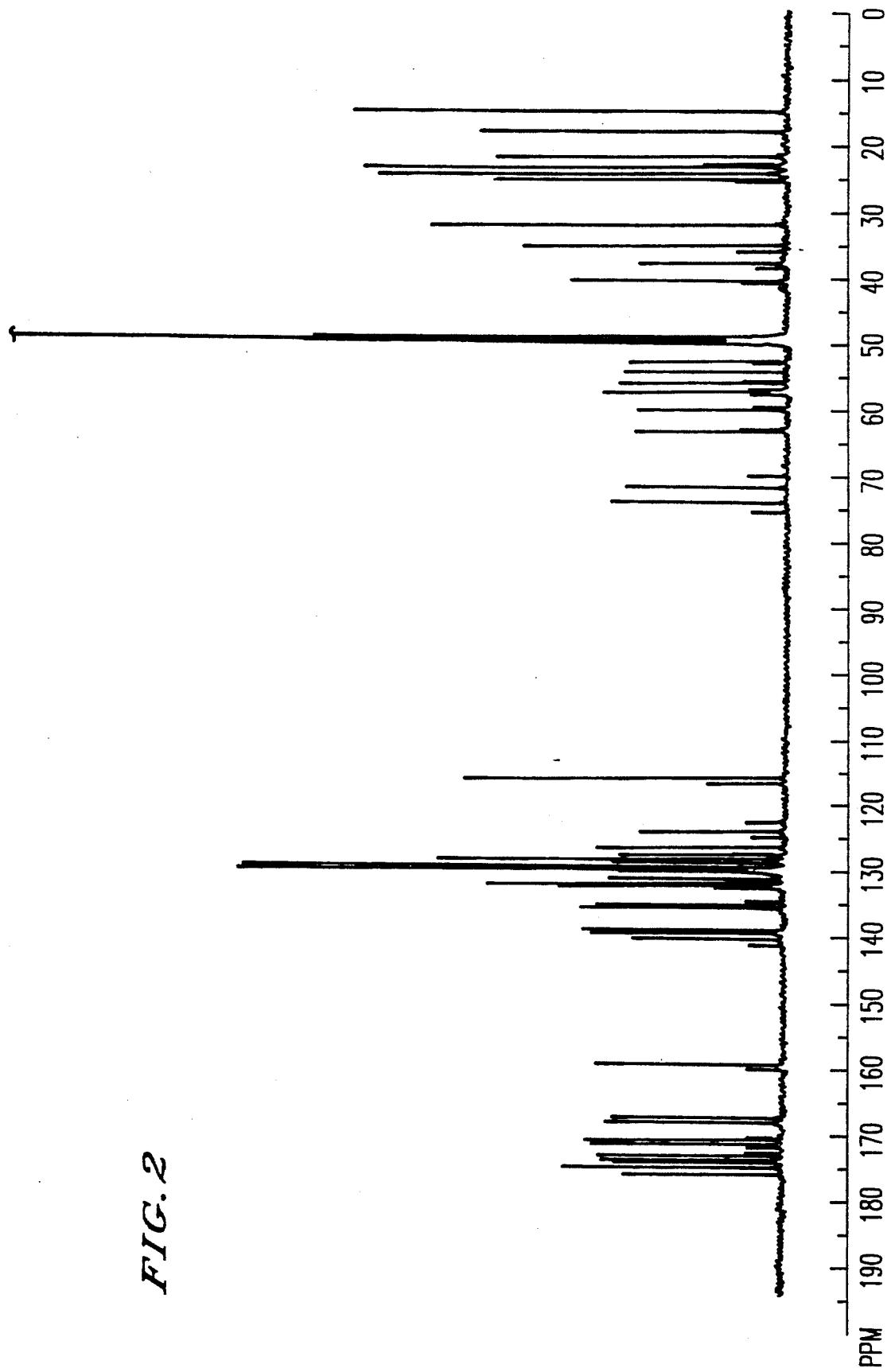
FIG. 2 represents the spectrum of $^{13}$C nuclear magnetic resonance of WS-9326A in CD$_3$OD.
Figure 3:
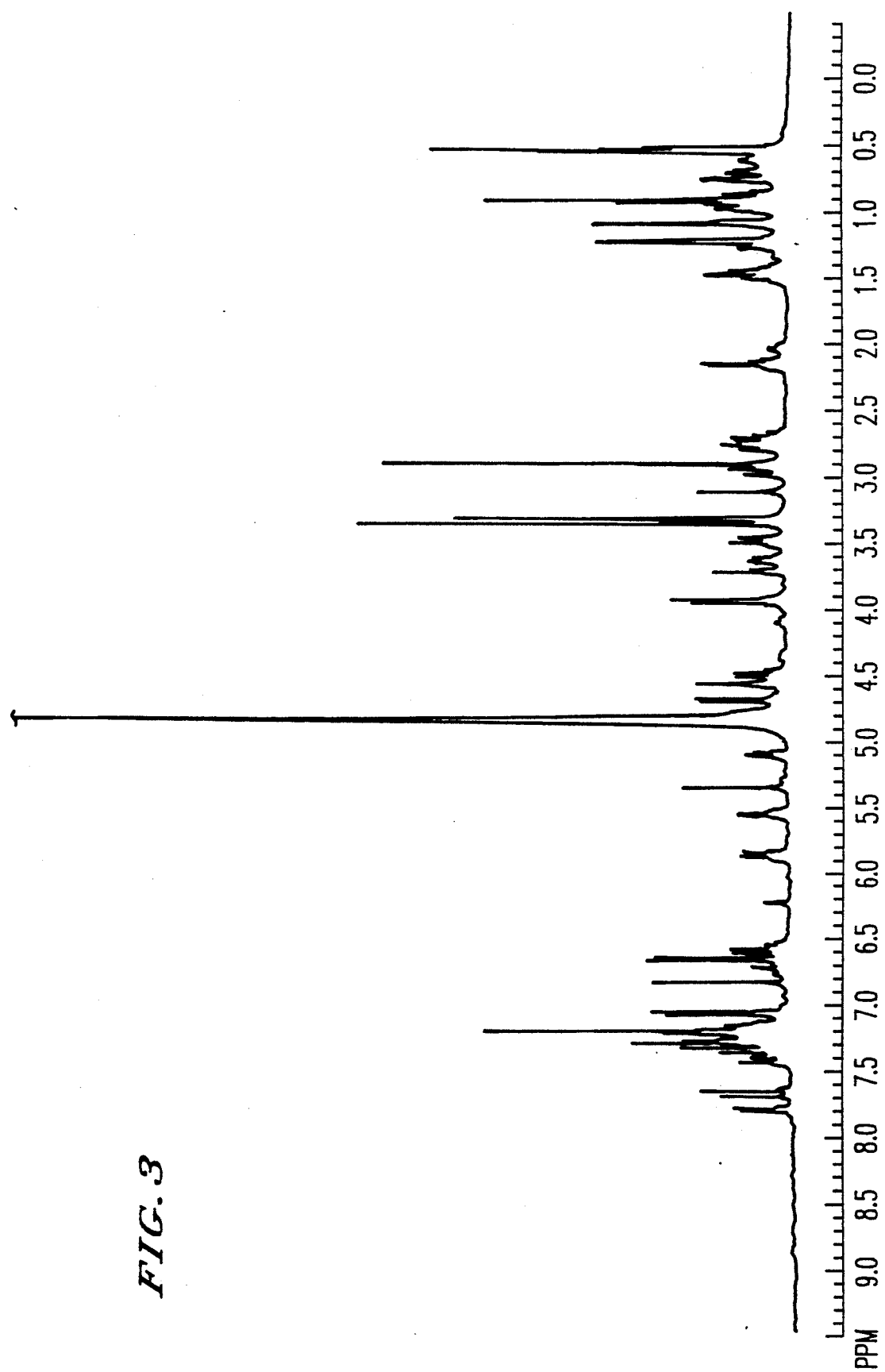
FIG. 3 represents the spectrum of $^1$H nuclear magnetic resonance of WS-9326A in CD$_3$OD.

(10) Molecular Formula: C$_{54}$H$_{68}$N$_8$O$_{13}$
(11) Molecular Weight:
  FAB-MS: m/z 1037 (M + H)$^+$
(12) Property of the Substance:
  acidic substance
(13) $^{13}$C Nuclear Magnetic Resonance Spectrum:
  (100 MHz, CD$_3$OD)  δ
  175.69 (s),   174.70 (s),
  173.73 (s),   173.38 (s),
  172.89 (s),   171.04 (s),
  170.45 (s),   167.79 (s),
  167.15 (s),   159.20 (s),
  140.05 (d),   139.12 (s),
  138.71 (s),   135.27 (d),
  134.85 (s),   132.11 (d),
  132.03 (s),   131.69 (d) × 2,
  130.70 (d),   129.90 (d),
  129.61 (d) × 2, 129.22 (d) × 2,
  128.55 (d),   128.04 (d),
  127.99 (d),   127.38 (d),
  126.09 (s),   123.70 (d),
  115.63 (d) × 2, 73.46 (d),
  71.34 (d),    62.80 (t),
  59.53 (d),    56.91 (d),
  56.76 (d),    55.55 (d),
  53.64 (d),    52.10 (d),
  39.85 (t),    37.18 (t),
  37.09 (t),    34.58 (q),
  31.37 (t),    24.56 (d),
  23.63 (t),    22.71 (q),
  22.52 (q),    21.17 (q),
  17.19 (q),    14.13 (q),
  the chart of which is shown in FIG. 2,
(14) $^1$H Nuclear Magnetic Resonance Spectrum:
  (400 MHz, CD$_3$OD)  δ
  7.80      (1H, d, J=8Hz),
  7.67      (1H, d, J=16Hz),
  7.45–7.14 (9H, m),
  7.06      (2H, d, J=8Hz),
  6.83      (1H, s),
  6.65      (2H, d, J=8Hz),
  6.59      (1H, d, J=12Hz),
  5.88      (1H, dt, J=12 and 7Hz),
  5.55      (1H, m),
  5.35      (1H, broad signal),
  5.10      (1H, dd, J=3 and 9.5Hz),
  4.68      (1H, d, J=10Hz),
  4.55      (1H, t, J=6Hz),
  4.48      (1H, dd, J=3 and 12Hz),
  3.92      (2H, d, J=6Hz),
  3.70      (1H, t, J=7.5Hz),
  3.62      (1H, m),
  3.46      (1H, dd, J=3 and 14Hz),
  2.94      (1H, dd, J=3 and 16Hz),
  2.89      (3H, s),
  2.74      (1H, dd, J=9.5 and 16Hz),
  2.69      (1H, dd, J=12 and 14Hz),
  2.14      (2H, m),
  1.5–1.4   (2H, m),
  1.20      (3H, d, J=6Hz),
  1.08      (3H, d, J=6Hz),
  1.0–0.8   (2H, m)
  0.91      (3H, t, J=7Hz),
  0.6       (1H, m),
  0.53      (3H, d, J=6Hz),
  0.51      (3H, d, J=6Hz),
  the chart of which is shown in FIG. 3,
(15) Amino-Acid Analysis:
  WS-9326A (5 mg) was hydrolyzed at 110° C. for 20 hours with hydrochloric acid (2 ml) in a sealed tube. The mixture was evaporated to dryness to give the hydrolysis products which were analyzed on a HITACHI 835 automatic amino-acid analyzer.
  The results of the amino acid analysis:
  Threonine(2), Leucine(1), Phenylalanine(1), Aspartic acid(1), Serine(1), methylamine(1) and ammonia(1)

With regard to the WS-9326A, it is to be noted that $^{13}$C and $^1$H Nuclear Magnetic Resonance Spectra shown in FIGS. 2 and 3 show that the WS-9326A exists in at least two stable conformations in CD$_3$OD solution and the chemical shifts described in the above (13) and (14) are those of the major conformer of WS-9326A.

The WS-9326B produced according to the aforementioned process possesses the following physical and chemical properties.

(1) Form and Color:  colorless amorphous powder (2) Color Reaction:
   Positive: cerium sulfate reaction, iodine vapor reaction
   Negative: ninhydrine reaction
(3) Solubility:
   Soluble: methanol
   Sparingly Soluble: ethanol
   Insoluble: water, acetone, ethyl acetate, chloroform
(4) Melting Point: 165–170° C. (dec.)
(5) Specific Rotation:
   $[\alpha]_D^{23}$: −64° (C = 1.0, MeOH)
(6) Ultraviolet Absorption Spectrum:
   $\lambda_{max}^{MeOH}$ = 283 nm ($\epsilon$ = 27,000)
(7) Molecular Formula: $C_{54}H_{70}N_8O_{13}$
(8) Elemental Analysis (percentage by weight):
   Found: C 59.97, H 6.87, N 10.29;
   Calcd. for $C_{54}H_{70}N_8O_{13}\cdot 2H_2O$: C 60.32, H 6.94, N 10.42.
(9) Molecular Weight:
   FAB-MS: m/z 1061.6 (M + Na)$^+$
(10) Thin Layer Chromatography:

| Stationary phase | Developing solvent | Rf value |
|---|---|---|
| Silica gel plate (MERCK ART 5715) | chloroform-methanol (5:1, V/V) | 0.38 |
| RP-18 plate | methanol-water (8:2, V/V) | 0.25 |

(11) Infrared Absorption Spectrum:
   $\nu_{max}^{KBr}$ = 3300, 3050, 2950, 1735, 1660, 1530, 1510, 1450, 1400, 1380, 1340, 1260, 1220, 1080, 980, 920 cm$^{-1}$
(12) $^{13}$C Nuclear Magnetic Resonance Spectrum:
   (100 MHz, CD$_3$OD) δ

Figure 6:
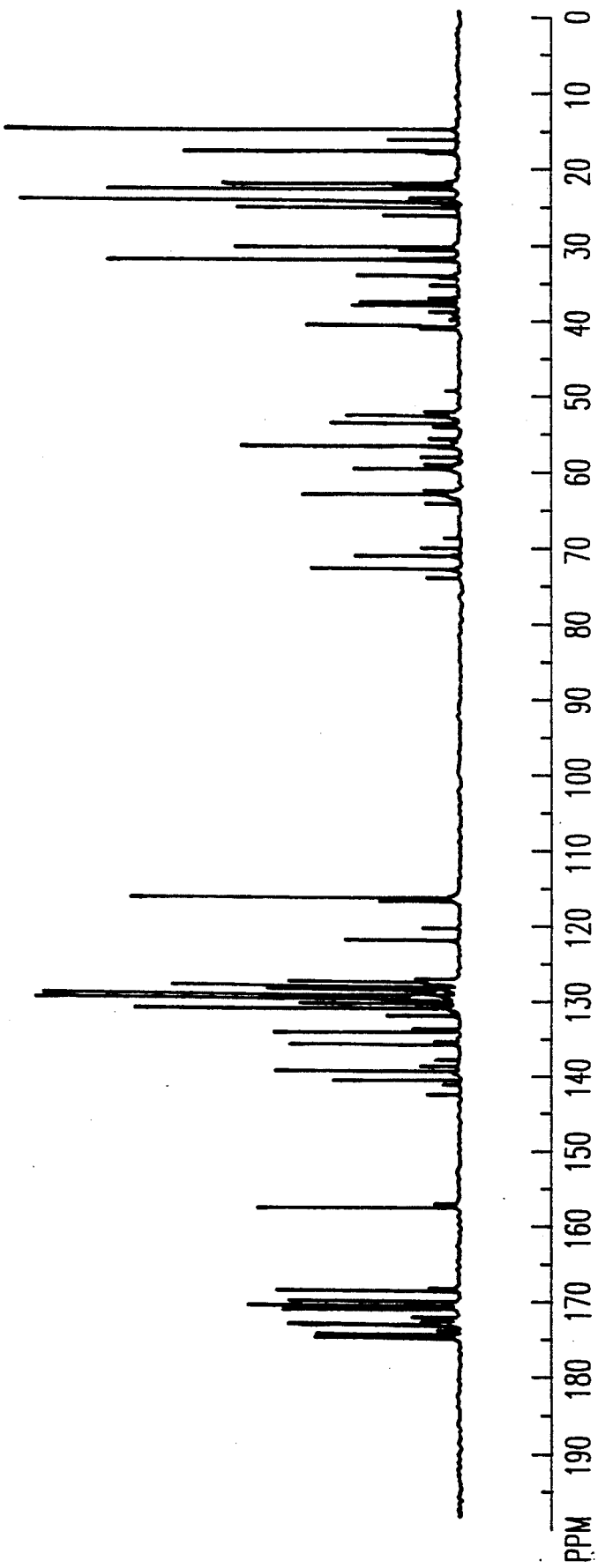
FIG. 6 represents the spectrum of $^{13}$C nuclear magnetic resonance of WS-9326B in CD$_3$OD.

| | |
|---|---|
| 174.99 (s), | 174.54 (s), |
| 173.60 (s), | 173.41 (s), |
| 173.30 (s), | 171.27 (s), |
| 170.74 (s), | 170.19 (s), |
| 168.69 (s), | 157.59 (s), |
| 140.53 (d), | 139.35 (s), |
| 139.18 (s), | 135.76 (d), |
| 134.17 (s), | 131.15 (d) × 2, |
| 130.93 (d), | 130.35 (d), |
| 129.88 (d) × 2, | 129.39 (d) × 2, |
| 128.70 (d), | 128.58 (s), |
| 128.13 (d), | 127.64 (d), |
| 127.53 (d), | 121.99 (d), |
| 116.45 (d) × 2, | 72.76 (d), |
| 70.82 (d), | 62.73 (t), |
| 62.67 (d), | 59.35 (d), |
| 56.33 (d) × 2, | 56.19 (d), |
| 53.36 (d), | 52.24 (d), |
| 40.24 (t), | 37.55 (t), |
| 37.08 (t), | 33.69 (t), |
| 31.57 (t), | 29.93 (q), |
| 24.61 (d), | 23.70 (q), |
| 23.59 (t), | 22.16 (q), |
| 21.36 (q), | 17.12 (q), |
| 14.23 (q), | | the chart of which is shown in FIG. 6,

(13) $^1$H Nuclear Magnetic Resonance Spectrum:
   (400 MHz, CD$_3$OD) δ

Figure 7:
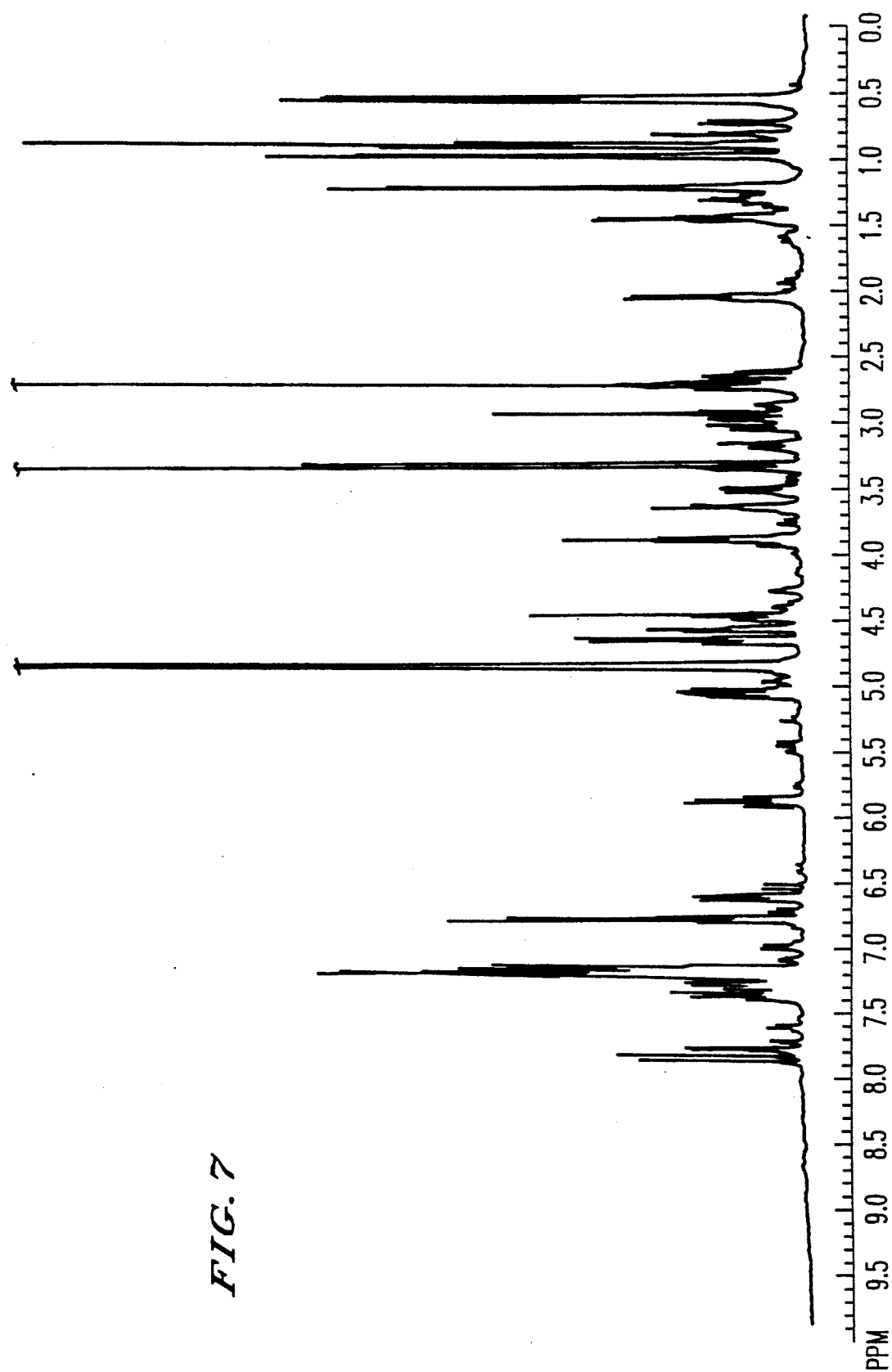
FIG. 7 represents the spectrum of $^1$H nuclear magnetic resonance of WS-9326B in CD$_3$OD.

| | |
|---|---|
| 7.86 | (1H, d, J=16Hz), |
| 7.80 | (1H, br d, J=8Hz), |
| 7.12–7.42 | (11H, m), |
| 6.77 | (2H, d, J=8.5Hz), |
| 6.61 | (1H, d, J=11.5Hz), |
| 5.88 | (1H, dt, J=7.5 and 11.5Hz), |
| 5.08 | (1H, dd, J=3.5 and 10Hz), |
| 5.04 | (1H, q, J=6.5Hz), |
| 4.66 | (1H, dd, J=3.5 and 13Hz), |
| 4.65 | (1H, d, J=11.5Hz), |
| 4.56 | (1H, dd, J=2.5 and 7Hz), |
| 4.48 | (1H, dd, J=4.5 and 11Hz), |
| 4.46 | (1H, s), |
| 3.88 | (2H, m), |
| 3.64 | (2H, m), |
| 3.51 | (1H, dd, J=3.5 and 14Hz), |
| 3.17 | (1H, dd, J=4.5 and 14Hz), |
| 3.01 | (1H, dd, J=11 and 14Hz), |
| 2.94 | (1H, dd, J=3.5 and 16Hz), |
| 2.71 | (3H, s), |
| 2.71 | (1H, dd, J=10 and 16Hz), |
| 2.64 | (1H, dd, J=13 and 14Hz), |
| 2.04 | (2H, m), |
| 1.43 | (2H, m), |
| 1.28 | (2H, m), |
| 1.20 | (3H, d, J=6Hz), |
| 0.95 | (3H, d, J=6.5Hz), |
| 0.87 | (3H, t, J=7.5Hz), |
| 0.53 | (1H, m), |
| 0.52 | (6H, d, J=10.5Hz), | the chart of which is shown in FIG. 7.

With regard to the WS-9326B, it is to be noted that $^{13}$C and $^1$H Nuclear Magnetic Resonance Spectra shown in FIGS. 6 and 7 show that the WS-9326B exists in at least two stable conformations in CD$_3$OD solution and the chemical shifts described in the above (12) and (13) are those of the major conformer of WS-9326B.

From the analysis of the above physical and chemical properties, and the result of further investigation for identification of chemical structure, the chemical structures of the WS-9326A and WS-9326B have been identified and assigned as follows.

WS-9326A

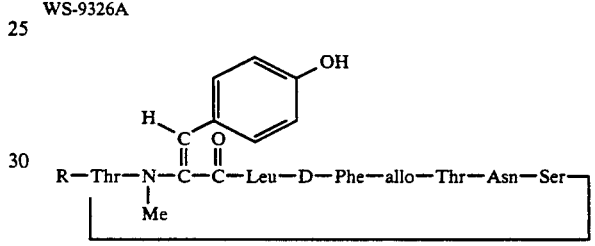

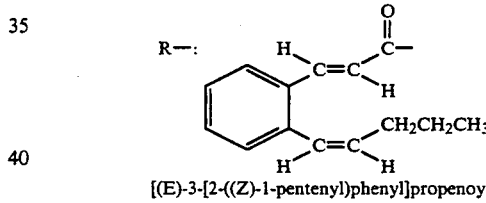

[(E)-3-[2-((Z)-1-pentenyl)phenyl]propenoyl]

WS-9326B

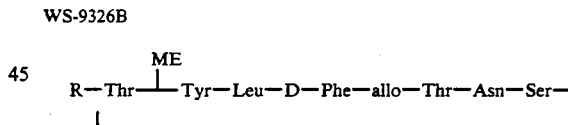

R—: (E)-3-[2-((Z)-1-pentenyl)phenyl]propenoyl

Suitable pharmaceutically acceptable salts of the object compound (I) are conventional non-toxic salts and may include a salt with a base or an acid addition salt such as a salt with an inorganic base, for example, an alkali metal salt (e.g. lithium salt, sodium salt, potassium salt, etc.), an alkaline earth metal salt (e.g. calcium salt, magnesium salt, etc.), an ammonium salt; a salt with an organic base, for example, an organic amine salt (e.g. triethylamine salt, pyridine salt, picoline salt, ethanolamine salt, triethanolamine salt, dicyclohexylamine salt, N,N'-dibenzylethylenediamine salt, etc.) etc.; an inorganic acid addition salt (e.g. hydrochloride, hydrobromide, sulfate, phosphate, etc.); an organic carboxylic or sulfonic acid addition salt (e.g. formate, acetate, trifluoroacetate, maleate, tartrate, methanesulfonate, benzenesulfonate, p-toluenesulfonate, etc.); a salt with a basic or acidic amino acid (e.g. arginine, aspartic acid, glutamic acid, etc.) and the like.

Suitable salts of the compounds (Ia)-(Ij), (II) and (III) can be referred to the ones as exemplified for the compound (I).

In the above and subsequent description of the present specification, suitable examples and illustration of the various definitions which the present invention include within the scope thereof are explained in detail as follows.

The term "lower" is intended to mean 1 to 6 carbon atom(s), unless otherwise indicated.

The term "higher" is intended to mean 7 to 20 carbon atoms, unless otherwise indicated. Suitable "acyl" and "acyl" moiety in the term "acyloxy" may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Alliphatic acyl such as lower or higher alkanoyl (e.g. formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, etc.); lower or higher alkoxycarbonyl (e.g. methoxycarbonyl, ethoxycarbonyl, t-butoxycarbonyl, t-pentyloxycarbonyl, heptyloxycarbonyl, etc.); lower or higher alkanesulfonyl (e.g. methanesulfonyl, ethanesulfonyl, etc.); lower or higher alkoxysulfonyl (e.g. methoxysulfonyl, ethoxysulfonyl, etc.); or the like;

Aromatic acyl such as aroyl (e.g. benzoyl, toluoyl, naphthoyl, etc.);

ar(lower)alkanoyl [e.g. phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g. naphthylacetyl, naphthylpropanoyl, naphthylbutanoyl, etc.), etc.];

ar(lower)alkenoyl [e.g. phenyl(lower)alkenoyl (e.g. phenylpropenoyl, phenylbutenoyl, phenylmethacryloyl, phenylpentenoyl, phenylhexenoyl, etc.), naphthyl(lower)alkenoyl (e.g. naphthylpropenoyl, naphthylbutenoyl, naphthylpentenoyl, etc.), etc.];

ar(lower)alkoxycarbonyl [e.g. phenyl(lower)alkoxycarbonyl (e.g. benzyloxycarbonyl, etc.), etc.]; aryloxycarbonyl (e.g. phenoxycarbonyl, naphthyloxycarbonyl, etc.); aryloxy(lower)alkanoyl (e.g. phenoxyacetyl, phenoxypropionyl, etc.); arylglyoxyloyl (e.g. phenylglyoxyloyl, naphthylglyoxyloyl, etc.); arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.); heterocyclic (lower)alkanoyl (e.g. thienylacetyl, thienylpropanoyl, thienylbutanoyl, thienylpentanoyl, thienylhexanoyl, thiazolylacetyl, thiadiazolylacetyl, tetrazolylacetyl, etc.); heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like. And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3,-triazolyl, etc.), tetrazolyl (e.g. 1H-tetrazolyl, 2H-tetrazolyl, etc.), etc.; saturated 3 to 8-membered (more preferably 5 or 6membered)-heteromonocyclic group containing 1 to 4 nitrogen atom(s), for example pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered (more preferably 5 or 6-membered)heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.; saturated 3 to 8-membered (more preferably 5 or 6-membered)heteromonocyclic group containing 1 to 2 oxygen atom(s) and 1 to 3 nitrogen atom(s), for example, morpholinyl, sydnonyl, etc.; unsaturated condensed heterocyclic group containing 1 to 2 oxygen atom(s) and 1 to 3 nitrogen atom(s), for example, benzoxazolyl, benzoxadiazolyl, etc.; unsaturated 3 to 8-membered (more preferably 5 or 6-membered)heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.; saturated 3 to 8-membered (more preferably 5 or 6-membered) heteromonocyclic group containing 1 to 2 sulfur atom(s) and 1 to 3 nitrogen atom(s), for example, thiazolidinyl, etc.; unsaturated 3 to 8-membered (more preferably 5 or 6membered) heteromonocyclic group containing 1 to 2 sulfur atom(s), for example, thienyl, dihydrodithiinyl, dihydrodithionyl, etc.; unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6membered) heteromonocyclic group containing an oxygen atom, for example, furyl, etc.; unsaturated 3 to 8-membered (more preferably 5 or 6-membered) heteromonocyclic group containing an oxygen atom and 1 to 2 sulfur atom(s), for example, dihydrooxathiinyl, etc.; unsaturated condensed heterocyclic group containing 1 to 2 sulfur atom(s), for example, benzothienyl, benzodithiinyl, etc.; unsaturated condensed heterocyclic group containing an oxygen atom and 1 to 2 sulfur atom(s), for example, benzoxathiinyl, etc. and the like.

The acyl moiety as stated above may have one to ten, same or different, suitable substituent(s) such as lower alkyl (e.g. methyl, ethyl, propyl, isopropyl, butyl, isobutyl, t-butyl, pentyl, hexyl, etc.); lower alkenyl (e.g. vinyl, allyl, 1-propenyl, 1 or 2 or 3-butenyl, 1 or 2 or 3 or 4-pentenyl, 1 or 2 or 3 or 4 or 5-hexenyl, etc.); lower alkoxy (e.g. methoxy, ethoxy, propoxy, etc.); lower alkylthio (e.g. methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl; etc.); halogen; amino; protected amino; hydroxy; protected hydroxy; cyano; nitro; carboxy; protected carboxy; sulfo; sulfamoyl; imino; oxo; amino(lower)alkyl (e.g. aminomethyl, aminoethyl, etc.); carbamoyloxy; hydroxy(lower)alkyl (e.g. hydroxymethyl, 1 or 2-hydroxyethyl, 1 or 2 or 3-hydroxypropyl, etc.); cyano(lower)alkenylthio (e.g. cyanovinylthio, etc.); or the like.

Suitable "hydroxy protective group" in the term "protected hydroxy" may include phenyl(lower)alkyl (e.g. benzyl, etc.), acyl as mentioned above, and the like.

Suitable "protected carboxy" may include esterified carboxy.

Suitable example of the ester moiety of an esterified carboxy may be the ones such as lower alkyl ester (e.g. methyl ester, ethyl ester, propyl ester, isopropyl ester, butyl ester, isobutyl ester, tertbutyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethylbutyryloxymethyl ester, 3,3-dimethylbutyryloxymethyl ester, 1(or 2)-pentanoyloxyethyl ester, etc.], lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc.), phthalidylidene(lower)alkyl ester, or (5-lower alkyl 2-oxo-1,3-dioxol-4-yl)(lower)alkyl ester [e.g. (5 methyl-2-oxo-1,3-dioxol-4-yl)methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, etc.); lower alkynyl ester (e.g. ethynyl ester, propynyl ester, etc.); ar(lower)alkyl ester which may have at least one suitable substituent(s) such as mono(or di or tri)phenyl(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tertbutylbenzyl ester, etc.); aryl ester which may have at least one suitable substituent(s) (e.g. phenyl ester, 4-chlorophenyl ester, tolyl ester, tertbutylphenyl ester, xylyl ester, mesityl ester, cumenyl ester, etc.); phthalidyl ester; and the like.

Suitable "lower alkoxy" may include methoxy, ethoxy, propoxy, isopropoxy, butoxy, isobutoxy, t-butoxy, pentyloxy, hexyloxy and the like.

Suitable "amino protective group" in the term "protected amino" may include acyl as mentioned above, and the like.

Suitable "ar(lower)alkenoyl" in the term "ar(lower)alkenoyl substituted with a lower alkenyl group" may include phenyl(lower)alkenoyl (e.g. phenylpropenoyl, phenylbutenoyl, phenylmethacryloyl, phenylpentenoyl, phenylhexenoyl, etc.), naphthyl(lower)alkenoyl (e.g. naphthylpropenoyl, naphthylbutenoyl, naphthylpentenoyl, etc.) and the like.

Suitable "lower alkenyl" in the term "ar(lower)alkenoyl substituted with a lower alkenyl group" may include vinyl, allyl, 1-propenyl, 1 or 2 or 3-butenyl, 1 or 2 or 3 or 4-pentenyl, 1 or 2 or 3 or 4 or 5-hexenyl and the like.

Suitable "ar(lower)alkanoyl" in the term "ar(lower)alkenoyl substituted with a lower alkyl group" may include phenyl(lower)alkanoyl (e.g. phenylacetyl, phenylpropanoyl, phenylbutanoyl, phenylisobutylyl, phenylpentanoyl, phenylhexanoyl, etc.), naphthyl(lower)alkanoyl (e.g..naphthylacetyl, naphthylpropanoyl, naphthylbutanoyl, etc.) and the like. Suitable "lower alkyl" in the term "ar(lower)alkanoyl substituted with a lower alkyl group" may include methyl, ethyl, propyl, isopropyl, butyl, isobutyl, t-butyl, pentyl, hexyl and the like.

Preferable embodiments of the object compound (I) are as follows.

$R^1$ is hydrogen, ar(lower)alkoxycarbonyl (more preferably phenyl(lower)alkoxycarbonyl), lower alkanoyl, higher alkanoyl (more preferably $C_{15}$–$C_{20}$ alkanoyl), aroyl (more preferably benzoyl), heterocyclic(lower)alkanoyl (more preferably thienyl(lower)alkanoyl), ar(lower)alkenoyl substituted with a lower alkenyl group (more preferably phenyl(lower)alkenoyl substituted with a lower alkenyl group), or ar(lower)alkanoyl substituted with a lower alkyl group (more preferably phenyl(lower)alkanoyl substituted with a lower alkyl group);

$R^2$ is hydroxy and $R^3$ is carboxy or esterified carboxy (more preferably lower alkoxycarbonyl), or $R^2$ and $R^3$ are linked together to represent a group of the formula:

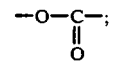

$R^4$ is hydroxy, ar(lower)alkoxy (more preferably phenyl(lower)alkoxy) or acyloxy (more preferably lower alkanoyloxy);

$R^5$ is hydroxy, ar(lower)alkoxy (more preferably phenyl(lower)alkoxy) or acyloxy (more preferably lower alkanoyloxy);

$R^6$ is hydroxy, lower alkoxy, ar(lower)alkoxy (more preferably phenyl(lower)alkoxy) or acyloxy (more preferably lower alkanoyloxy); and $==$ is a single bond or a double bond.

BIOLOGICAL PROPERTIES OF THE PEPTIDE DERIVATIVES

The peptide derivatives (I) and pharmaceutically acceptable salts thereof possess pharmacological activities such as substance P antagonism, neurokinin A (substance K) antagonism, analgesic action or the like, and therefore are useful for the treatment and prevention of asthma, various pains and the like.

As an example for showing such pharmacological activity, some pharmacological test data are illustrated in the following.

(1) Radioligand Binding Assay (a) Crude Membrane Preparation

Brain

Female Wister rats (200 g) were used and all reagents were purchased from Sigma Chemical Company. Whole brains (4 g) were minced into small pieces, and homogenized in 8 volumes of ice cold Medium I (50 mM Tris-HCl pH 7.5, 5 mM $MnCl_2$, 0.02% BSA, 2 µg/ml chymostatin, 4 µg/ml leupeptin and 40 µg/ml bacitracin) with a Ultra-Disperser (YAMATO MODEL LK-21). The homogenate was either stored at −20° C. or used in binding experiments immediately.

Lung

Male albino Hartley strain guinea pigs (600 g) were sacrificed by decapitation. The trachea and lungs were removed, and stored at −80° C. until use. These tissues (150 g) were thawed and homogenized in 500 ml buffer (0.25M sucrose, 50 mM Tris-HCl pH 7.5, 0.1 mM EDTA) with a compact mixer (MATSUDEN MJ-761). The tissue was homogenized with a Ultra-Disperser (YAMATO, MODEL LK-21) at a setting of maximum range for 10-s at 10-s intervals with cooling between homogenizations (total homogenization's time: 60 seconds). The homogenate was centrifuged (900×g for 10 min.) to remove tissue supernatant centrifuged at 14000×g for 20 min. to yield pellets which were referred to as crude membrane fractions. The pellets were resuspended in Medium I, homogenized with a teflon homogenizer and centrifuged at 14000×g for 20 min. The pellets were stored at −20° C.

(b) $^3$H-Substance P Binding to Preparative Membranes $^3$H-Substance P (1 nM, New England Nuclear) was incubated with 50 μl of the membrane preparation in medium I at 4° C. for 30 minutes in a final volume of 250 μl. At the end of the incubation period, its contents were quickly filtered over a whatmann GF/B glass fibre filter (pretreated with 0.1% polyethyleneimine for 3 hours prior to use) using cell harvester (BRANDEL M-24S). The filters were then washed ten times with a total of 3 ml of the washing buffer (50 mM Tris-HCl pH 7.5) at 0° C. The radioactivity was counted in 3 ml of Aquazol-2 in Packard sintillation counter (PACKARD TRI-CARB 4530).

TABLE 4

WS-9326A, WS-9326B, triacetyl-WS-9326A or tetrahydro-WS-9326A displacement of specific [$^3$H] substance P binding to rat brain and guinea pig lung membranes.

| | IC$_{50}$(M) | |
| --- | --- | --- |
| | brain | lung |
| WS-9326A | $2.5 \times 10^{-5}$ | $3.8 \times 10^{-6}$ |
| Triacetyl-WS-9326A | $9.4 \times 10^{-5}$ | $7.7 \times 10^{-5}$ |
| WS-9326B | | $8.8 \times 10^{-5}$ |
| Tetrahydro-WS-9326A | | $4.2 \times 10^{-7}$ |

(2) Effect of WS-9326A or Tetrahydro-WS-9326.A on Guinea Pig Trachea

Tracheal spiral strips were prepared from adult, male, albino Hartley strain guinea pigs (600 g) according to standard technique and placed in jacketed 30 ml glass tissue bath. The tension of tracheal strips was measured isometrically by means of force displacement transducer coupled to a polygraph (BIOPHYSIOGRAPH 180 system, San-Ei Instrument). Tracheal strips (2 mm width and 50 mm length) were suspended under a resting tension of 500 mg in 30 ml organ baths containing warm (37° C.) oxygenated (95% $O_2$: 5% $CO_2$) Tyrode solution of following composition: NaCl 137 mM (8 g/liter), KCl 2.7 mM (0.2 g/liter), CaCl$_2$·2H$_2$O 1.8 mM (0.264 g/liter), MgCl$_2$·6H$_2$O 1.02mM (0.208 g/liter), NaHCO$_3$ 11.9 mM (1 g/liter), NaH$_2$PO$_4$·2H$_2$O 0.42 mM (0.066 g/liter) and glucose 5.5 mM (1 g/liter). The tissues were equilibrated for 90 minutes and then WS-9326A or tetrahydro-WS-9326A was tested against various bronchoconstrictor (substance P $10^{-8}$M and neurokinin A $10^{-9}$M). The tension was recorded with a SAN-EI RECTIGRAPH-8S recorder (San-Ei Instrument).

TABLE 5

Effect of WS-9326A or tetrahydro-WS-9326A on the contractile responses of guinea pig trachea induced by neurokinin A (NKA) and substance P (SP).

| WS-9326A | Inhibition % | |
| --- | --- | --- |
| (μg/ml) | NKA$10^{-9}$M | SP $10^{-8}$M |
| 3 | 44% | −10% |
| 10 | 79% | 50% |
| 30 | 100% | 63% |
| WS-9326A IC$_{50}$(M) | $3.5 \times 10^{-6}$ | $9.7 \times 10^{-6}$ |
| Tetrahydro-WS-9326A IC$_{50}$(M) | $1.6 \times 10^6$ | $3.1 \times 10^{-6}$ |

(3) Effect of WS-9326A or Tetrahydro-WS-9326A on the Bronchoconstriction Induced by Neurokinin A and Capsaicin Male Hartley strain guinea-pigs weighing 300–500 g were immobilized with sodium pentobarbital (10 mg/animal administered intraperitoneally). The jugular vein was cannulated for administration of neurokinin A (or capsaicin) and drug. A catheter was also intubated into trachea for artifical ventilation. The animal was respirated by means of a miniature respiration pump (HARVARD B-34, 5 ml/stroke, 60 strokes/minute). Resistance to lung inflation was measured by a modification of Konzett-Rössler overflow technique.

Agonist was administered iv and the antagonist drug (prepared in 0.1% methyl cellulose-saline) was administered iv as shown below.

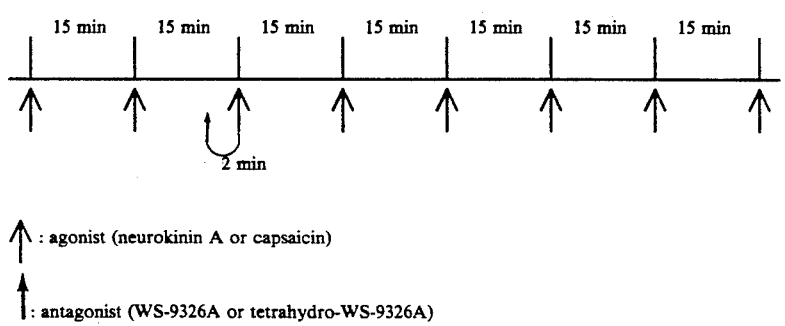

↑ : agonist (neurokinin A or capsaicin)

↑ : antagonist (WS-9326A or tetrahydro-WS-9326A)

TABLE 6

Inhibition of neurokinin A induced bronchoconstriction by WS-9326A or tetrahydro-WS-9326A
n:5

| Dose | Inhibition (%) of neurokinin A (1 n mol/kg, iv) response | | | | |
|---|---|---|---|---|---|
|  | 2 minutes | 17 minutes | 32 minutes | 47 minutes | 62 minutes |
| WS-9326A 10 mg/kg, iv | −16.5 ± 5.6 | 30.2 ± 12.9 | 45.8 ± 13.8 | 55.4 ± 8.1 | 49.9 ± 13.4 |
| Tetrahydro-WS-9326A 10 mg/kg, iv | 41.0 ± 5.6 | 100.0 ± 0.0 | 99.2 ± 0.8 | 98.4 ± 1.6 | 100.0 ± 0.0 |

TABLE 7

Inhibition of capsaicin induced bronchoconstriction by WS-9326A
n:4

| Dose | Inhibition (%) of capsaicin (10 n mol/kg, iv) response | | | | |
|---|---|---|---|---|---|
|  | 2 minutes | 17 minutes | 32 minutes | 47 minutes | 62 minutes |
| 10 mg/kg, iv | 16.6 ± 5.1 | 40.6 ± 12.2 | 51.2 ± 10.4 | 37.2 ± 19.7 | 47.1 ± 16.7 |

(4) Effect of Intratrachea Administration of WS-9326A or Tetrahydro-WS-9326A on Neurokinin A Induced Bronchoconstriction in Guinea-Pigs In order to test the effect of inhalation of WS-9326A or tetrahydro-WS-9326A on the bronchoconstriction. WS-9326A or tetrahydro-WS-9326A was dissolved in DMSO and administered intratrachea. The method was almost same as mentioned above.

As shown in Tables 8 and 9, WS-9326A and tetrahydro-WS-9326A were highly potent.

TABLE 8

Inhibition of neurokinin A induced bronchoconstriction by intratrachea administration of WS-9326A.

| Dose* | Inhibition (%) of neurokinin A** response | | | | |
|---|---|---|---|---|---|
|  | 20 minutes | 35 minutes | 50 minutes | 65 minutes | n |
| 0.03 mg/kg | 32.3 | 28.4 | 35.6 | 35.5 | 4 |
| 0.3 | 50.6 | 42.4 | 44.9 | 42.0 | 4 |
| 3 | 73.4 | 79.4 | 81.7 | 77.7 | 4 |
| $ED_{50}$ mg/kg | 0.23 | 0.29 | 0.19 | 0.24 |  |

*WS-9326A was dissolved in DMSO
**1 n mol/kg iv

TABLE 9

Inhibition of neurokinin A induced bronchoconstriction by intratrachea administration of Tetrahydro-WS-9326A.

| Dose* | Inhibition (%) of neurokinin A** response | | | | |
|---|---|---|---|---|---|
|  | 20 minutes | 35 minutes | 50 minutes | 65 minutes | n |
| 0.003 mg/kg | 5.4 | 23.5 | 17.2 | 12.6 | 4 |
| 0.03 | 50.0 | 50.9 | 51.4 | 43.0 | 4 |
| 0.3 | 77.7 | 75.7 | 74.6 | 71.1 | 4 |
| $ED_{50}$ mg/kg | 0.048 | 0.030 | 0.037 | 0.059 |  |

*Tetrahydro-WS-9326A was dissolved in DMSO
**1 n mol/kg iv (5) Acute Toxicity

Acute toxicity of WS-9326A was determined in ddY mice (5 weeks old, male) by a single intraperitoneal injection of graded dose of test compound into 5 mice. The LD50 value of WS-9326A was above 250 mg/kg and below 500 mg/kg (500 mg/kg > LD50 > 250 mg/kg).

(6) Analgesic Action

Acetic Acid Induced Writhing (i) Test Method:

Ten male ddY strain mice were used par group. To estimate the frequency of writhing syndrome, the animals were observed from 3 to 13 minutes after an intraperitoneal injection of 0.2 ml/10 g of 0.6% acetic acid. The drug(tetrahydro-WS-9326A) was given intraperitoneally 15 minutes before the injection of acetic acid. The frequency of writhing syndrome in the treated animals was compared with that in the non-treated control animals.

(ii) Test Result:
$ED_{50}$: 5.5 mg/kg

The pharmaceutical composition of this invention can be used in the form of a pharmaceutical preparation, for example, in solid, semisolid or liquid form, which contains the peptide derivatives(I) or pharmaceutically acceptable salts thereof, as an active ingredient, in admixture with an organic or inorganic carrier or excipient suitable for external, enteral or parenteral applications. The active ingredient may be compounded, for example, with the usual non-toxic, pharmaceutically acceptable carriers for tablets, pellets, capsules, inhalation, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid or liquid form, and in addition auxiliary, stabilizing, thickening and coloring agents and perfumes may be used. The active object compound is included in the pharmaceutical composition in an amount sufficient to produce the desired effect upon the process or condition of diseases.

While the dosage of therapeutically effective amount of the peptide derivatives (I) or pharmaceutically acceptable salts thereof varies from and also depends upon the age and condition of each individual patient to be treated, a daily dose of about 0.01–1000 mg, preferably 0.1–500 mg and more preferably 0.5–100 mg, of the active ingredient is generally given for treating diseases, and an average single dose of about 0.5 mg, 1 mg, 5 mg, 10 mg, 50 mg, 100 mg, 250 mg and 500 mg is generally administered.

In this specification, the amino acids, peptides, protective groups, etc. are indicated by the abbreviations according to the IUPAC-IUB (Commission on Biological Nomenclature) which are in common use in the filed on art.

Moreover, in the following Examples and Preparations, there are employed the other abbreviations in addition to the abbreviations adopted by the IUPAC-IUB.

The abbreviations used in this specification are as follows.

| | |
|---|---|
| Thr | L-threonine |
| Ser | L-serine |
| Tyr | L-tyrosine |
| Asn | L-asparagine |
| allo-Thr | L-allothreonine |
| D-Phe | D-phenylalanine |
| Leu | L-leucine |
| Z | benzyloxycarbonyl |
| Pac | phenacyl |
| Bzl | benzyl |
| Boc | t-butoxycarbonyl |
| Me | methyl |
| Tce | 2,2,2-trichloroethyl |
| Mmp | 4-methoxymethoxyphenyl |
| $Si^t$ | t-butyldimethylsilyl |
| Ac | acetyl |
| Et | ethyl |
| n-Hex | n-hexane |

The following Examples and Preparations are given for purpose of illustrating the present invention in detail.

EXAMPLE 1

Fermentation

An aqueous seed medium (160 ml) containing soluble starch (1%), sucrose (1%), glucose (1%), cotton seed flour (1%), eptone (0.5%), soybean meal (0.5%) and calcium carbonate (0.2%) (pH was adjusted to 7.0 with 6N of sodium hydroxide) was poured into each of twenty 500 ml Erlenmeyer flasks and sterilized at 120° C. for 30 minutes.

A loopful of slant culture of *Streptomyces violaceoniger* No. 9326 was inoculated to each of the media and cultured on a rotary shaker (220 rpm, 5.1 cm throw) at 30° C. for 3 days. The resultant seed culture was inoculated to 160 liter of sterile fermentation medium consisting of glycerin (3%), soybean meal (0.5%), ground soybean powder (1.5%), calcium carbonate (0.2%) and sodium iodide (NaI) (0.001%) in 200-liter stainless steel jar-fermentor. The fermentation was carried out at 30° C. for 3 days under aeration of 160 liters/minute and agitation of 200 rpm. An amount of WS-9326A in the fermentation broth was quantified by high performance liquid chromatography (HPLC) using HITACHI MODEL 655 pump. A steel column (4.6 mm inside diameter, 250 mm length) packed with an R-ODS-5 (YMC-PACKED COLUMN) was used at a flow rate of 1.0 ml/minute. Mobile phase used was a mixture of methanol and water (8:2). The sample for the HPLC assay was prepared as follows; an equal volume of acetone was added to a broth with vigorous stirring and stand for 1 hr and then centrifuged. The 5 μl of supernatant was injected to HITACHI MODEL 655 sample injector.

Isolation and Purification

An equal volume of acetone was added to the culture broth (150 l) with stirring. The mixture was allowed to stand at room temperature for one hour and then filtered. The filtrate was concentrated to 80 liter under reduced pressure, and was adjusted to pH 7.0 with 1N hydrochloric acid, and then extracted with 80 liter of ethyl acetate. The extract was concentrated to dryness under reduced pressure and applied to a column of silica gel (KIESELGEL 60, 70–230 mesh, available from Merck, 3 l). The column was washed with n-hexane (10 l), n-hexane-ethyl acetate [1:1 (10 l), ethyl acetate 20 , and active substance was eluted from the column with acetone (6 l). The active fractions were dried under reduced pressure, and was subjected to a column chromatography on silica gel (KIESELGEL 60, 70–230 mesh, available from Merck, 1.2 l). The column was washed with chloroform-methanol [20:1] (5 l), and the object substance was eluted with a solution of chloroform-methanol [10:1] (6 l). The fraction was dried under reduced pressure to give a powder. The powder was dissolved in a small volume of methanol and applied to a column of NS gel (Nihon Seimitsu, 500 ml). The object substance was eluted with methanol-water 8:2] (2 l) and concentrated to 300 ml under reduced pressure, and then extracted with 500 ml of ethyl acetate. The extract was concentrated to dryness under reduced pressure to give a powder (5 g). The powder (5 g) was dissolved in 10 ml of methanol (500 mg/ml) and applied to HPLC using a steel column (20 mm inside diameter, 250 mm length) packed with D-ODS-5 (YMC-PACKED COLUMN) and eluted with a mixture of Methanol and water [8:2] at a flow rate of 9.9 ml/minute. Thus obtained active fraction was concentrated under reduced pressure, and then extracted with ethyl acetate. The extract was concentrated to dryness under reduced pressure to give a pure white powder (150 mg) of WS-9326A.

EXAMPLE 2

To a solution of WS-9326A 300 mg) in pyridine (4.5 ml) were added acetic anhydride (1.5 ml) and 4-dimethylaminopyridine (1 mg) and the reaction mixture was allowed to stand at room temperature overnight. The reaction mixture was evaporated to dryness to afford an oil which was purified by preparative TLC (chloroform-methanol (10:1)).

The obtained product was triturated from diethyl ether to give triacetyl-WS-9326A (332 mg) as a colorless powder. Physical and chemical properties of the triacetyl-WS-9326A are as follows.

(1) Form and Color: colorless powder
(2) Color Reaction:
    Positive: cerium sulfate reaction, sulfuric acid reaction, iodine vapor reaction
    Negative: ninhydrine reaction
(3) Solubility:
    Soluble: methanol, dimethyl sulfoxide
    Sparingly Soluble: chloroform, diethyl ether
    Insoluble: n-hexane
(4) Melting Point: 141–143° C.
(5) Specific Rotation:
    $[\alpha]_D^{23}$: $-122°$ (C = 1.0, MeOH)
(6) Ultraviolet Absorption Spectrum:
    $\lambda_{max}^{MeOH} = 283$ nm ($\epsilon = 32,000$)
(7) Molecular Formula: $C_{60}H_{74}N_8O_{16}$
(8) Elemental Analysis (percentage by weight):
    Found: C 60.19, H 6.42, N 9.27;
    Calcd. for $C_{60}H_{74}N_8O_{16} \cdot 2H_2O$: C 60.09, H 6.56, N 9.34.
(9) Molecular Weight:
    FAB-MS: m/z 1163.6 (M + H)+
(10) Thin Layer Chromatography:

| Stationary phase | Developing solvent | Rf value |
|---|---|---|
| Silica gel plate (MERCK ART 5715) | Chloroform-methanol (10:1, V/V) | 0.50 |
| | Ethyl acetate | 0.12 |

(11) Infrared Absorption Spectrum:
    $\nu_{max}^{KBr} =$ 3350, 3020, 2950, 2920, 2850, 1730, 1650, -continued 1520, 1440, 1360, 1230, 1200, 1160, 1100, 1060, 1040, 910 cm$^{-1}$

(12) Property of the Substance:
 neutral substance
(13) $^{13}$C Nuclear Magnetic Resonance Spectrum:
 (100 MHz, CDCl$_3$—CD$_3$OH (10:1)) δ

Figure 4:
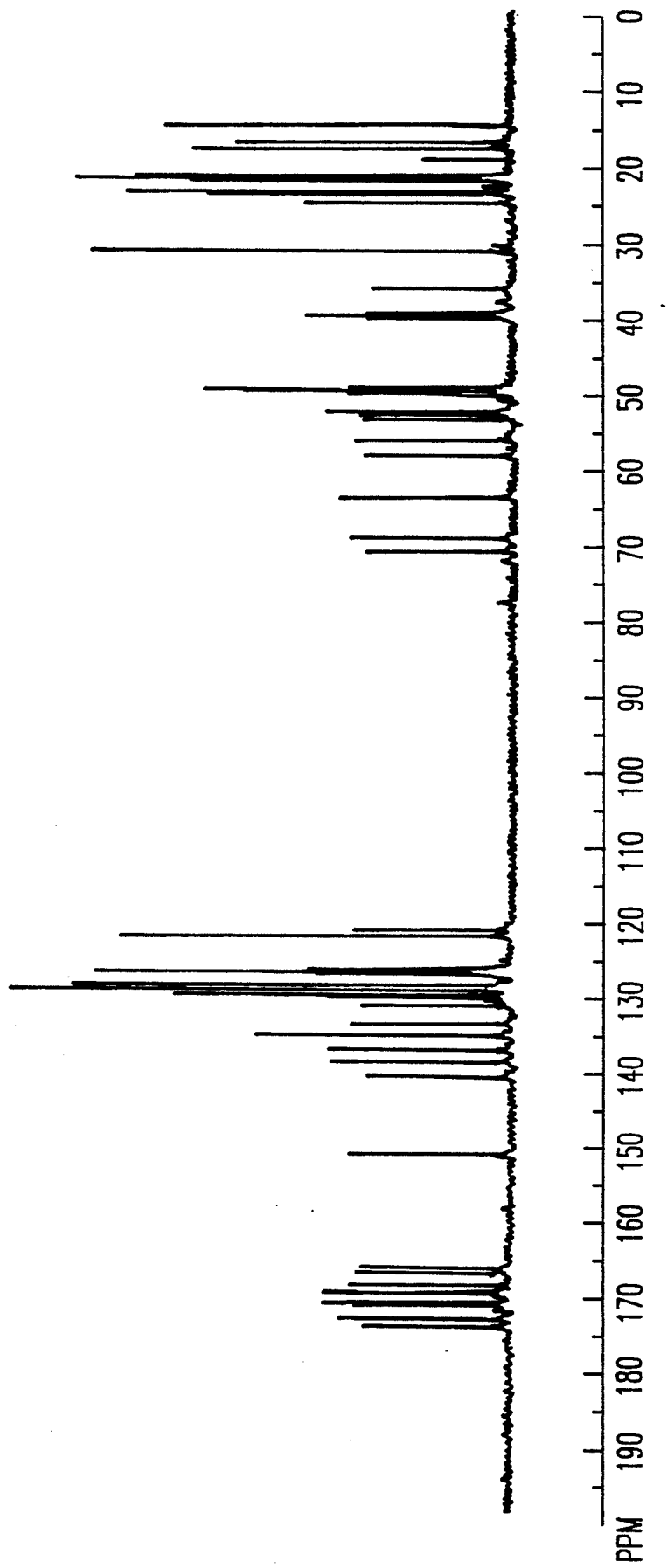
FIG. 4 represents the spectrum of $^{13}$C nuclear magnetic resonance of triacetyl-WS-9326A in CDCl$_3$—CD$_3$OH(10:1)

| | |
|---|---|
| 174.20 (s), | 173.23 (s), |
| 173.06 (s), | 171.32 (s), |
| 171.02 (s), | 170.84 (s), |
| 169.79 (s), | 169.59 (s), |
| 169.55 (s), | 168.52 (s), |
| 167.03 (s), | 166.36 (s), |
| 151.02 (s), | 140.74 (d), |
| 138.82 (s), | 138.74 (s), |
| 137.12 (s), | 135.23 (d), |
| 133.75 (s), | 131.31 (s), |
| 130.20 (d), | 129.96 (d) × 2, |
| 129.34 (d), | 129.21 (d) × 2, |
| 128.56 (d) × 2, | 127.24 (d), |
| 126.95 (d), | 126.74 (d), |
| 126.63 (d), | 126.50 (d), |
| 122.10 (d) × 2, | 121.29 (d), |
| 70.99 (d), | 69.22 (d), |
| 63.73 (t), | 58.13 (d), |
| 56.10 (d), | 53.22 (d), |
| 52.66 (d), | 52.18 (d), |
| 49.93 (d), | 39.75 (t), |
| 39.39 (q), | 39.06 (t), |
| 35.57 (t), | 30.65 (t), |
| 24.26 (d), | 23.15 (q), |
| 22.79 (t), | 21.42 (q), |
| 21.21 (q), | 20.99 (q), |
| 20.83 (q), | 17.05 (q), |
| 16.18 (q), | 13.82 (q), | the chart of which is shown in FIG. 4,
(14) $^1$H Nuclear Magnetic Resonance Spectrum:
 (400 MHz, CDCl$_3$—CD$_3$OH (10:1)) δ

Figure 5:
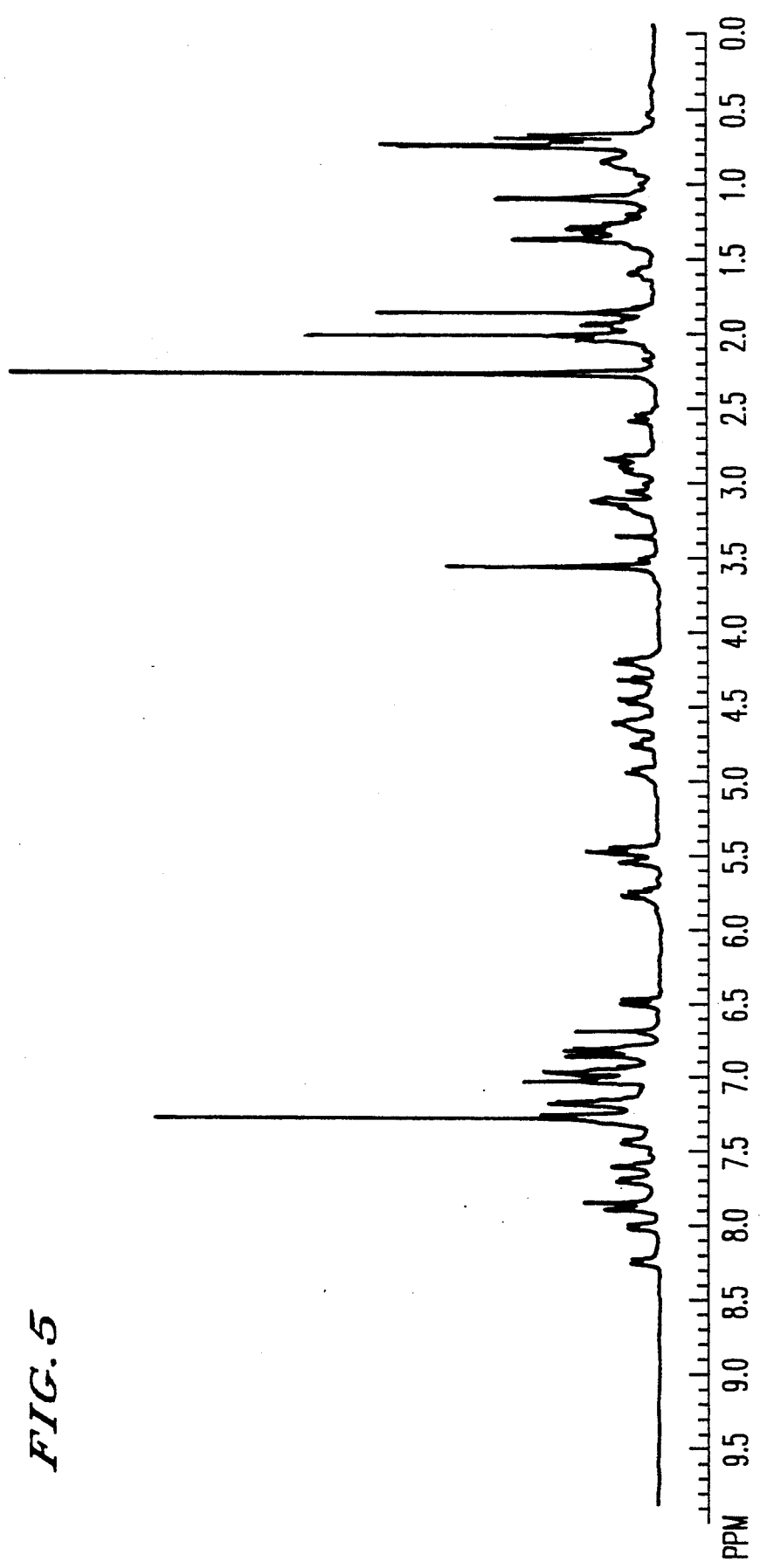
FIG. 5 represents the spectrum of $^1$H nuclear magnetic resonance of triacetyl-WS-9326A in CDCl$_3$—CD$_3$OH(10:1)

| | |
|---|---|
| 8.25 | (1H, d, J=8Hz), |
| 8.02 | (1H, d, J=8Hz), |
| 7.88 | (1H, d, J=16Hz), |
| 7.86 | (1H, d, J=8Hz), |
| 7.70 | (1H, d, J=6Hz), |
| 7.61 | (1H, d, J=8Hz), |
| 7.45 | (1H, d, J=7Hz), |
| 7.32–7.15 | (6H, m), |
| 7.03 | (2H, d, J=8Hz), |
| 7.00–6.94 | (3H, m), |
| 6.88–6.79 | (4H, m), |
| 6.70 | (1H, s), |
| 6.49 | (1H, d, J=12Hz), |
| 5.76 | (1H, dt, J=12 and 7.5Hz), |
| 5.54 | (1H, broad s), |
| 5.50–5.45 | (2H, m), |
| 4.93 | (1H, m), |
| 4.75 | (1H, m), |
| 4.65–4.56 | (2H, m), |
| 4.46 | (1H, dd, J=6 and 11Hz), |
| 4.31 | (1H, t, J=6Hz), |
| 4.22 | (1H, m), |
| 4.18 | (1H, dd, J=8 and 11Hz), |
| 3.56 | (3H, s), |
| 2.90 | (1H, dd, J=6 and 16Hz), |
| 2.85–2.80 | (2H, m), |
| 2.56 | (1H, dd, J=4 and 16Hz), |
| 2.26 | (3H, s), |
| 2.00 | (3H, s), |
| 1.96–1.89 | (2H, m), |
| 1.85 | (3H, s), |
| 1.58 | (1H, m), |
| 1.35 | (3H, d, J=6Hz), |
| 1.32–1.20 | (3H, m), |
| 1.07 | (3H, d, J=6Hz), |
| 0.84 | (1H, m), |
| 0.72 | (3H, d, J=6Hz), |
| 0.71 | (3H, t, J=7.5Hz), |
| 0.65 | (3H, d, J=6Hz), | the chart of which is shown in FIG. 5.

EXAMPLE 3

Fermentation

An aqueous seed medium (160 ml) containing soluble starch (1%), sucrose (1%), glucose (1%), cotton seed flour (1%), peptone (0.5%), soybean meal (0.5%) and calcium carbonate (0.2%) was poured into each of ten 500-ml Erlenmeyer flasks and sterilized at 120° C. for 30 minutes.

A loopful of slant culture of *Streptomyces violaceoniger* No. 9326 was inoculated to each of the media and cultured on a rotary shaker (220 rpm, 5.1 cm throw) at 30° C. for 3 days.

The resultant seed culture was inoculated to the aqueous seed medium (160 l) containing soluble starch (1%), sucrose (1%), glucose (1%), cotton seed flour (1%), peptone 0.5%), soybean meal (0.5%), calcium carbonate (0.2%), ADEKANOL LG-109 (deforming agent, Trademark: Asahi Denka Co.) (0.07%) and SILICONE KM-70 (deforming agent, Trademark : Shin-etsu Chemical Co.) (0.05%) in a 500-liter stainless steel jar-fermentor which had been sterilized at 120° C. for 30 minutes in advance. The fermentation was carried out at 30° C. for 1 day under aeration of 160 liters/minute and agitation of 200 rpm.

The resultant seed cultured broth (60 l) was inoculated to a sterilized production medium containing glycerin (3.0%), soybean meal (1.0%), chicken meat bone meal (1.0%), calcium carbonate (0.2%), sodium iodide (0.001%), ADEKANOL LG-109 (0.07%) and SILICONE KM-70 (0.05%) in a 4,000-liter stainless steel jar-fermentor which had been sterilized at 120° C. for 30 minutes in advance, and cultured at 30° C. for 4 days under aeration of 3,000 liters/minute and agitation of 100 rpm.

The progress of the fermentation was monitored by high performance liquid chromatography (HPLC) using HITACHI MODEL 655 pump. A steel column packed with a reverse phase silica gel "YMC-PACKED COLUMN R-ODS-5" (Trademark, Yamamura Chemical Institute) was used at a flow rate of 1.0 ml/minute. Mobile phase used was an aqueous solution of 45% acetonitrile. The sample for the HPLC assay was prepared as follows; an equal volume of acetone was added to a broth with vigorous stirring and the mixture was stand for one hour and then centrifuged. The 5 μl of supernatant was injected to the injector of HITACHI MODEL 655 HPLC.

Isolation and Purification

The cultured broth thus obtained was filtered with an aid of diatomaceous earth PERLITE TOPKO #34, Trademark, Showa Chemical Industry Co., Ltd.) (15 kg). The mycelial cake was extracted with ethyl acetate (1600 ) and the extract was filtered. The filtrate (1400 l) was applied to a column of active carbon (SIRASAGI KL, Trademark, Takeda Pharmaceutical Co., Ltd.) (200 l). The column was washed with ethyl acetate (120 l) and then the elution was carried out with ethyl acetate-methanol [5:1]. The active fractions (fractions from 50 l to 1030 l) were combined and concentrated to 45 l under reduced pressure. n-Hexane (120 ) was added to the resultant solution with stirring. The mixture was allowed to stand at room temperature for one hour and then filtered with an aid of SILIKA #600 (Chuo Silica Co., Ltd. (3 kg). The cake thus obtained was washed with n-hexane (15 l) and the object substances were eluted with methanol (20 l).

The eluate was concentrated to dryness under reduced pressure. The residue (500 g) was dissolved with methanol-acetic acid-dichloromethane [1:1:2] (4 l) and applied to a column of silica gel (KIESELGEL 60, 70-230 mesh, 70 l). The column was developed with methanol-acetic acid-dichloromethane [1:1:2] (0.5 l) and dichloromethane (25 l). The object substances were eluted with dichloromethane-methanol [10:1] and dichloromethane-methanol [8:1]. The active fractions were combined and concentrated under reduced pressure. The residue was dissolved with methanol (1 l). Acetonitrile (9 l) was added to the resultant solution with stirring. The mixture was allowed to stand at room temperature for one hour and the resultant precipitate was collected by filtration. This precipitation step was repeated three times. The precipitate thus obtained was washed with acetonitrile (1 l) and dried to give a white powder (190 g) of WS-9326A. The filtrates thus obtained from these precipitation steps were combined and concentrated to dryness under reduced pressure. The residue (11.7 g) was dissolved with 80% aqueous methanol and resultant solution was passed through a column of active carbon (300 ml). The column was washed with 80% aqueous methanol (1 l) and the elution was carried out with methanol (6 l). The active fractions were combined and concentrated to dryness under reduced pressure. The residue (3.4 g) was dissolved with methanol (12 ml). The resultant solution was applied to a column of reverse phase silica gel (YMC PACKED COLUMN R-354 S-15/30 (ODS), $\phi 50 \times 1\,300$ mm$\times 2$; maker, Yamamura Chemical Institute) equilibrated with 50% aqueous acetonitrile. The column was developed with 50% aqueous acetonitrile using Waters HPLC (SYSTEM 500). The eluates containing WS-9326B (fractions 3 l to 3.5 l) were combined and concentrated to dryness to give a white powder (790 mg) of WS-9326 B.

EXAMPLE 4

To a solution of WS-9326A (100 mg) in pyridine (1 ml) was added acetic anhydride (0.01 ml) and the mixture was allowed to stand at room temperature overnight. The mixture was evaporated to dryness to afford an oil which was purified by preparative TLC (chloroform-methanol (9:1)). The obtained product was triturated with diethyl ether to give monoacetyl-WS-9326A (55 mg) as a colorless powder. Physical and Chemical properties of the monoacetyl-WS-9326A are as follows.

(1) Form and Color: colorless powder
(2) Molecular Formula: $C_{56}H_{70}N_8O_{14}$
(3) Molecular Weight:
    FAB-MS: m/z 1079.4 $(M + H)^+$
(4) Thin Layer Chromatography:

| Stationary phase | Developing solvent | Rf value |
|---|---|---|
| Silica gel plate (MERCK ART 5715) | Chloroform-methanol (10:1, V/V) | 0.17 |

Figure 8:
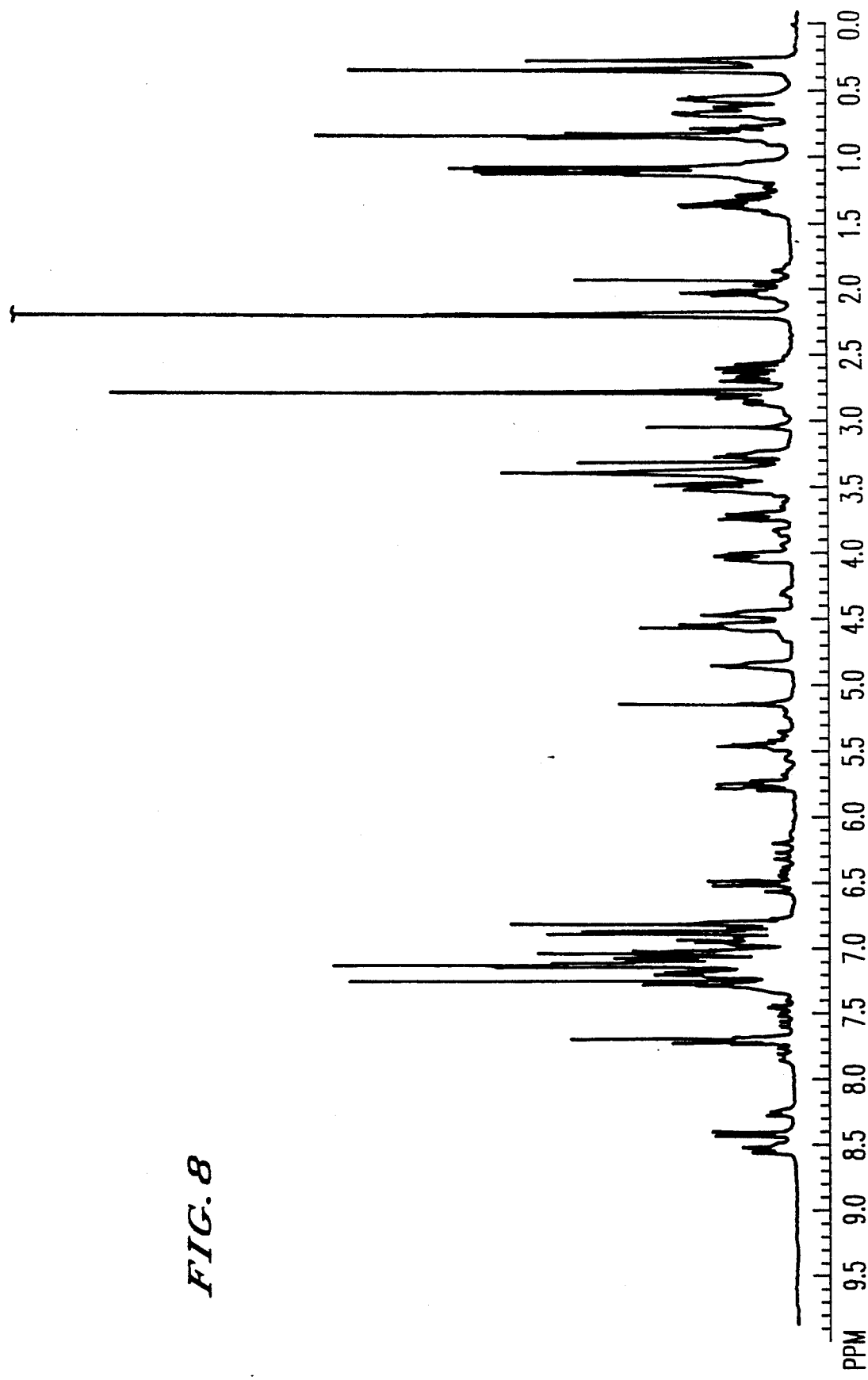
FIG. 8 represents the spectrum of $^1$H nuclear magnetic resonance of monoacetyl-WS-9326A in CDCl$_3$—CD$_3$OD(5:1)

(5) Infrared Absorption Spectrum:
    $\nu_{max}^{KBr} =$ 3300, 2920, 1730, 1650, 1500, 1360, 1190, 1170, 910 cm$^{-1}$
(6) Property of the Substance:
    neutral substance
(7) $^1$H Nuclear Magnetic Resonance Spectrum
    (400 MHz, CDCl$_3$—CD$_3$OD (5:1)):
    the chart of which is shown in FIG. 8.

EXAMPLE 5

To a solution of WS-9326A (100 mg) in pyridine (1 ml) was added acetic anhydride (0.03 ml) and the mixture was allowed to stand at room temperature overnight. The mixture was evaporated to dryness to afford an oil which was purified by preparative TLC (chloroform-methanol (9:1)) to give diacetyl-WS-9326A (72 mg) as a colorless powder. Physical and chemical properties of the diacetyl-WS-9326A are as follows.

(1) Form and color: colorless powder
(2) Molecular Formula: $C_{58}H_{72}N_8O_{15}$
(3) Molecular Weight:
    FAB-MS: m/z 1121.4 $(M + H)^+$
(4) Thin Layer Chromatography:

| Stationary phase | Developing solvent | Rf value |
|---|---|---|
| Silica gel plate (MERCK ART 5715) | Chloroform-methanol (10:1, V/V) | 0.35 |

Figure 9:
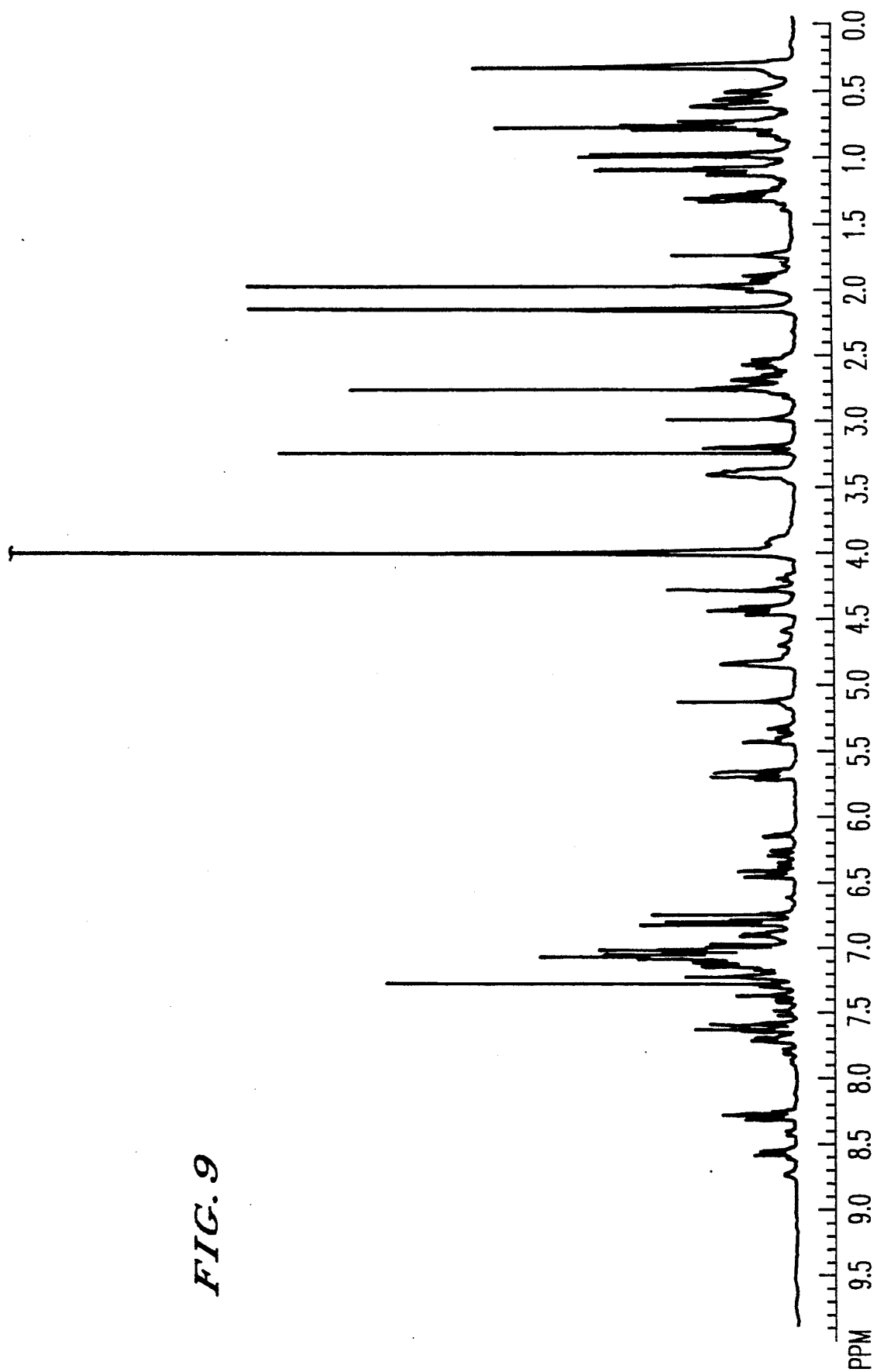
FIG. 9, represents the spectrum of $^1$H nuclear magnetic resonance of diacetyl-WS-9326A in CDCl$_3$—CD$_3$OD(5:1)

(5) Infrared Absorption Spectrum:
    $\nu_{max}^{KBr} =$ 3300, 3020, 2950, 1730, 1650, 1520, 1500, 1360, 1200, 1170, 1100, 1040, 980, 910 cm$^{-1}$
(6) Property of the Substance:
    neutral substance
(7) $^1$H Nuclear Magnetic Resonance Spectrum
    (400 MHz, CDCl$_3$—CD$_3$OD (5:1)):
    the chart of which is shown in FIG. 9.

EXAMPLE 6

WS-9326A (100 mg) was dissolved in methanol (2 ml) and the solution was hydrogenated over palladium black (25 mg) under 1 atmospheric pressure of hydrogen at room temperature for 4 hours. The mixture was filtered and the filtrate was concentrated to dryness under reduced pressure. The obtained product was triturated with diethyl ether to give tetrahydro-WS-9326A (92 mg) as a colorless powder. Physical and chemical properties of the tetrahydro-WS-9326A are as follows.

Figure 10:
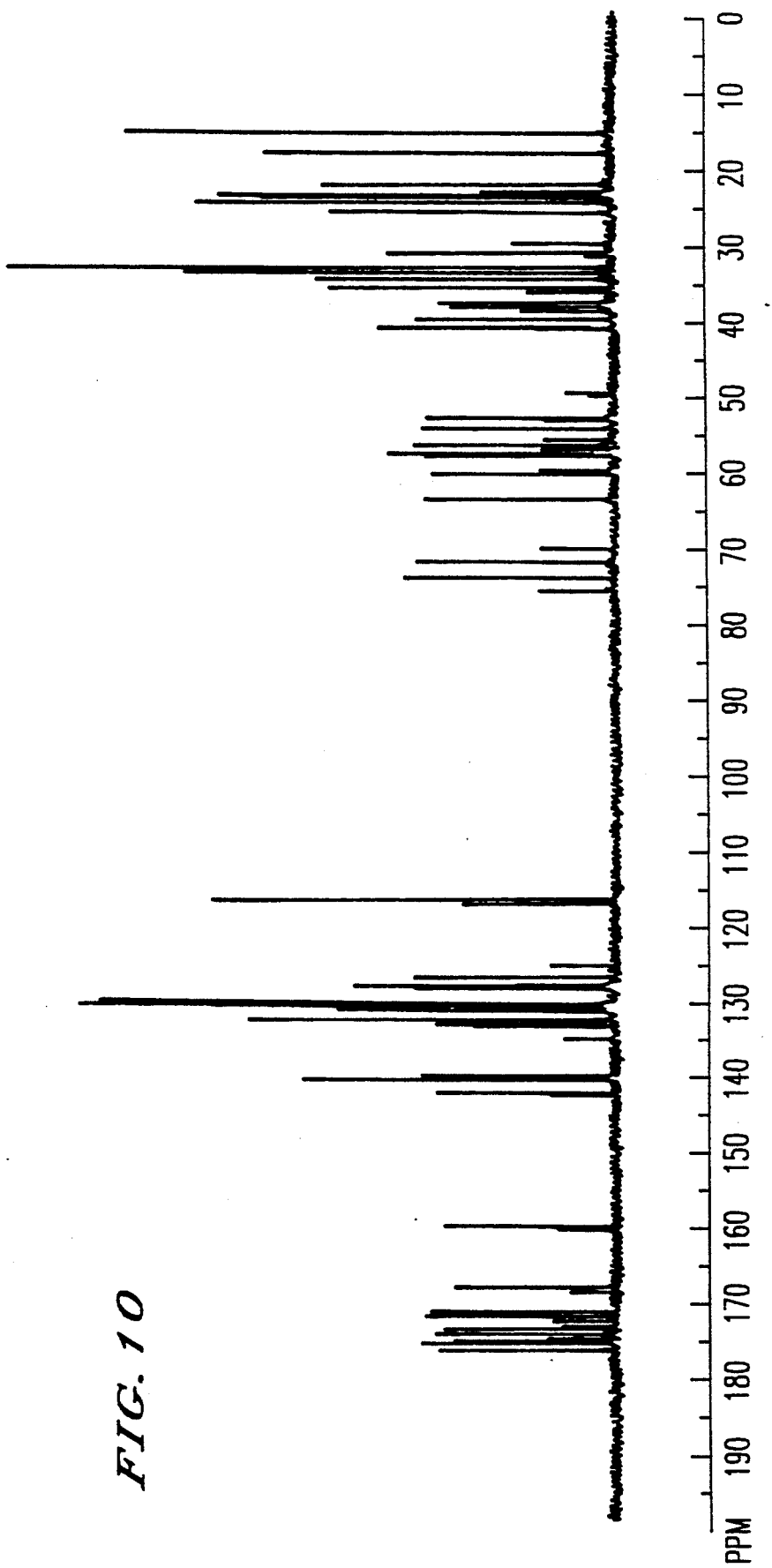
FIG. 10, represents the spectrum of $^{13}$C nuclear magnetic resonance of tetrahydro-WS-9326A in CD$_3$OD.
Figure 11:
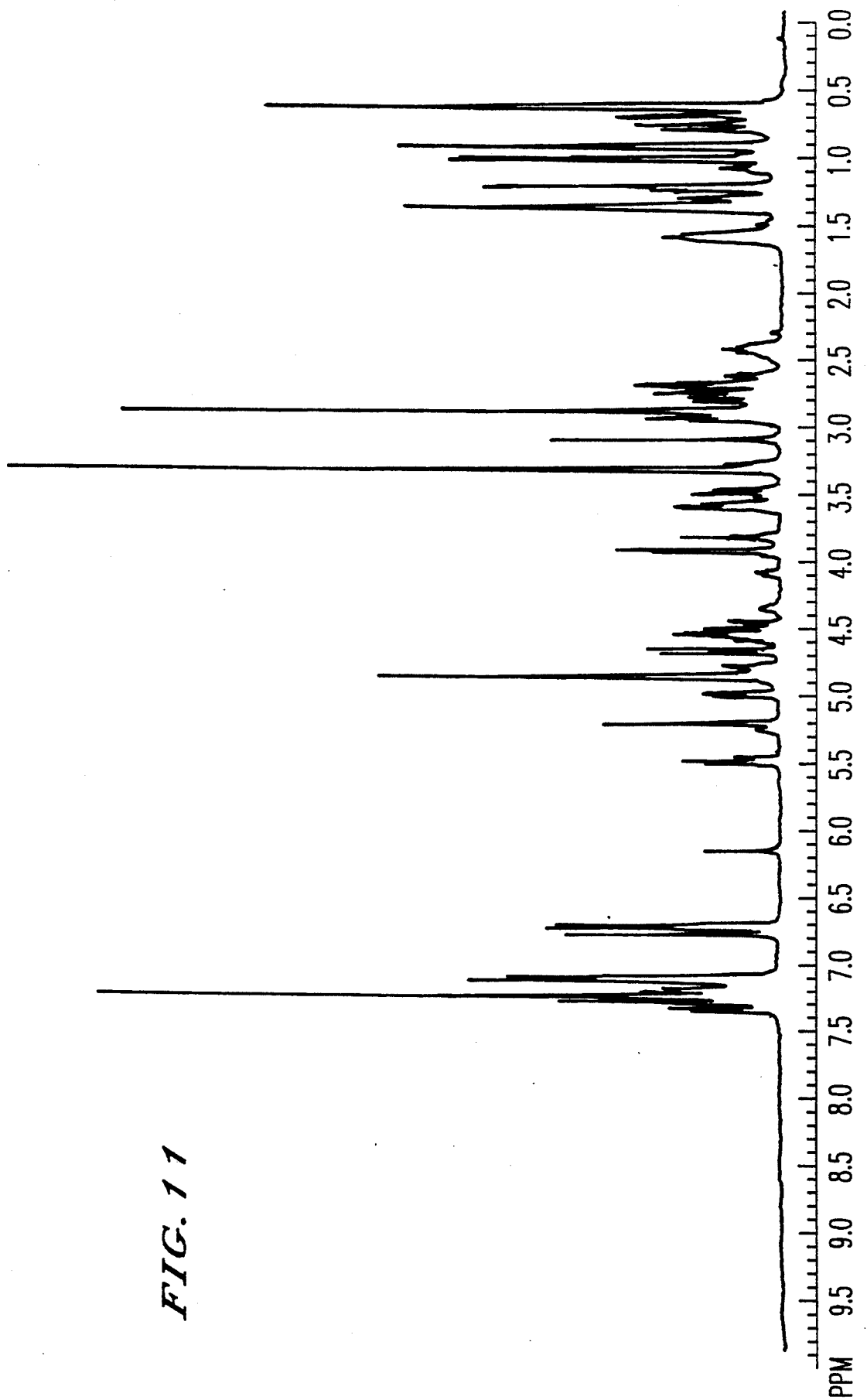
FIG. 11, represents the spectrum of $^1$H nuclear magnetic resonance of tetrahydro-WS-9326A in CD$_3$OD.

(1) Form and color: colorless powder
(2) Ultraviolet Absorption Spectrum:
    $\lambda_{max}^{MeOH}$ 287 nm ($\epsilon$ = 13,000)
(3) Molecular Formula: $C_{54}H_{72}N_8O_{13}$
(4) Molecular Weight:
    FAB-MS: m/z 1041.6 $(M + H)^+$
(5) $^{13}$C Nuclear Magnetic Resonance Spectrum
    (100 MHz, CD$_3$OD):
    the chart of which being shown in FIG. 10
(6) $^1$H Nuclear Magnetic Resonance Spectrum
    (400 MHz, CD$_3$OD):
    the chart of which being shown in FIG. 11

EXAMPLE 7

To a solution of tetrahydro-WS-9326A (1100 mg) in pyridine (10 ml) were added acetic anhydride (3 ml) and 4-dimethylaminopyridine (3 mg) and the reaction mixture was allowed to stand at room temperature overnight. The solution was evaporated to dryness to afford an oil which was purified by silica gel column chromatography (chloroform-methanol (20:1)). The obtained pure product was triturated with diethyl ether to give tetrahydro-triacetyl-WS-9326A (998 mg) as a colorless powder. Physical and chemical properties of tetrahydrotriacetyl-WS-9326A are as follows.

(1) Form and color: colorless powder
(2) Ultraviolet Absorption Spectrum:

-continued $\lambda_{max}^{MeOH}$ 280 nm ($\epsilon$ = 13,000)
(3) Molecular Formula: $C_{60}H_{78}N_8O_{16}$
(4) Elemental Analysis (percentage by weight):
   Found: C 61.03, H 6.70, N 9.41;
   Calcd. for $C_{60}H_{78}N_8O_{16}\cdot H_2O$   C 60.80, H 6.80, N 9.45.
(5) Molecular Weight:
   FAB-MS: m/z 1167.6 $(M + H)^+$
(6) $^{13}C$ Nuclear Magnetic Resonance Spectrum:

| (100 MHz, CDCl$_3$) | $\delta$ |
|---|---|
| 173.30 (s), | 129.23 (d), |
| 172.96 (s), | 128.95 (d) × 2, |
| 172.90 (s), | 128.61 (d) × 2, |
| 172.81 (s), | 128.52 (d), |
| 170.87 (s), | 126.80 (d), |
| 170.56 (s), | 126.07 (d), |
| 170.50 (s), | 126.01 (d), |
| 169.46 (s), | 125.85 (d), |
| 169.16 (s), | 121.87 (d) × 2, |
| 168.48 (s), | 70.46 (d), |
| 167.99 (s), | 69.10 (d), |
| 165.52 (s), | 63.32 (t), |
| 150.70 (s), | 58.28 (d), |
| 140.84 (s), | 56.19 (d), |
| 138.93 (s), | 52.63 (d), |
| 138.58 (s), | 52.07 (d), |
| 136.83 (s), | 51.63 (d), |
| 131.04 (s), | 49.23 (d), |
| 129.71 (d) × 2, | 39.30 (t), |
| 39.17 (q), | 22.50 (t), |
| 38.31 (t), | 21.46 (q), |
| 36.52 (t), | 21.00 (q), |
| 35.22 (t), | 20.74 (q), |
| 32.60 (t), | 20.63 (q), |
| 31.77 (t), | 16.77 (q), |
| 30.74 (t), | 16.22 (q), |
| 27.66 (t), | 13.97 (q). |
| 24.08 (d), | |
| 22.82 (q), | |

(7) $^1H$ Nuclear Magnetic Resonance Spectrum:

| (400 MHz, CDCl$_3$) | $\delta$ |
|---|---|
| 8.18 | (1H, d, J=8Hz), |
| 7.66 | (1H, d, J=8Hz), |
| 7.65 | (1H, d, J=8Hz), |
| 7.29 | (2H, d, J=8Hz), |
| 7.22 | (1H, d, J=8Hz), |
| 7.15–7.02 | (12H, m), |
| 6.96 | (1H, d, J=7Hz), |
| 6.67 | (1H, s), |
| 6.21 | (1H, broad s), |
| 5.51 | (1H, broad s), |
| 5.43 | (1H, m), |
| 5.36 | (1H, broad d, J=8Hz), |
| 4.85–4.75 | (2H, m), |
| 4.66–4.58 | (2H, m), |
| 4.40 | (1H, dd, J=11 and 6Hz), |
| 4.34 | (1H, m), |
| 4.23 | (1H, dd, J=11 and 9Hz), |
| 4.07 | (1H, m), |
| 3.53 | (3H, s), |
| 3.04–2.84 | (5H, m), |
| 2.75–2.50 | (4H, m), |
| 2.46 | (1H, dd, J=16 and 5Hz), |
| 2.28 | (3H, s), |
| 1.99 | (3H, s), |
| 1.87 | (3H, s), |
| 1.66–1.50 | (3H, m), |
| 1.37–1.27 | (4H, m), |
| 1.27 | (3H, d, J=7Hz), |
| 1.19 | (1H, m), |
| 1.03 | (3H, d, J=7Hz), |
| 0.88 | (1H, m), |
| 0.86 | (3H, t, J=6Hz), |
| 0.72 | (3H, d, J=6Hz), |
| 0.65 | (3H, d, J=6Hz) |

EXAMPLE 8

Triacetyl-WS-9326A (100 mg) was dissolved in methanol (3 ml) and the solution was hydrogenated over palladium black (35 mg) under 1 atmospheric pressure of hydrogen at room temperature for 3 hours.

The mixture was filtered and the filtrate was evaporated to dryness under reduced pressure.

The residue was triturated with diethyl ether to give a compound (90 mg) as a colorless powder.

This compound was identical in all respects with tetrahydro-triacetyl-WS-9236A obtained in Example 7.

From the analysis of the above physical and chemical properties, and the result of further investigation for identification of chemical structure, the chemical structures of the triacetyl-WS-9326A, monoacetyl-WS-9326A, diacetyl-WS-9326A, tetrahydro-WS-9326A and tetrahydrotriacetyl-WS-9326A have been identified as follows.

triacetyl-WS-9326A

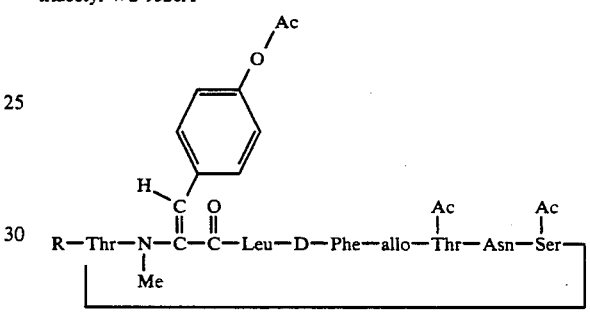

R—: (E)-3-[2-((Z)-1-pentenyl)phenyl]propenoyl monoacetyl-WS-9326A

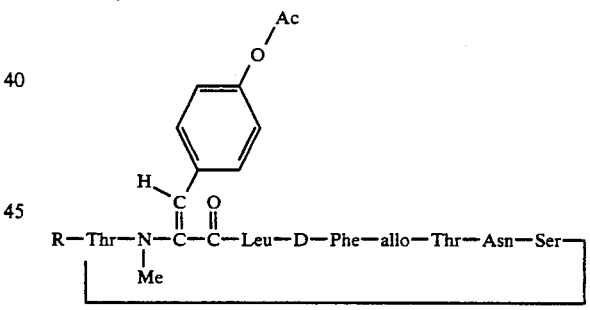

R—: (E)-3-[2-((Z)-1-pentenyl)phenyl]propenoyl diacetyl-WS-9326A

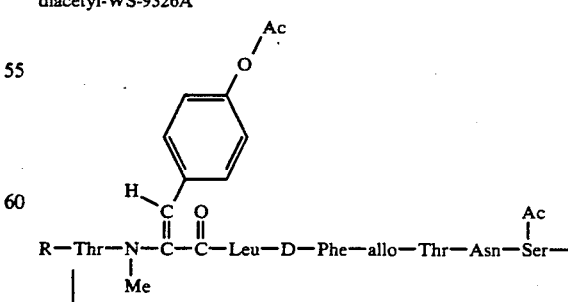

R—: (E)-3-[2-((Z)-1-pentenyl)phenyl]propenoyl tetrahydro-WS-9326A

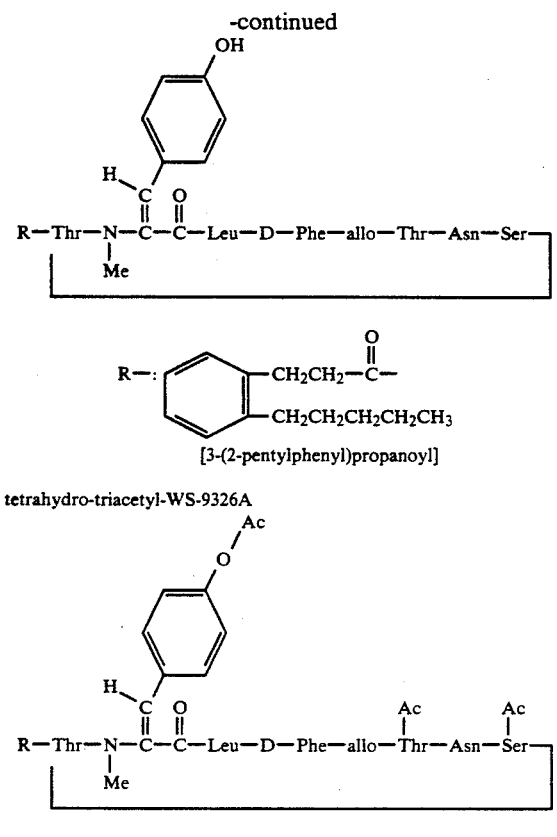

[3-(2-pentylphenyl)propanoyl]

tetrahydro-triacetyl-WS-9326A

R—: 3-(2-pentylphenyl)propanoyl

EXAMPLE 9

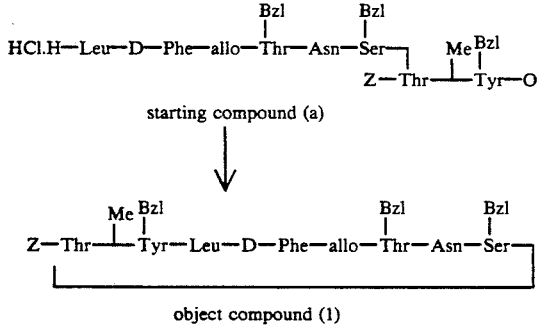

To a solution of the starting compound (a) (3.24 g) in dichloromethane (1000 ml) were added triethylamine (350 μl) and 1-ethoxycarbonyl-2-ethoxy-1,2-dihydroquinoline (6.17 g) at room temperature. After the mixture was stirred for 24 hours at room temperature, solvent was evaporated. Chloroform was added to the residue and the mixture was washed with water, 1N hydrochloric acid, water, a saturated aqueous solution of sodium bicarbonate and water. After the mixture was dried over magnesium sulfate and filtered, solvent was evaporated. The residue was subjected to "lober column" (size C) chromatography and eluted with 3% methanol in chloroform. Fractions containing the object compound were evaporated to give the object compound (1) (1.06 g).

$[\alpha]_D^{18}$: −95.3° (c=0.33, CHCl$_3$)
IR (CHCl$_3$): 1660, 1600, 1510 cm$^{-1}$ NMR (CDCl$_3$,δ): 0.88 (3H, d, J=6Hz), 0.93 (3H, d, J=6Hz), 1.09 (3H, d, J=6.5Hz), 1.37 (3H, d, J=6.5), 2.82 (3H, s), 4.87 (2H, s), 6.93 (2H, d, J=8Hz).

EXAMPLE 10

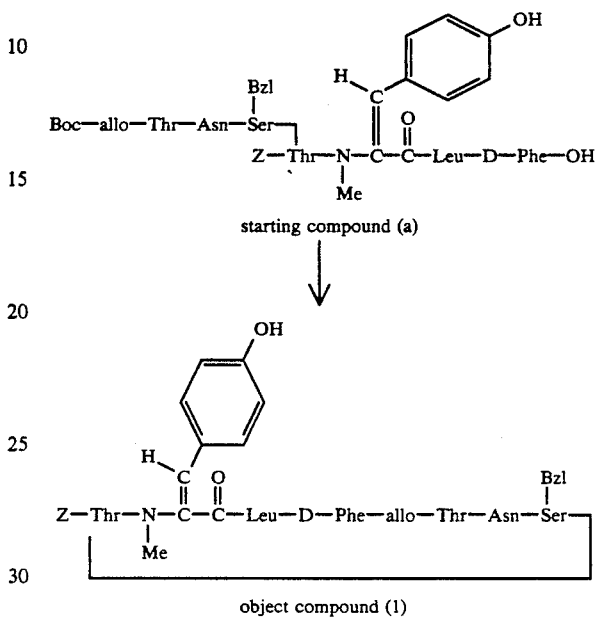

To a solution of the starting compound (a) (42 mg) dichloromethane (4 ml) and N,N-dimethylformamide (0.1 ml) were added N-hydroxysuccinimide (20.4 mg) and a water soluble carbodiimide hydrochloride (8.2 mg).

After stirring for 15 hours at room temperature, water soluble carbodiimide hydrochloride (4 mg) was added to the mixture at 1.5-hour intervals until the starting compound (a) disappeared.

The solvent was removed in vacuo and the residue was dissolved in ethyl acetate (10 ml) and washed with dil. hydrochloric acid and water.

After drying over magnesium sulfate, the solvent was removed in vacuo and the residue was dissolved in trifluoroacetic acid (1 ml) and anisole (0.1 ml).

After stirring for 30 minutes at room temperature, the solvent was removed in vacuo. The residue was dissolved in N,N-dimethylformamide (2 ml) and the mixture was added to pyridine (40 ml).

After stirring for 16 hours at room temperature, the solvent was removed in vacuo. The residue was subjected to preparative thin layer chromatography (MERCK 5744) and developed with chloroform-methanol (10:1) to give the object compound (1) (15.2 mg).

IR (KBr): 1635, 1510 cm$^{-1}$
NMR (CD OD, δ): 6.24 (1H, s)
$[\alpha]_D^{20}$: +18.0° (C=0.1, MeOH)

EXAMPLE 11

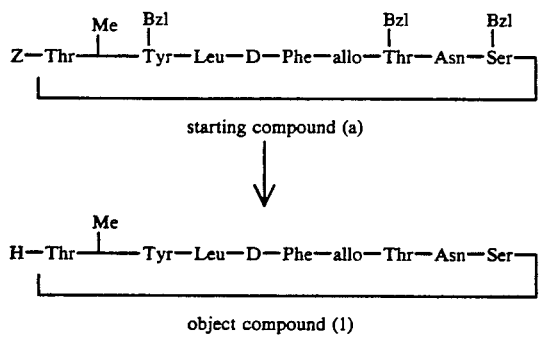

The starting compound (a) (240 mg) was hydrogenated at 4 psi with palladium (200 m) in a mixture of formic acid and methanol (1:24, 10 ml) for 7 hours.

After the mixture was filtered, the filtrate was evaporated to give the object compound (1) (140 mg).

IR (KBr): 1730, 1650, 1510 cm$^{-1}$
$[\alpha]_D^{21}$: $-21.04°$ (C=0.1, MeOH)

EXAMPLE 12

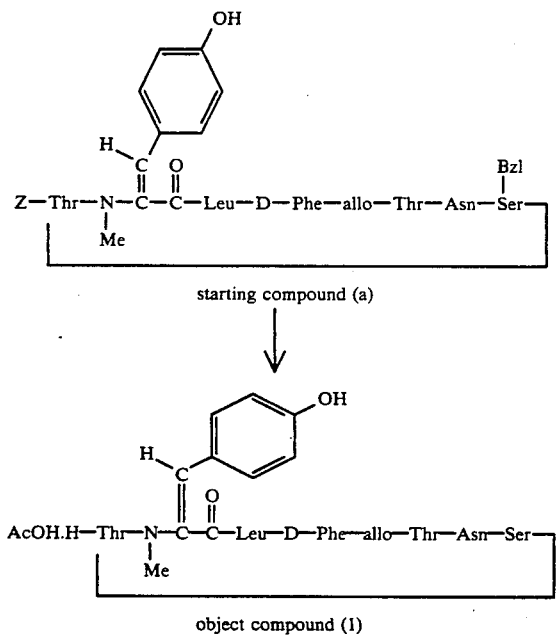

The starting compound (a) (22 mg) was dissolved in a solution of hydrogen fluoride-pyridine (0.8 ml) and anisole (0.2 ml) in nitrogen gas-bag. After stirring for 1 hour at room temperature, some pieces of ice were added to the mixture and the solution was adjusted to pH 8 with sodium bicarbonate aqueous solution. The mixture was put on a column of Diaion HP-20 (10 ml) and washed with water. The product was eluted with methanol and purified by thin layer chromatography (MERCK 5715, chloroform-methanol-water (3:1:01, V/V)) to give the object compound (1) (13.0 mg).

IR (KBr): 1635, 1510 cm$^{-1}$
NMR(CD$_3$OD, δ): 7.05 (1H, s)
$[\alpha]_D^{20}$: $-90.6°$ (C=0.1, MeOH)
TLC: Rf=0.35 [MERCK ART 5715, CHCl$_3$—MeOH—H$_2$O (3:1:0.1)]

EXAMPLE 13

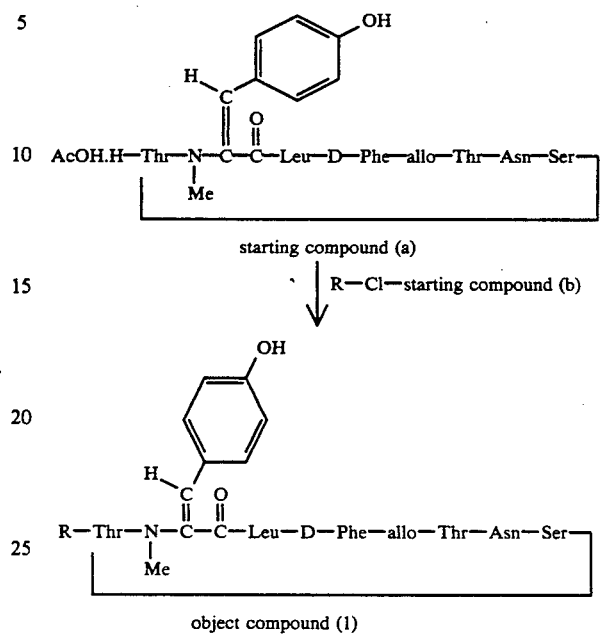

R—: (E)-3-[2-((Z)-1-pentenyl)phenyl]propenoyl

To a solution of the starting compound (a) (6.0 mg) in dichloromethane (1.5 ml), bis(dimethylsilyl)acetamide (30 μl) and N,N-dimethylformamide (0.3 ml) was added 0.2M solution of the starting compound (b) (0.4 ml). After stirring for 1 Zhour at room temperature 4-dimethylaminopyridine (0.1 mg) was added to the mixture. The starting compound (b) was added to the mixture at 30-minute intervals until the starting compound (a) disappeared. Diluted hydrochloric acid was added to the mixture and the organic layer was washed with water. After evaporating in vacuo, the residue was subjected to preparative thin layer chromatography (MERCK 5715) and developed with chloroform-methanol-water (65:25:4 V/V) to give the object compound (1) (0.2 mg).

This compound was identical with WS-9326A obtained in Example 1.

EXAMPLE 14

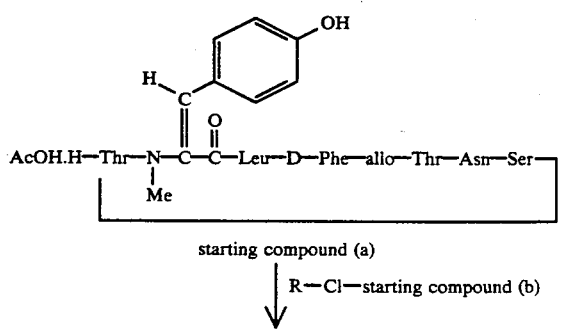

-continued

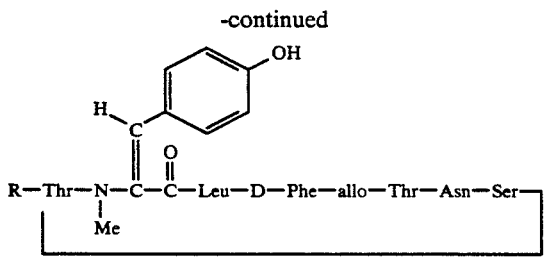

object compound (1)

R—: stearoyl (octadecanoyl)

To a solution of the starting compound a) (11 mg) in pyridine (1 ml) was added 0.02M solution of the starting compound (b) in dichloromethane (0.6 ml). After stirring for 1 hour at room temperature, the starting compound (b) was added to the mixture at 1 hour intervals until the starting compound (a) disappeared. Methanol (2 ml) was added to the mixture and the solvent was removed in vacuo. The residue was dissolved in ethyl acetate (10 ml) and washed with dil. hydrochloric acid and water. After drying over magnesium sulfate, the solvent was removed in vacuo. The residue was subjected to preparative thin layer chromatography (MERCK 5715) and developed with chloroform-methanol-water (3:1:0.1, V/V) to give the object compound (1) (2.0 mg).

IR (KBr): 1640, 1510 cm$^{-1}$

EXAMPLE 15

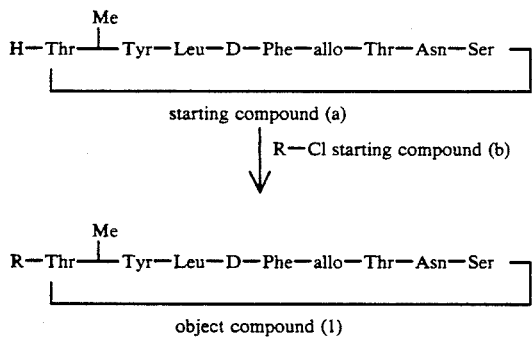

object compound (1)

R—: (E)-3-[2-((Z)-1-pentenyl)phenyl]propenoyl

To a solution of the starting compound (a) (49.7 mg) in pyridine (1 ml) was added 0.1M solution of the starting compound (b) in dichloromethane (1.2 ml) under nitrogen atmosphere and the mixture was stirred for 3.5 hours at room temperature. To the reaction mixture was added ethyl acetate and the mixture was washed with water, 7% acetic acid, water and a saturated aqueous solution of sodium chloride. After drying over magnesium sulfate and filtration, the solvent was evaporated, and the residue was subjected to preparative thin layer chromatography (0.5 mm×2) and developed with 20% methanol in chloroform to give the object compound (1) (20.6 mg).

This compound was identical with WS-9326B obtained in Example 3.

EXAMPLE 16

The following compounds were obtained according to a similar manner to that of Example 15.

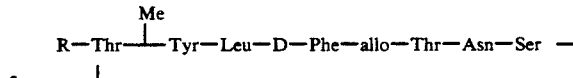

(1)
R—: benzoyl
$[\alpha]_D^{21}$: −45.8° (C=0.74, MeOH)
mp: 176°–178° C.
TLC: Rf=0.48 [MERCK ART 5715, CHCl$_3$—MeOH (5:1)]
IR (KBr): 1720 (shoulder), 1655, 1640 cm$^{-1}$ (2)
R—: 2-(2-thienyl)acetyl
$[\alpha]_D^{23}$: −16.8° (C=0.73, MeOH)
mp: 160°–163° C.
TLC: Rf=0.24 [MERCK ART 5715, CHCl$_3$—MeOH (5:1)]
IR (KBr): 1720 (shoulder), 1650 cm$^{-1}$ (3)
R-: acetyl
$[\alpha]_D^{21}$: −37.4° (C=0.73, MeOH)
mp: 231°–233° C.
TLC: Rf=0.41 [MERCK ART 5715, CHCl$_3$—MeOH (5:1)]
IR (KBr): 1720 (shoulder), 1650 cm$^{-1}$

EXAMPLE 17

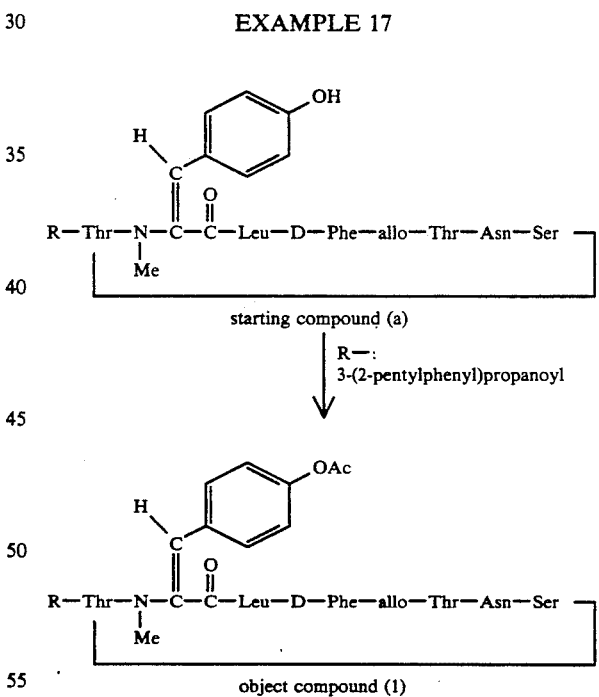

object compound (1)

To a solution of the starting compound (a) (100 mg) in pyridine (1 ml) was added acetic anhydride (11 μl) and the mixture was allowed to stand at room temperature overnight.

The mixture was evaporated to dryness to leave an oil which was purified by preparative TLC (CHCl$_3$—MeOH (9:1)) to give the object compound (1) (52 mg).

TLC: Rf=0.17 [MERCK ART 5715, CHCl$_3$—MeOH (10:1)]
IR (Nujol): 3300, 1760, 1730, 1650, 1530, 1510, 1200, 1160, 1070, 910 cm$^{-1}$

EXAMPLE 18

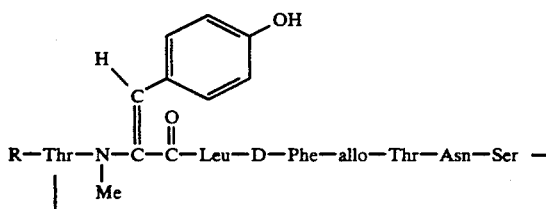

starting compound (a)

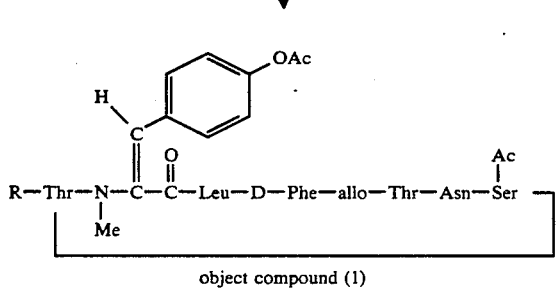

object compound (1)

R—: 3-(2-pentylphenyl)propanoyl

To a solution of the starting compound (a) (100 mg) in pyridine (1 ml) was added acetic anhydride (25 µl) and the mixture was allowed to stand at room temperature overnight.

The mixture was evaporated to dryness to leave an oil which was purified by preparative TLC (CHCl$_3$—MeOH (9:1)) to give the object compound (1) (78 mg).

TLC: Rf=0.36 [MERCK ART 5715, CHCl$_3$—MeOH (10:1)]

IR (Nujol): 3300, 1760, 1740, 1650, 1540, 1510, 1300, 1220, 1200, 1170, 1050, 920 cm$^{-1}$

EXAMPLE 19

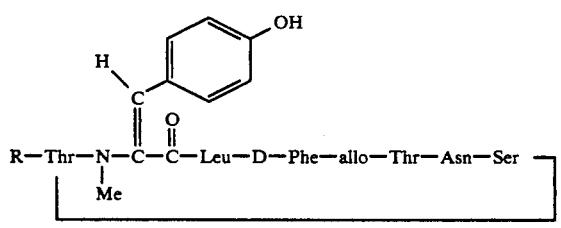

starting compound (a)

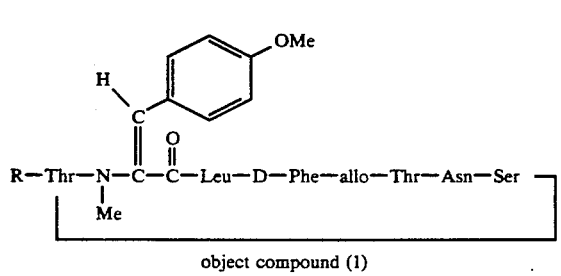

object compound (1)

R—: 3-(2-pentylphenyl)propanoyl

To a solution of the starting compound (a) (0.21 g) in methanol (3 ml) was added a solution (3 ml) of diazomethane in diethyl ether. After stirring for 5 minutes, the solvent was removed in vacuo. The residue was subjected on preparative thin layer chromatography (MERCK 5744) and developed with 20% methanol in chloroform to give the object compound (1) (45 mg).

IR (Nujol): 3300, 1730, 1645, 1530, 1510 cm$^{-1}$

EXAMPLE 20

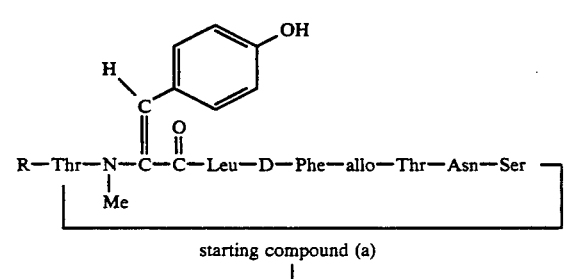

starting compound (a)

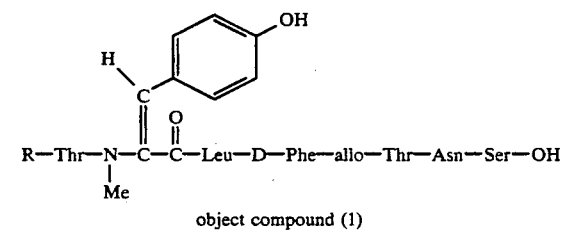

object compound (1)

R—: 3-(2-pentylphenyl)propanoyl

To a solution of the starting compound (a) (1.0 g) in methanol (15 ml) was added 1N-sodium hydroxide (5 ml) at 0° C. After stirring for 1 hour, 1N-hydrochloric acid (5 ml) was added to the solution. The solvent was removed in vacuo, and the residue was dissolve din a mixture of ethyl acetate (20 ml) and diluted hydrochloric acid (30 ml). The organic layer was washed with brine, dried over magnesium sulfate and evaporated in vacuo. The resultant solid was washed with ethyl acetate to give the object compound (1) (0.95 g).

IR (Nujol): 3300, 1710 (shoulder), 1645, 1510 cm$^{-1}$

EXAMPLE 21

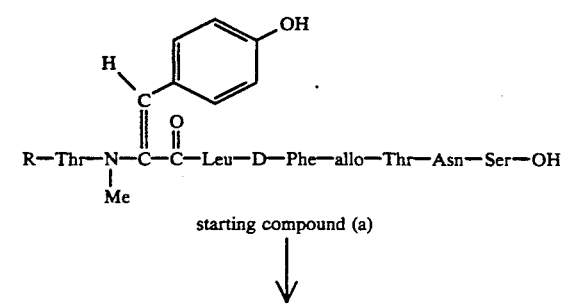

starting compound (a)

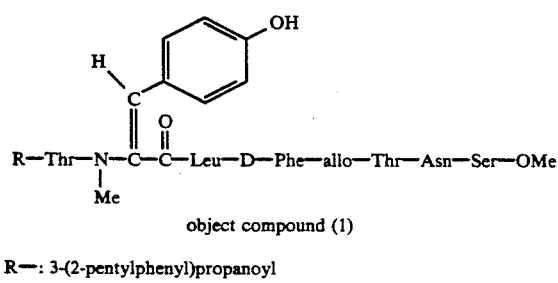

object compound (1)

R—: 3-(2-pentylphenyl)propanoyl

To a solution of the starting compound (a) (1.0 g) in methanol (2 ml) and ethyl acetate (20 ml) was added a solution (2 ml) of 10% trimethylsilyldiazomethane in n-hexane. After stirring for 5 minutes, the solvent was removed in vacuo. The residue was attached on a column of silica gel (MERCK 7734) (20 g) and eluted with chloroform-methanol (10:1, V/V) to give a solid of the object compound (1) (0.55 g).

IR (Nujol): 3300, 1735, 1645, 1530, 1510 cm$^{-1}$

Preparation 1

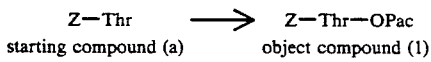

To a solution of the starting compound (a) (2.53 g), methanol (10 ml) and water (3 ml) was added cesium carbonate (1.63 g).

After the solvent was removed, the residue was dissolved in N,N-dimethylformamide and the mixture was added to phenacyl bromide (1.92 g). The mixture was stirred for 30 minutes at room temperature. The solvent was distilled off, and the residue was dissolved in ethyl acetate and washed with water. After the mixture was dried over magnesium sulfate and filtered, the solvent was evaporated to give crystal of the object compound (1) (3.7 g).

$[\alpha]_D^{20}$: −20.3° (C=1, CHCl₃)
IR (Nujol): 1745, 1690, 1545 cm$^{-1}$

Preparation 2

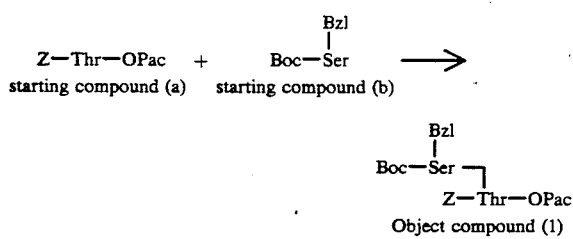

To a solution of the starting compound (a) (1.48 g) and the starting compound (b) (2.5 g) in dichloromethane (80 ml) were added 1-ethyl-3-(3-dimethylaminopropyl)carbodiimide hydrochloride (0.764 g) and 4-dimethylaminopyridine (0.488 g) at 0° C. After stirring for 6 hours, solvent was evaporated.

The residue was dissolved in ethyl acetate, and the mixture was washed with water, 1N-hydrochloric acid, a saturated aqueous solution of sodium bicarbonate and water.

After drying over magnesium sulfate and filtration, the solvent was evaporated to give the object compound (1) (2.58 g).

$[\alpha]_D^{20}$: +9.76° (C=0.3, CHCl₃)
IR (CHCl₃): 1755, 1720, 1705, 1505 cm$^{-1}$
NMR (CDCl₃, δ): 1.37 (3H, d, J=6Hz), 1.45 (9H, s), 3.70 (1H, m), 3.88 (1H, m), 4.52 (2H, m), 4.23 (1H, m), 5.17 (2H, s), 5.37 (2H, s)

Preparation 3

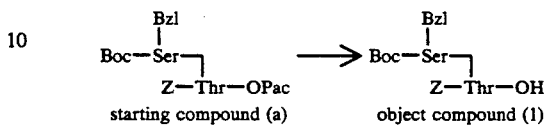

To a solution of the starting compound (a) in 90% aqueous acetic acid (100 ml) was added zinc powder (11 g) under stirring and the mixture was stirred for 2 hours under ice-cooling and 1 hour at room temperature.

After the mixture was filtered, filtrate was concentrated, adjusted to pH 2 with citric acid and extracted with ethyl acetate.

After the extract was dried over magnesium sulfate and filtered, solvent was evaporated. The residue was washed with petroleum ether to give the object compound (1) (5.4 g).

NMR (CDCl₃, δ): 1.30 (3H, d, J=6Hz), 1.40 (9H, s), 3.60 (1H, m), 3.82 (1H, m)

Preparation 4

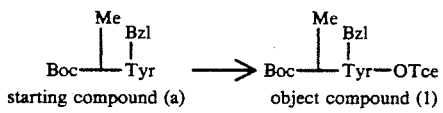

To a solution of the starting compound (a) (7.7 g) in dichloromethane (60 ml) were added 2,2,2-trichloroethanol (2.105 ml), 1-ethyl-3(3-dimethylaminopropyl)-carbodiimide hydrochloride (4.2 g) and 4-dimethylaminopyridine (244 mg) under stirring at 0° C., and the mixture was stirred for 1 hour at 0° C. and evaporated. The residue was dissolved in ethyl acetate and washed with water, 1N hydrochloric acid, water and a saturated aqueous solution of sodium bicarbonate.

After the mixture was dried over magnesium sulfate and filtered, the filtrate was evaporated to give the object compound (1) (9.37 g).

$[\alpha]_D^{19}$: −29.84° (C=0.4, CHCl₃)
IR (CHCl₃) 1755, 1690, 1610, 1510 cm$^{-1}$ Preparation 5

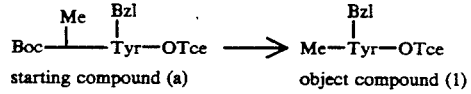

The starting compound (a) (9.3 g) was cooled to 0° C. and added to trifluoroacetic acid (15 ml).

The mixture was stirred for 30 minutes at 0° C. and evaporated. The residue was dissolved in ethyl acetate and washed with water, a saturated aqueous solution of sodium bicarbonate and water. After drying over magnesium sulfate and filtration, the solvent was distilled off to give the object compound (6 g).

NMR (CDCl₃, δ): 2.45 (3H, s), 3.03 (2H, m), 3.62 (1H, t, J=7Hz), 4.75 (2H, m), 5.06 (2H, s), 6.94 (2H, d, J=8Hz), 7.15 (2H, d, J=8Hz), 7.3–7.5 (5H, m)

Preparation 6

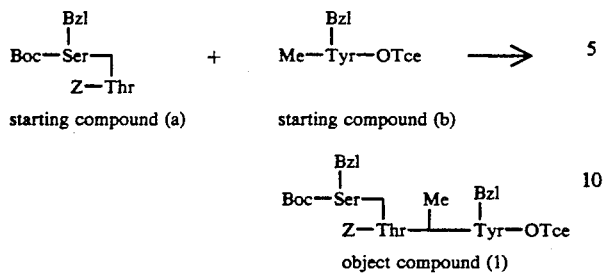

starting compound (a)    starting compound (b)

object compound (1)

To a solution of the starting compound (a) (4.07 g) and the starting compound (b) (4.70 g) in dichloromethane (40 ml) was added 1-ethoxycarbonyl-2-ethoxy-1,2-dihydroquinoline (2.8 g) and the mixture was stirred for 24 hours at room temperature. The solvent was evaporated and the residue was dissolved in ethyl acetate and washed with 1N hydrochloric acid, water, a saturated aqueous solution of sodium bicarbonate and water.

After drying over magnesium sulfate and filtration, the solvent was evaporated to give the object compound (1) (4.35 g).

$[\alpha]_D^{20}$: −27.88° (C=0.12, CHCl₃)

IR (CHCl₃) 1750, 1710, 1655, 1510 cm⁻¹

NMR (CDCl₃, δ): 1.18 (3H, d, J=6Hz), 1.36 (9H, s), 2.92 (3H, s), 4.69 (2H, s), 4.91 (2H, s), 5.01 (2H, s), 6.80 (2H, d, J=8Hz), 7.02 (2H, d, J=8Hz)

Preparation 7

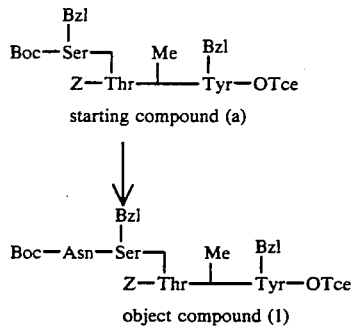

starting compound (a)

object compound (1)

The starting compound (a) (4.35 g) was cooled to 0° C. and added to trifluoroacetic acid (20 ml). After the mixture was stirred for 45 minutes at 0° C., the solvent was evaporated. The residue was dissolved in ethyl acetate and washed with a saturated aqueous solution of sodium bicarbonate and water. After the solution was dried over magnesium sulfate and filtered, the solvent was evaporated. The residue was dissolved in dichloromethane (100 ml).

To the solution were added Boc-Asn (1.2 g), 1-ethyl-3-(3-dimethylaminopropyl)carbodiimide hydrochloride (990 mg) and 1-hydrobenzotriazole (700 mg). The mixture was stirred for 4 hours at 0° C. and washed with 1N hydrochloric acid, water, a saturated aqueous solution of sodium bicarbonate and water, and the solvent was evaporated to give the object compound (1) (4.75 g).

$[\alpha]_D^{20}$: −15.7° (C=0.1, CHCl₃)

IR (KBr): 1740, 1690, 1645, 1510 cm⁻¹

NMR (CDCl₃, δ): 1.25 (3H, d, J=6Hz), 1.43 (9H, s), 3.00 (3H, s), 2.55 (1H, m), 2.80 (1H, m), 3.05 (1H, m), 3.37 (1H, m), 3.62 (1H, m), 3.82 (1H, m), 6.88 (2H, d, J=8.5Hz), 7.09 (2H, d, J=8.5Hz)

Preparation 8

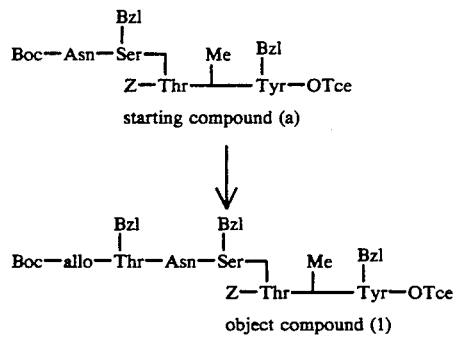

starting compound (a)

object compound (1)

The object compound (1) was obtained by reacting the starting compound (a) according to a similar manner to that of Preparation 7.

$[\alpha]_D^{22}$: −13.04° (C=0.11, CHCl₃)

IR (KBr): 1740, 1700, 1655, 1510 cm⁻¹

NMR (CDCl₃, δ): 1.18, 1.27 (each 3H, d, J=6Hz), 1.43 (9H, s), 2.52 (1H, m), 2.80 (1H, m), 3.00 (3H, s), 3.36 (1H, m), 4.99 (2H, s), 6.87 (2H, d, J=8Hz), 7.10 (2H, d, J=8Hz)

Preparation 9

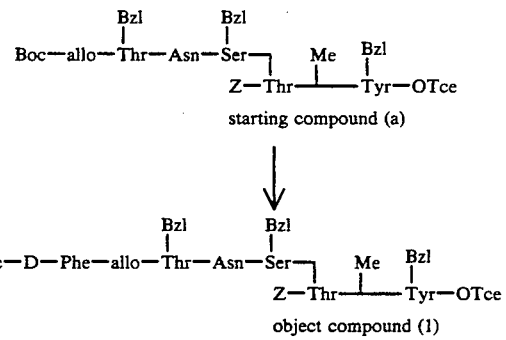

starting compound (a)

object compound (1)

The object compound (I) was obtained by reacting the starting compound (a) according to a similar manner to that of Preparation 7.

$[\alpha]_D^{21}$: −15.19 (C=0.1, CHCl₃)

IR (KBr): 1740, 1650, 1635, 1510 cm⁻¹

NMR (CDCl₃, δ): 1.11 (3H, d, J=6Hz), 1.27 (3H, d, J=6Hz), 1.33 (9H, s), 3.01 (3H, s), 4.72 (2H, s), 4.98 (2H, s), 6.87 (2H, d, J=8Hz), 7.10 (2H, d, J=8Hz)

Preparation 10

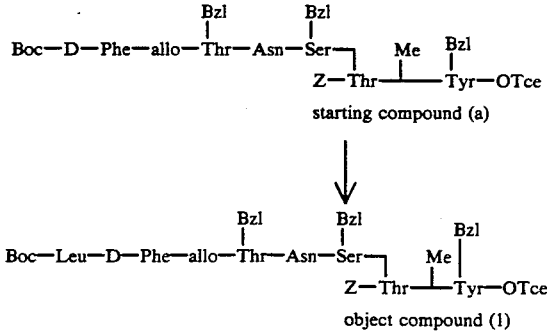

starting compound (a)

object compound (1)

The object compound (1) was obtained by reacting the starting compound (a) according to a similar manner to that of Preparation 7.

$[\alpha]_D^{21}$: −19.07° (C=0.1, CHCl₃)
IR (KBr): 1740, 1635, 1510 cm⁻¹
NMR (CDCl₃, δ): 0.81 (6H, m), 1.13, 1.28 (each 3H, d, J=6Hz), 1.40 (9H, s), 3.02 (3H, s), 4.96 (2H, s), 6.87, 7.09 (each 2H, d, J=8Hz)

Preparation 11

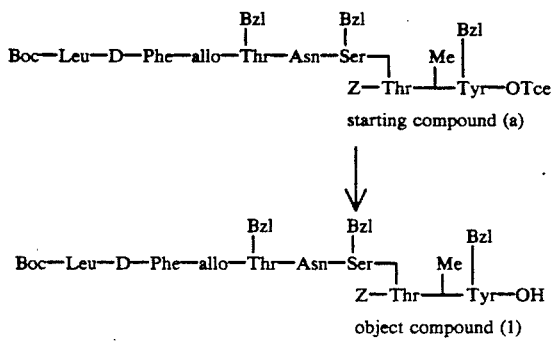

To a solution of the starting compound (a) (4.2 g) in 90% aqueous acetic acid (80 ml) was added zinc powder (9 g) at 0° C., and the mixture was stirred for 2 hours at 0° C. and 1 hour at room temperature.

After the mixture was filtered, filtrate was concentrated. Chloroform was added to the residue and the mixture was washed with 1N hydrochloric acid and water.

After the mixture was dried over magnesium sulfate and filtered, the solvent was evaporated. The residue was subjected to column chromatography on silica gel (150 g) and the elution was carried out with 2% methanol in chloroform and then 8% methanol in chloroform. Fractions containing the object compound were evaporated to give the object compound (1) (3.4 g).

$[\alpha]_D^{21}$: −23.42° (C=0.1, MeOH)
IR (KBr): 1635, 1510 cm⁻¹

Preparation 12

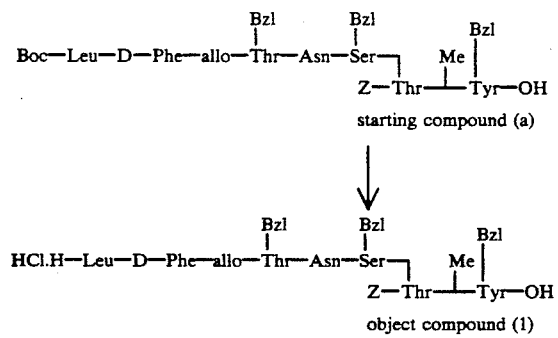

The starting compound (a) (3.4 g) was cooled to 0° C. and added to trifluoroacetic acid (20 ml).

After the mixture was stirred for 1 hour at 0° C., the solvent was evaporated. The residue was dissolved in a solution of hydrogen chloride in dioxane and then evaporated. The residue was dissolved in chloroform and washed with water. After the solution was dried over magnesium sulfate and filtered, the solvent was evaporated to give object compound (1) (3.27 g).

$[\alpha]_D^{21}$: −18 87° (C=0.12, MeOH)

IR (KBr): 1650, 1510 cm⁻¹

Preparation 13

To a solution of potassium hydroxide (26.8 g) in ethanol (500 ml) was added glycine (14.6 g) and 4-methoxymethoxybenzaldehyde (48.5 g) at room temperature. After stirring for 19 hours, the solvent was removed in vacuo. The residue was dissolved in water and acidified with hydrochloric acid. The solution was washed with ethyl acetate and adjusted to pH 6.0 with sodium bicarbonate. White solid was precipitated and collected to give 0-methoxymethyl-β-hydroxytyrosine (9.2 g).

mp: 164°–166° C.
IR (KBr): 1610 cm⁻¹

Preparation 14

To a solution of 0-methoxymethyl-β-hydroxytyrosine (21.0 g) in 1N-sodium hydroxide (250 ml) was added dimethylsulfate (16.5 g). After stirring for 20 min. at 90° C., the solution was acidified with diluted hydrochloric acid in ice bath. The acidic solution was washed with diethyl ether and adjusted to pH 6.0 with 1N-sodium hydroxide. After evaporation, the solid was collected by filtration to give O-methoxymethyl-N-methyl-β-hydroxytyrosine (5.2 g).

mp: 177°–178° C.
IR (KBr): 3100, 1600 cm⁻¹

Preparation 15

To a solution of O-methoxymethyl-N-methyl-β-hydroxytyrosine (15.1 g) and bis(trimethylsilyl)acetamide (25 ml) in dichloromethane (150 ml) was added a solution of 2-nitrophenylsulfenyl chloride (11.2 g) in dichloromethane (50 ml). After stirring for 2 hours at 0° C., bis(trimethylsilyl)acetamide (10 ml) and 2-nitrophenylsulfenyl chloride (5.6 g) was added to the solution. The mixture was stirred for 3 hours at room temperature and added to 1N-sodium hydroxide (200 ml). The organic layer was washed with water (300 ml) and the aqueous solutions were combined. After the aqueous solution was acidified with diluted hydrochloric acid, the product was extracted with ethyl acetate (300 ml) and the extract was washed with water (100 ml×3). After the solution was dried over magnesium sulfate, the solvent was removed in vacuo to give O-methoxymethyl-N-methyl-N-(2-nitrophenylthio)-β-hydroxytyrosine (20.5 g).

mp: 59°–60° C.
IR (KBr): 3400, 1700 cm⁻¹

Preparation 16

To a solution of O-methoxymethyl-N-methyl-N-(2-nitrophenylthio)-β-hydroxytyrosine (20.0 g) in ethyl acetate (100 ml) was added diazomethane in diethyl ether (80 ml). After stirring for 10 minutes, the solvent was removed in vacuo. The residue was put on a silica gel column (MERCK 7734: 500 g) and eluted with chloroform to O-methoxymethyl-N-methyl-N-(2-nitrophenylthio)-β-hydroxytyrosine methyl ester. (threo isomer: 8.82 g, erythro isomer: 6.63 g)

threo isomer

IR (Film): 3500, 2950 1735 cm⁻¹
TLC: Rf=0.40 [MERCK ART 5715, AcOEt-n-Hex(1:1)]

erythro isomer

IR (Film): 3500, 2950 1735 cm⁻¹

TLC: Rf=0.31 [MERCK ART 5715, AcOEt-n-Hex(1:1)]

Preparation 17

To a solution of O-methoxymethyl-N-methyl-N-(2-nitrophenylthio)-β-hydroxytyrosine methyl ester (erythro isomer) (3.85 g) in dichloromethane (30 ml) were added triethylamine (1.38 g), 4-dimethylaminopyridine (0.45 g) and benzoyl chloride (1.92 g). After stirring for 16 hours at room temperature, 3-dimethylaminopropylamine (3.3 g) was added to the mixture and the solvent was removed in vacuo. The residue was dissolved in ethyl acetate (30 ml) and washed with dil. hydrochloric acid, sodium bicarbonate aqueous solution and water. After evaporating, the residue was put on a column of silica gel (MERCK 7734, 150 g) and eluted with n-hexane-ethyl acetate (5:2, V/V) to give O-methoxymethyl-N-methyl-N-(2-nitrophenylthio)-β-benzoyloxytyrosine methyl ester (erythro isomer) (4.49 g).

IR (Film): 2950, 1740 cm$^{-1}$

TLC: Rf=0.23 (MERCK ART 5715, ethyl acetate: n-hexane=1:2)

Preparation 18

The following compound was obtained according to a similar manner to that of Preparation 17.

O-Methoxymethyl-N-methyl-N-(2-nitrophenylthio)-β-benzoyloxytyrosine methyl ester (threo isomer)
mp: 114°-115° C.

IR (CHCl$_3$) 2950, 1740 cm$^{-1}$

TLC: Rf=0.26 (MERCK ART 5715, ethyl acetate: n-hexane=1:2)

Preparation 19

To a solution of O-methoxymethyl-N-methyl-N-(2-nitrophenylthio)-β-benzoyloxytyrosine methyl ester (threo isomer) (4.94 g) in dichloromethane (50 ml) were added thiophenol (4.8 ml) and trifluoroacetic acid (2.5 ml) at 0° C. After stirring for 30 minutes, sodium bicarbonate aqueous solution was added to the mixture. The organic layer was washed with sodium bicarbonate aqueous solution and brine. After evaporating, the residue was put on a column of silica gel (MERCK 7734, 100 g) and eluted with 5% methanol in chloroform to give O-methoxymethyl-N-methyl-β-benzoyloxytyrosine methyl ester (threo isomer) (0.32 g).

TLC: Rf=0.31 (MERCK ART 5715, AcOEt: n-Hex=1:1)

Preparation 20

The following compound was obtained according to a similar manner to that of Preparation 19.

O-Methoxymethyl-N-methyl-β-benzoyloxytyrosine methyl ester (erythro isomer)

TLC: Rf=0.25 (MERCK ART 5715, AcOEt: n-Hex=1:1)

Preparation 21

To a solution of N-benzyloxycarbonyl-L-threonine (3.7 g) and O-methoxymethyl-N-methyl-β-benzoyloxytyrosine methyl ester (threo isomer) (3.11 g) in dichloromethane (50 ml) was added ethyl 1,2-dihydro-2-ethoxy-1-quinolinecarboxylate (2.9 g). After stirring for 20 hours at room temperature, the solvent was removed in vacuo. The residue was dissolved in ethyl acetate (50 ml) and washed with dil. hydrochloric acid, sodium bicarbonate aqueous solution and water. After evaporation, the residue was put on a column of silica gel (MERCK 7734, 100 g) and eluted with n-hexane-ethyl acetate (1:1, V/V) to give N-(N-benzyloxycarbonyl-L-threonyl)-O-methoxymethyl-N-methyl-β-benzoyloxytyrosine methyl ester (threo isomer) (2.04 g).

IR (Film): 3400, 2950, 1740 (shoulder), 1720 cm$^{-1}$

TLC: Rf=0.36 (MERCK ART 5715, MeOH:CHCl$_3$=3:97)

Preparation 22

The following compound was obtained according to a similar manner to that of Preparation 21.

N-(N-Benzyloxycarbonyl-L-threonyl)-O-methoxymethyl-N-methyl-β-benzoyloxytyrosine methyl ester (erythro isomer)

IR (Film): 2950, 1740, 1730 (shoulder) cm$^{-1}$

TLC: Rf=0.23 (MERCK ART 5715, AcOEt: n-Hex=1:2)

Preparation 23

$$Z-Thr-N(Me)-\underset{\underset{Me}{|}}{C}H(\overset{Mmp}{\diagdown}\!\!\!\overset{H}{\diagup}\!\!\!C\!-\!O)-\overset{O}{\overset{\|}{C}}-OMe$$

object compound (1)

To a solution of β-benzoyloxy-N-(N-benzyloxycarbonyl-L-threonyl)-O-methoxymethyl-N-methyltyrosine methyl ester (threo isomer) (1.20 g) in toluene (20 ml) was added 1,8-diazabicyclo[5.4.0]undec-7-ene (0.30 g). After stirring for 0.5 hours at room temperature, 7% hydrochloric acid (10 ml) was added to the mixture. The organic layer was washed with water and sodium bicarbonate aqueous solution. After the organic solution was dried over magnesium sulfate, the solvent was removed in vacuo to give the object compound (1) (0.95 g).

IR (Film): 3400, 2950, 1720 cm$^{-1}$ $[\alpha]_D^{22}$: −7.7° (C=0.64, MeOH)

The object compound (1) was obtained also by reacting β-benzoyloxy-N-(N-benzyloxycarbonyl-L-threonyl)-O-methoxymethyl-N-methyltyrosine methyl ester (erythro isomer) instead of β-benzoyloxy-N-(N-benzyloxycarbonyl-L-threonyl)-O-methoxymethyl-N-methyltyrosine methyl ester (threo isomer).

Preparation 24

$$Z-Thr-N(Me)-\underset{\underset{Me}{|}}{C}H(\overset{Mmp}{\diagdown}\!\!\!\overset{H}{\diagup}\!\!\!C\!-\!O)-\overset{O}{\overset{\|}{C}}-OMe$$

starting compound (a)

↓

$$Z-Thr-N(Me)-\underset{\underset{Me}{|}}{C}H(\overset{Mmp}{\diagdown}\!\!\!\overset{H}{\diagup}\!\!\!C\!-\!O\!-\!Si')-\overset{O}{\overset{\|}{C}}-OMe$$

object compound (1)

To a solution of the starting compound (a) (1.0 g) in N,N-dimethylformamide (10 ml) were added tert-butyldimethylsilyl chloride (0.75 g) and imidazole (0.34 g). After stirring for 16 hours at room temperature, ethyl acetate (30 ml) and ice (50 g) were added to the mixture. The organic layer was washed with dil. hydrochloric acid, sodium bicarbonate aqueous solution and water. The solvent was removed in vacuo. The residue was put on a column of silica gel (MERCK 7734, 30 g) and eluted with chloroform to give the object compound (1) (1.21 g).

IR (Film): 2950, 1720 cm$^{-1}$
$[\alpha]_D^{22}$: −55.9° (C=0.56, MeOH)

Preparation 25

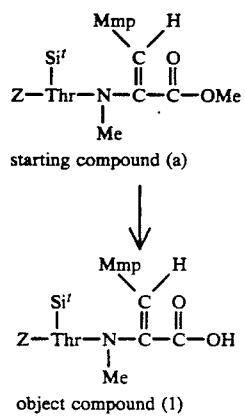

starting compound (a)

object compound (1)

To a solution of the starting compound (a) (0.95 g) was added 1N-sodium hydroxide aqueous solution (4.8 ml). After stirring for 2 days at 30° C., the solvent was removed in vacuo. The residue was dissolved in ethyl acetate (20 ml) and washed with dil. hydrochloric acid and water.

Evaporation gave the object compound (1) (0.81 g).
IR (Film): 3300, 2950, 1720, 1700 (shoulder) cm$^{-1}$
$[\alpha]_D^{22}$: −82.9° (C=1.06, MeOH)

Preparation 26

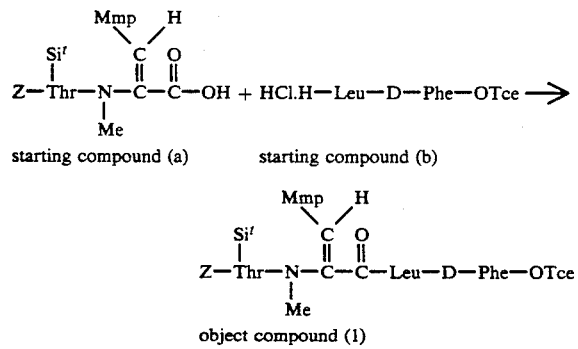

starting compound (a)    starting compound (b)

object compound (1)

To a mixture of the starting compound (a) (1.60 g) and the starting compound (b) (5.50 g) in dichloromethane (50 ml) were added triethylamine (1.25 g) and ethyl 1,2-dihydro-2-ethoxy-1-quinolinecarboxylate (3.04 g). After stirring for 15 hours at room temperature, a white solid was filtered off and the starting compound (b) (2.23 g), triethylamine (0.50 g) and ethyl 1,2-dihydro-2-ethoxy-1-quinolinecarboxylate (1.24 g) were added to the filtrate. The mixture was stirred for 18 hours and the solvent was removed in vacuo. The residue was dissolved in ethyl acetate (50 ml) and washed with dil. hydrochloric acid, sodium bicarbonate aqueous solution and water. After evaporating in vacuo, the residue was put on a column of silica gel (MERCK 7734, 100 g) and eluted with n-hexane-ethyl acetate (2:1, V/V) to give the object compound (I) (0.87 g).

IR (Film): 2950, 1760, 1740 (shoulder), 1720, 1660 cm$^{-1}$
$[\alpha]_D^{20}$: −31.5° (C=1.07, MeOH)

Preparation 27

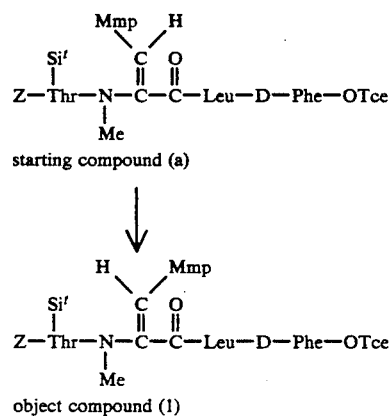

starting compound (a)

object compound (1)

A solution of the starting compound (a) (0.85 g) in toluene (100 ml) and acetone (10 ml) was irradiated by UV lamp (100 V) for 1.5 hours at 0° C. After evaporating, the residue was put on a column of silica gel (MERCK 7734, 50 g) and eluted with n-hexane-ethyl acetate (2:1, V/V) to give the object compound (1) (0.18 g).

TLC: Rf=0.22 (MERCK ART 5715, n-Hex: AcOEt=2:1)
IR (KBr): 3300, 1740 (shoulder), 1640 cm$^{-1}$ Preparation 28

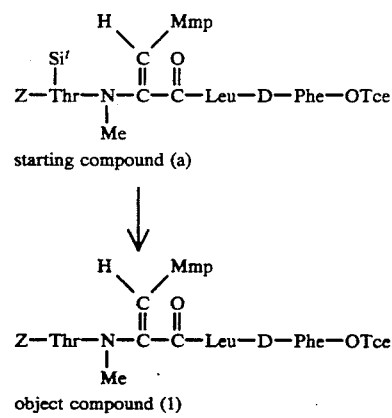

starting compound (a)

object compound (1)

The starting compound (a) (0.17 g) was dissolved in 67% acetic acid aqueous solution (10 ml). After stirring for 28 hours at 25° C., the solvent was removed in vacuo. The residue was dissolved in ethyl acetate (20 ml) and washed with sodium bicarbonate aqueous solution and water.

After concentration, the residue was washed with n-hexane and the solvent was removed in vacuo to give the object compound (1) (0.15 g).

IR (KBr): 3250, 1740 (shoulder), 1635 cm$^{-1}$
TLC: Rf=0.18 (MERCK ART 5715, n-Hex: AcOEt=1:1)

Preparation 29

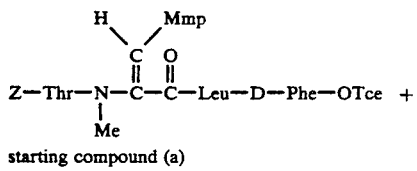
starting compound (a)

starting compound (b)

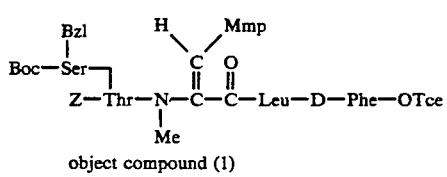
object compound (1)

To a solution of the starting compound (a) (0.14 g) in dichloromethane (5 ml) were added the starting compound (b) (0.10 g), water soluble carbodiimide hydrochloride (65 mg) and 4-dimethylaminopyridine (4 mg). After stirring for 12 hours at room temperature, N,N-dimethylaminopropylamine (50 mg) was added to the mixture and the solvent was removed in vacuo. The residue was dissolve din ethyl acetate (20 ml) and washed with dil. hydrochloric acid and water. After evaporating, the residue was put on a column of silica gel (MERCK 7734, 10 g) and eluted with n-hexane-ethyl acetate (1:1, V/V) to give the object compound (1) (0.16 g).

IR (KBr): 3300, 1700, 1640, 1495 cm$^{-1}$

TLC: Rf=0.38 (MERCK ART 5715, n-HEx:AcO-Et=1:1)

Preparation 30

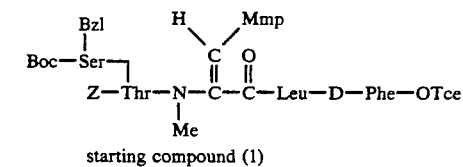
starting compound (1)

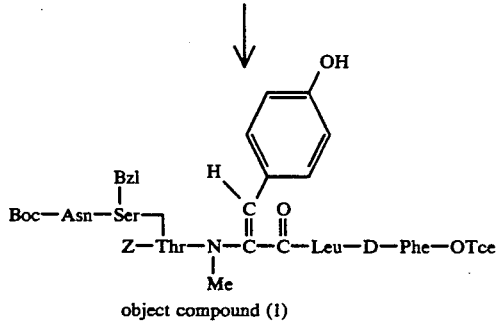
object compound (1)

The starting compound (a) (145 mg) was dissolved in a mixture of 4N-hydrogen chloride in dioxane (3 ml) and anisole (0.1 ml). After stirring for 30 minutes at room temperature, the solvent was removed in vacuo. The residue was dissolved in dichloromethane (3 ml). To the solution were added N-tert-butoxycarbonyl-L-asparagine (35 mg), triethylamine (13 mg), 1-hydroxybenzotriazole (18 mg) and water soluble carbodiimide hydrochloride (29 mg). After stirring for 1 hour at room temperature, 7% hydrochloric acid (5 ml) was added to the mixture. The organic layer was washed with water. After evaporating, the residue was subjected to preparative thin layer chromatography (MERCK 5744) and developed with 6% methanol in chloroform to give the object compound (1) (110 mg).

IR (KBr): 3300, 1650, 1505 cm$^{-1}$

TLC: Rf=0.44 (MERCK ART 5715, CHCl$_3$:MeOH=10:1)

Preparation 31

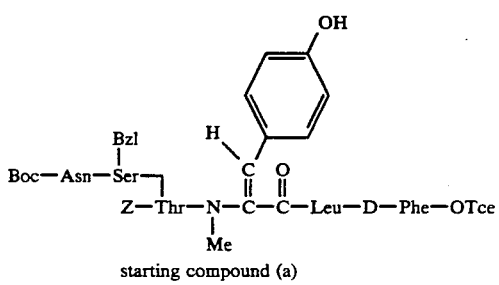
starting compound (a)

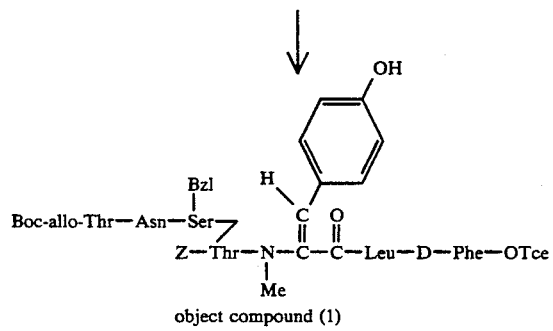
object compound (1)

The starting compound (a) (105 mg) was dissolved in a mixture of 4N hydrogen chloride in dioxane (3 ml) and anisole (0.1 ml). After stirring for 30 minutes at room temperature, the solvent was remove din vacuo. The residue was dissolved in dichloromethane (3 ml). To the solution were added N-tert-butoxycarbonyl-L-allothreonine (22 mg), triethylamine (9 mg), 1-hydroxybenzotriazole (12 mg) and water soluble carbodiimide hydrochloride (19 mg). After stirring for 8 hours at room temperature, 7% hydrochloric acid (5 ml) was added to the mixture. The organic layer was washed with water. After evaporating, the residue was subjected to preparative thin layer chromatography (MERCK 5744) and developed with 6% methanol in chloroform to give the object compound (1).

TLC: Rf=0.73 (MERCK ART 5715, CHCl$_3$:MeOH=5:1)

IR (KBr): 3300, 1740 (shoulder), 1650, 1500 cm$^{-1}$

Preparation 32

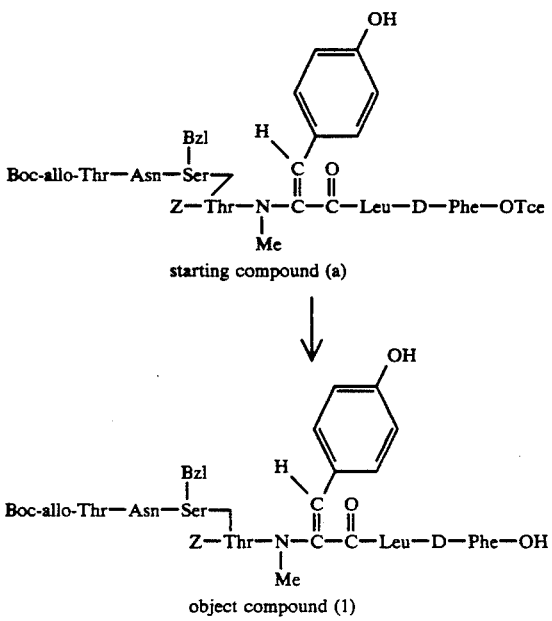

starting compound (a)

object compound (1)

To a solution of the starting compound (a) (58.5 mg) in 90% acetic acid aqueous solution (1 ml) was added zinc powder (30 mg). After stirring for 9 hours at room temperature, zinc powder (30 mg) was added to the mixture at 1-hour intervals until the starting compound (a) disappeared. After filtration, the solvent was removed in vacuo. The residue was dissolved in ethyl acetate (10 ml), washed with water and evaporated in vacuo. The residue was subjected to preparative thin layer chromatography (MERCK 5744) and developed with ethyl acetate-acetone-acetic acid-water (6:3:1:1, V/V) to give the object compound (1) (43.5 mg).

IR (KBr): 3330, 1650, 1505 cm$^{-1}$
TLC: Rf=0.16 [MERCK ART 5715, CHCl$_3$—MeOH—AcOH (10:1:0.1)]

Preparation 33

To a solution of phthalaldehyde (6.7 g) in dichloromethane (30 ml) was added ethoxycarbonylmethylene-triphenylphosphorane (17.42 g) and the mixture was stirred for 30 minutes at room temperature. The solvent was evaporated and the residue was dissolved in diethyl ether. After the mixture was filtered, the filtrate was evaporated. The residue was distilled under vacuum (125° C., 0.6 mmHg) to give (E)-3-(2-formylphenyl)-propenoic acid ethyl ester (6 g).

NMR (CDCl$_3$, δ): 1.24 (3H, t, J=6.5Hz), 4.19 (2H, q, J=6.5Hz), 6.28 (1H, d, J=15Hz), 7.5 (3H, m), 7.77 (1H, m), 8.43 (1H, d, J=15Hz), 10.18 (1H, s)

Preparation 34

To a solution of butyltriphenylphosphonium bromide (3.2 g) in tetrahydrofuran (50 ml) was added potassium tert-butoxide (900 mg) under nitrogen atmosphere and the mixture was stirred for 30 minutes at room temperature. The solution of (E)-3-(2-formylphenyl)propenoic acid ethyl ester (2.0 g) in tetrahydrofuran (30 ml ) was added to the mixture. The mixture was stirred for 1 hour. After the solvent was evaporated, the residue was dissolved in diethyl ether and washed with brine and water.

The solution was dried over magnesium sulfate, filtered and evaporated. The residue was subjected to column chromatography on silica gel (100 g) and eluted with a mixture of n-hexane and ethyl acetate (3:1). The fractions containing the object compound were evaporated to give (E)-3-[2-((Z)-1-pentenyl)phenyl]propenoic acid ethyl ester (2.00 g).

NMR (CDCl$_3$, δ): 0.88 (3H, t, J=7Hz), 1.34 (3H, t, J=6.5Hz), 1.42 (2H, m), 2.05 (2H, m), 4.27 (2H, q, J=6.5Hz), 5.85 (1H, dt, J=7, 11Hz), 6.39 (1H, d, J=16Hz), 6.56 (1H, d, J=11Hz), 7.3 (3H, m), 7.61 (1H, m), 7.92 (1H, d, J=16Hz)

Preparation 35

To a solution of (E)-3-[2-((Z)-1-pentenyl)phenyl]-propenoic acid ethyl ester (2 g) in 20% aqueous methanol was added potassium hydroxide (2.3 g). The mixture was stirred for 2 hours at 60° C., adjusted to pH 1 with hydrochloric acid and extracted with ethyl acetate. After the extract was dried over magnesium sulfate and filtered, the solvent was evaporated. The residue was dissolved in a mixture of n-hexane and ethyl acetate (4:1). The solution was added to dicyclohexylamine (1.63 ml) to give crystals. The crystals were dissolved in ethyl acetate and washed with 1N sulfuric acid. The solution was dried over magnesium sulfate, filtered and evaporated to give (E)-3-[2-((Z)-1-pentenyl)phenyl]-propenoic acid (0.92 g).

IR (Nujol): 1690, 1680, 1620 cm$^{-1}$

Preparation 36

(E)-3-[2-((Z)-1-Pentenyl)phenyl]propenoic acid (1.08 g) was dissolved in a mixture of dichloromethane (10 ml), oxalyl chloride (0.5 ml) and N,N-dimethylformamide (0.05 ml). After stirring for 1 hour under nitrogen atmosphere at room temperature, the solvent was evaporated. The residue was dissolved in n-hexane and the mixture was filtered. Filtrate was evaporated to give (E)-3-[2-((Z)-1-pentenyl)phenyl]propenoyl chloride (1.15 g).

IR (Neat): 1750, 1730, 1605, 1585 cm$^{-1}$
NMR (CDCl$_3$, δ): 0.88 (3H, t, J=6.5Hz), 1.45 (2H, m), 2.06 (2H, m), 5.95 (1H, dt, J=11, 7Hz), 6.58 (1H, d, J=11Hz), 6.66 (1H, d, J=16Hz), 7.4 (3H, m), 7.69 (1H, m), 8.12 (1H, d, J=16Hz)

EXAMPLE 22

The following compound was obtained according to a similar manner to that of Example 14.

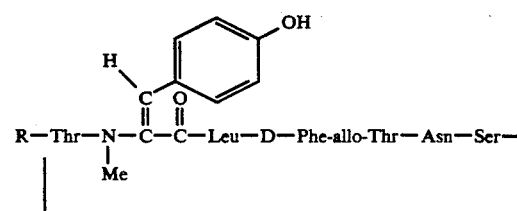

Molecular Weight: FAB-MS: m/z 1041.6 (M+H)+
What we claim is:
1. A compound of the formula:

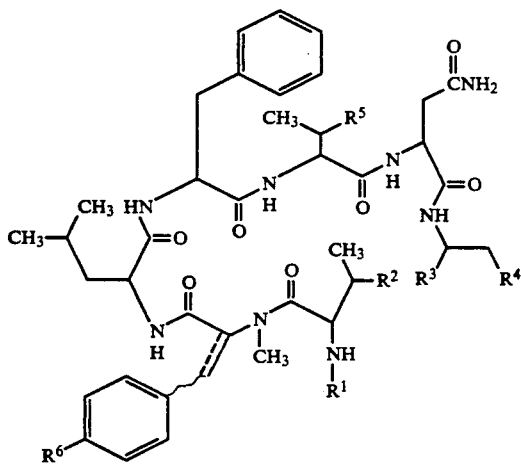 (I)

wherein $R^1$ is hydrogen; alkanoyl of 1 to 20 carbon atoms; alkoxycarbonyl of 2 to 20 carbon atoms; alkanesulfonyl of 1 to 20 carbon atoms; alkoxysulfonyl of 1 to 20 carbon atoms; benzoyl; toluoyl; naphthoyl; naphthylalkanoyl of 12 to 16 carbon atoms; phenylalkanoyl of 8 to 12 carbon atoms; naphthylalkanoyl of 12 to 16 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; phenylalkanoyl of 8 to 12 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms,, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; naphthylalkenoyl of 13 to 16 carbon atoms; phenylalkenoyl of 9 to 12 carbon atoms; naphthylalkenoyl of 13 to 16 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; phenylalkenoyl of 9 to 12 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; alkoxycarbonyl of 2 to 6 carbon atoms substituted with a phenyl; phenoxycarbonyl; naphthyloxycarbonyl; phenylglyoxyloyl; naphthylglyoxyloyl; benzenesulfonyl; p-toluenesulfonyl; or alkanoyl of 1 to 6 carbon atoms or glyoxyloyl substituted with a member selected from the group consisting of unsubstituted or substituted thienyl, pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidino, piperazinyl, indolyl, isoindolyl, indolizinyl, benzimidazolyl, quinolyl, isoquinolyl, indazolyl, benzotriazolyl, oxazolyl, isoxazolyl, oxadiazolyl, morpholinyl, sydnonyl, benzoxazolyl, benzoxadiazolyl, thiazolyl, isothiazolyl, thiadiazolyl, dihydrothiazinyl, thiazolidinyl, dihydrodithiinyl, dihydrodithionyl, benzothiazolyl, benzothiadiazolyl, furyl, dihydrooxathiinyl, benzothienyl, benzodithiinyl and benzoxathiinyl, said substituted members being substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms, and cyanoalkenylthio of 3 to 7 carbon atoms;

$R^2$ is hydroxy and $R^3$ is carboxy or protected carboxy, or $R^2$ and $R^3$ rae linked together to represent a group of the formula

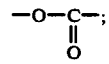

$R^4$ is hydroxy or protected hydroxy;

$R^5$ is hydroxy or protected hydroxy;

$R^6$ is hydroxy, protected hydroxy or lower alkoxy; and

═ is a single or a double bond, or a pharmaceutically acceptable salt thereof.

2. A compound of claim 1, wherein $R^1$ is hydrogen; alkanoyl of 1 to 20 carbon atoms; benzoyl; phenylalkanoyl of 8 to 12 carbon atoms; phenylalkanoyl of 8 to 12 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxylalkyl of 1 to 6 carbon atoms, and cyanoalkenylthio of 3 to 7 carbon atoms; phenylalkenoyl of 9 to 12 carbon atoms; phenylalkenoyl of 9 to 12 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms, and cyanoalkenylthio of 3 to 7 carbon atoms; alkoxycarbonyl of 2 to 6 carbon atoms substituted with a phenyl; or alkanoyl of 1 to 6 carbon atoms substituted with a member selected from the group consisting of substituted or unsubstituted thienyl, pyrrolyl, pyrrolinyl, imidazolyl, pyrazolyl, pyridyl, dihydropyridyl, pyrimidyl, pyrazinyl, pyridazinyl, triazolyl, tetrazolyl, pyrrolidinyl, imidazolidinyl, piperidino, piperazinyl, indolyl, isoindolyl, indolizinyl, benzimidazolyl, quinolyl, isoquinolyl, indazolyl, benzotriazolyl, oxazolyl, isoxazolyl, oxadiazolyl, morpholinyl, sydnonyl, benzoxazolyl, benzoxadiazolyl, thiazolyl, isothiazolyl, thiadiazolyl, dihydrothiazinyl, thiazolidinyl, dihydrodithiinyl, dihydrodithionyl, benzothiazolyl, benzothiadiazolyl, furyl, dihydrooxathiinyl, benzothienyl, benzodithiinyl and benzoxathiinyl, said substituted members being substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms, and cyanoalkenylthio of 3 to 7 carbon atoms.

3. The compound of claim 1, wherein $R^1$ is hydrogen; alkanoyl of 1 to 20 carbon atoms; alkoxycarbonyl of 2 to 20 carbon atoms; alkanesulfonyl of 1 to 20 carbon atoms; alkoxysulfonyl of 1 to 20 carbon atoms; benzoyl; toluoyl; naphthoyl; naphthylalkanoyl of 12 to 16 carbon atoms; phenylalkanoyl of 8 to 12 carbon atoms; naphthylalkanoyl of 12 to 16 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; phenylalkanoyl of 8 to 12 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; naphthylalkenoyl of 13 to 16 carbon atoms; phenylalkenoyl of 9 to 12 carbon atoms; naphthylalkenoyl of 13 to 16 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; phenylalkenoyl of 9 to 12 carbon atoms substituted with a substituent selected from the group consisting of alkyl of 1 to 6 carbon atoms, alkenyl of 2 to 6 carbon atoms, alkoxy of 1 to 6 carbon atoms, alkylthio of 1 to 6 carbon atoms, alkylamino of 1 to 6 carbon atoms, cycloalkyl of 3 to 6 carbon atoms, cycloalkenyl of 3 to 6 carbon atoms, halogen, amino, protected amino, hydroxy, protected hydroxy, cyano, nitro, carboxy, protected carboxy, sulfo, sulfamoyl, imino, oxo, aminoalkyl of 1 to 6 carbon atoms, carbamoyloxy, hydroxyalkyl of 1 to 6 carbon atoms and cyanoalkenylthio of 3 to 7 carbon atoms; alkoxycarbonyl of 2 to 6 carbon atoms substituted with a phenyl; phenoxycarbonyl; naphthyloxycarbonyl; phenylglyoxyloyl; naphthylglyoxyloyl; benzenesulfonyl; or p-toluenesulfonyl.

4. A compound of claim 2, wherein $R^1$ is hydrogen, phenyl($C_2$-$C_6$)alkoxycarbonyl, $C_1$-$C_6$ alkanoyl, $C_{15}$-$C_{20}$ alkanoyl, benzoyl, thienyl($C_2$-$C_6$)alkanoyl, phenyl($C_3$-$C_6$)alkenoyl substituted with a $C_2$-$C_6$ alkenyl group, or phenyl ($C_2$-$C_6$)alkanoyl substituted with a $C_1$-$C_6$ alkyl group.

5. A compound of claim 4, wherein
$R^1$ is phenyl($C_2$-$C_6$)alkanoyl substituted with a $C_1$-$C_6$ alkyl group,
$R^2$ and $R^3$ are linked together to represent a group of the formula:

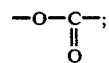

$R^4$ is hydroxy,
$R^5$ is hydroxy,
$R^6$ is hydroxy, and
$==$ is a double bond.

6. A compound of claim 5, wherein $R^1$ is 3-(2-pentylphenyl)propanoyl.

7. A compound of claim 6, which is a compound of the following structural formula:

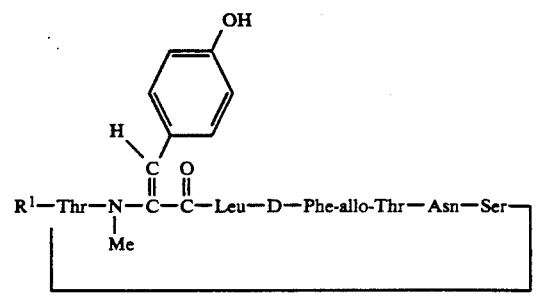

(in which R¹ is as defined in claim 6).

8. A pharmaceutical composition comprising a compound of claim 1 in an amount effective for the treatment or prevention of pain or asthma, in a pharmaceutically acceptable, substantially non-toxic carrier or excipient.

9. A method of treatment or prevention of asthma or pain comprising administering a therapeutically effective dosage of the compound of claim 1 to a patient in need thereof.

10. The method of claim 9, said therapeutically effective dosage being from 0.01 to 1000 mg per day.

* * * * *